(12) United States Patent
Cutler

(10) Patent No.: US 7,041,677 B2
(45) Date of Patent: May 9, 2006

(54) USE OF MONOCHLOROFLOSEQUINAN IN THE TREATMENT OF SEXUAL DYSFUNCTION

(75) Inventor: Neal R. Cutler, Los Angeles, CA (US)

(73) Assignee: R.T. Alamo Ventures I, LLC, Beverly Hills, CA (US)

( * ) Notice: Subject to any disclaimer, the term of this patent is extended or adjusted under 35 U.S.C. 154(b) by 185 days.

(21) Appl. No.: 10/282,286

(22) Filed: Oct. 28, 2002

(65) Prior Publication Data

US 2003/0191152 A1   Oct. 9, 2003

Related U.S. Application Data

(60) Provisional application No. 60/403,033, filed on Aug. 13, 2002, provisional application No. 60/361,150, filed on Mar. 1, 2002, provisional application No. 60/361,146, filed on Mar. 1, 2002, provisional application No. 60/360,829, filed on Mar. 1, 2002, and provisional application No. 60/360,954, filed on Mar. 1, 2002.

(51) Int. Cl.
*A61K 31/47* (2006.01)
*A61K 31/44* (2006.01)
*A61K 31/41* (2006.01)

(52) U.S. Cl. ............... 514/312; 514/311; 514/305; 514/708; 514/306; 514/307; 514/299

(58) Field of Classification Search ............... 514/305, 514/306, 299, 307, 311–708
See application file for complete search history.

(56) References Cited

U.S. PATENT DOCUMENTS

| | | | |
|---|---|---|---|
| 1,897,423 A | 2/1933 | Ferri | |
| 2,584,166 A | 2/1952 | Stevenson et al. | 167/64 |
| 2,696,209 A | 12/1954 | Varaney | 128/132 |
| 3,373,746 A | 3/1968 | White et al. | 128/294 |
| 4,311,707 A | 1/1982 | Birnbaum et al. | 424/305 |
| 4,478,822 A | 10/1984 | Haslam et al. | 424/78 |
| 4,552,891 A | 11/1985 | Ho et al. | 514/443 |
| 4,610,868 A | 9/1986 | Fountain et al. | 424/1.1 |
| 4,640,912 A | 2/1987 | Hausman | 514/54 |
| 4,746,508 A | 5/1988 | Carey et al. | 424/88 |
| 4,801,587 A | 1/1989 | Voss et al. | 514/248 |
| 5,011,931 A | 4/1991 | MacLean et al. | 546/155 |
| 5,079,264 A | 1/1992 | MacLean et al. | 514/629 |
| 5,393,773 A | 2/1995 | Craig et al. | 514/415 |
| 5,447,912 A | 9/1995 | Gerstenberg et al. | 514/12 |
| 5,474,535 A | 12/1995 | Place et al. | 604/60 |
| 5,554,639 A | 9/1996 | Craig et al. | 514/415 |
| 5,801,161 A | 9/1998 | Merkus | 514/52 |
| 5,864,037 A | 1/1999 | Chasin et al. | 544/118 |
| 5,869,479 A | 2/1999 | Kreutner et al. | 514/212 |
| 6,110,489 A | * 8/2000 | Cutler | 424/449 |
| 6,132,753 A | * 10/2000 | Cutler | 424/423 |
| 6,132,757 A | * 10/2000 | Cutler | 424/434 |
| 6,194,433 B1 | 2/2001 | Cutler | 514/312 |
| 6,258,373 B1 | 7/2001 | Cutler | 424/434 |
| 6,451,813 B1 | 9/2002 | Cutler et al. | 514/312 |

FOREIGN PATENT DOCUMENTS

| | | |
|---|---|---|
| EP | 0357581 B2 | 9/1998 |
| WO | WO 99/56666 | 11/1999 |

OTHER PUBLICATIONS

Baehr et al. "Isolation and characterization of cGMP phosphodiesterase from bovine rod outer segments" *J. Biol. Chem.* 254:11669–11677 (1979).

Cold, C.J. and Taylor, J.R., "The Prepuce," *British Journal of Urology*, 83, Suppl. 1:34–44 (1999).

Cortijo et al., "Investigation into the role of phosphodiesterase IV in bronchorelaxation, including studies with human bronchus," *J. Pharmacol.* 108:562–568 (1993).

Hidaka and Agano, "Human blood platelet 3':5' cyclic nucleotide phosphodiesterase. Isolation of low–Km and high–Km phosphodiesterase," *Biochem. Biophys. Acta* 429:485–497 (1976).

Lue et al., "Physiology of erection and pharmacological management of impotence," *J. Urol.* 37:829–836 (1987).

Morita et al., "Synthesis and Absolute Configuration of the Enantiomers of 7–Fluoro–1–methyl–3–(methylsulfinyl)–4(1H)–quinolinone (Flosequinan)," *Chem. Pharm. Bull.*, 42(10):2157–2160 (1994).

Park et al., "Vasculogenic female sexual dysfunction: The hemodynamic basis for vaginal engorgement insufficiency and clitoral erectile insufficiency," *Int. J. Impotence Res.* 9:27–37 (1997).

Porst et al., "Relevance of dynamic cavernosography to the diagnosis of venous incompetence in erectile dysfunction," *J. Urol.* 137:1163–1167 (1987).

* cited by examiner

*Primary Examiner*—Shaojia Anna Jiang
(74) *Attorney, Agent, or Firm*—Medlen & Carroll, LLP

(57) ABSTRACT

The present invention described the administration of halogenated flosequinan derivatives and the enantiomers of halogenated flosequinan derivatives for the treatment of sexual dysfunction (in males and females) and for the treatment of cardiovascular disease.

12 Claims, 39 Drawing Sheets

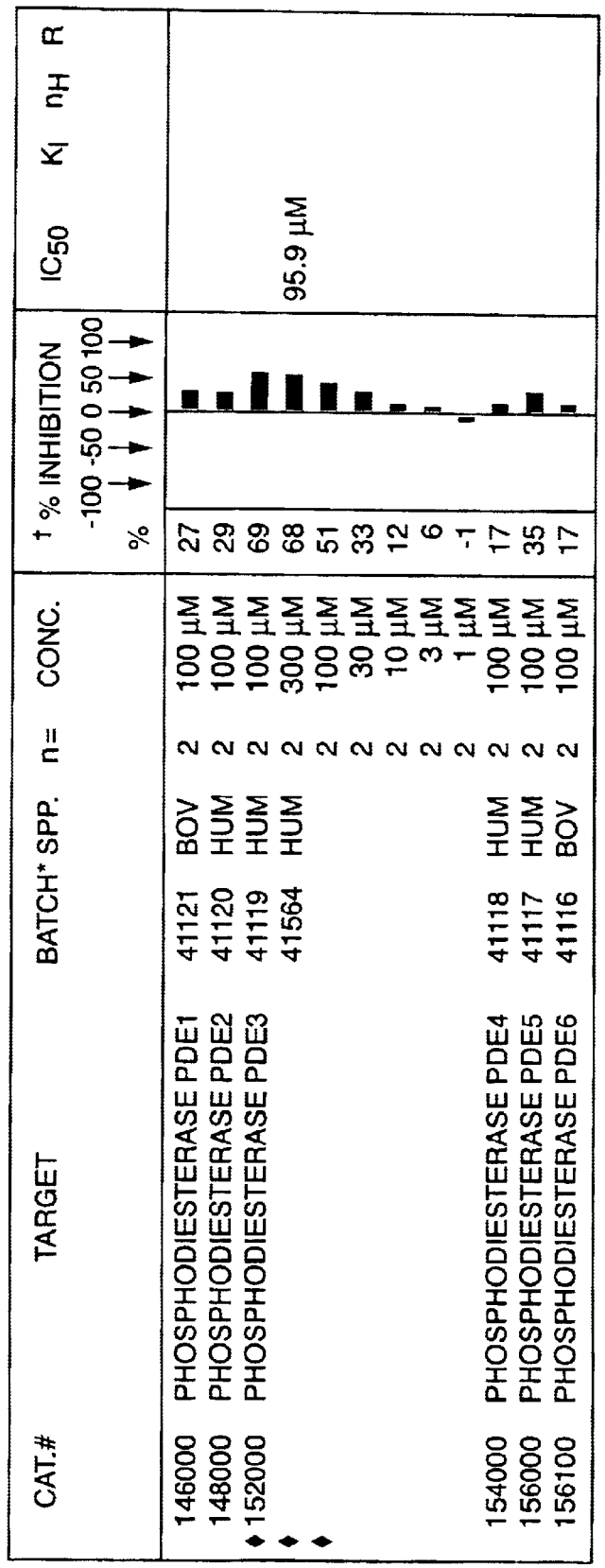

FIG. 14

| CAT.# | TARGET | BATCH* | SPP. | n= | CONC. | † % INHIBITION -100 -50 0 50 100 % | IC$_{50}$ | K$_I$ | n$_H$ | R |
|---|---|---|---|---|---|---|---|---|---|---|
| 146000 | PHOSPHODIESTERASE PDE1 | 41121 | BOV | 2 | 100 µM | 27 | | | | |
| 148000 | PHOSPHODIESTERASE PDE2 | 41120 | HUM | 2 | 100 µM | 29 | | | | |
| ◆ 152000 | PHOSPHODIESTERASE PDE3 | 41119 | HUM | 2 | 100 µM | 69 | 95.9 µM | | | |
| ◆ | | 41564 | HUM | 2 | 300 µM | 68 | | | | |
| ◆ | | | | 2 | 100 µM | 51 | | | | |
| | | | | 2 | 30 µM | 33 | | | | |
| | | | | 2 | 10 µM | 12 | | | | |
| | | | | 2 | 3 µM | 6 | | | | |
| | | | | 2 | 1 µM | -1 | | | | |
| 154000 | PHOSPHODIESTERASE PDE4 | 41118 | HUM | 2 | 100 µM | 17 | | | | |
| 156000 | PHOSPHODIESTERASE PDE5 | 41117 | HUM | 2 | 100 µM | 35 | | | | |
| 156100 | PHOSPHODIESTERASE PDE6 | 41116 | BOV | 2 | 100 µM | 17 | | | | |

*BATCH: REPRESENTS COMPOUNDS TESTED CONCURRENTLY IN THE SAME ASSAY(S).
◆ DENOTES ITEM MEETING CRITERIA FOR SIGNIFICANCE
† RESULTS WITH ≥ 50% STIMULATION OR INHIBITION ARE BOLDFACED. (NEGATIVE VALUES CORRESPOND TO STIMULATION BINDING OR ENZYME ACTIVITY)
R = ADDITIONAL COMMENTS
BOV = BOVINE; HUM = HUMAN

| CAT.# | TARGET | BATCH* | SPP. | n= | CONC. | † % INHIBITION % -100 -50 0 50 100 | IC$_{50}$ | K$_i$ | n$_H$ | R |
|---|---|---|---|---|---|---|---|---|---|---|
| ◆ 146000 | PHOSPHODIESTERASE PDE1 | 37070 | BOV | 2 | 100 µM | 71 | 65.6 µM | | | |
| ◆ | | 37525 | BOV | 2 | 300 µM | 65 | | | | |
| ◆ | | | | 2 | 100 µM | 55 | | | | |
| | | | | 2 | 30 µM | 42 | | | | |
| | | | | 2 | 10 µM | 30 | | | | |
| | | | | 2 | 3 µM | 20 | | | | |
| | | | | 2 | 1 µM | 19 | | | | |
| ◆ 148000 | PHOSPHODIESTERASE PDE2 | 36815 | HUM | 2 | 100 µM | 50 | >300 µM | | | |
| | | 37526 | HUM | 2 | 300 µM | 34 | | | | |
| | | | | 2 | 100 µM | 20 | | | | |
| | | | | 2 | 30 µM | 21 | | | | |
| | | | | 2 | 10 µM | 4 | | | | |
| | | | | 2 | 3 µM | 2 | | | | |
| | | | | 2 | 1 µM | -3 | | | | |

*BATCH: REPRESENTS COMPOUNDS TESTED CONCURRENTLY IN THE SAME ASSAY(S).
◆ DENOTES ITEM MEETING CRITERIA FOR SIGNIFICANCE
† RESULTS WITH ≥ 50% STIMULATION OR INHIBITION ARE BOLDFACED. (NEGATIVE VALUES CORRESPOND TO STIMULATION BINDING OR ENZYME ACTIVITY)
R = ADDITIONAL COMMENTS
BOV = BOVINE; HUM = HUMAN

FIG. 16A

| CAT.# | TARGET | BATCH* | SPP. | n= | CONC. | † % INHIBITION % -100 -50 0 50 100 | IC$_{50}$ | K$_i$ | nH | R |
|---|---|---|---|---|---|---|---|---|---|---|
| ◆ 152000 | PHOSPHODIESTERASE PDE3 | 37072 | HUM | 2 | 100 μM | 67 | 28.2 μM | | | |
| ◆ | | 37527 | HUM | 2 | 300 μM | 73 | | | | |
| ◆ | | | | 2 | 100 μM | 65 | | | | |
| ◆ | | | | 2 | 30 μM | 58 | | | | |
| | | | | 2 | 10 μM | 42 | | | | |
| | | | | 2 | 3 μM | 18 | | | | |
| | | | | 2 | 1 μM | 1 | | | | |
| 154000 | PHOSPHODIESTERASE PDE4 | 36817 | HUM | 2 | 100 μM | 15 | | | | |
| 156000 | PHOSPHODIESTERASE PDE5 | 36818 | HUM | 2 | 100 μM | 37 | | | | |
| 156100 | PHOSPHODIESTERASE PDE6 | 36819 | BOV | 2 | 100 μM | 16 | | | | |

*BATCH: REPRESENTS COMPOUNDS TESTED CONCURRENTLY IN THE SAME ASSAY(S).
◆ DENOTES ITEM MEETING CRITERIA FOR SIGNIFICANCE
† RESULTS WITH ≥ 50% STIMULATION OR INHIBITION ARE BOLDFACED. (NEGATIVE VALUES CORRESPOND TO STIMULATION BINDING OR ENZYME ACTIVITY)
R = ADDITIONAL COMMENTS
BOV = BOVINE; HUM = HUMAN

FIG. 16B

| CAT.# | TARGET | BATCH* | SPP. | n= | CONC. | †% INHIBITION -100 -50 0 50 100 % | IC$_{50}$ | K$_I$ | n$_H$ | R |
|---|---|---|---|---|---|---|---|---|---|---|
| 154000 | PHOSPHODIESTERASE PDE4 | 44171 | HUM | 2 | 100 µM | 32 | | | | |
| ◆156000 | PHOSPHODIESTERASE PDE5 | 43974 | HUM | 2 | 100 µM | 69 | 127 µM | | | |
| ◆ | | 44172 | HUM | 2 | 1000 µM | 50 | | | | |
| ◆ | | | | 2 | 300 µM | 76 | | | | |
| ◆ | | | | 2 | 100 µM | 60 | | | | |
| | | | | 2 | 30 µM | 32 | | | | |
| | | | | 2 | 10 µM | 18 | | | | |
| | | | | 2 | 3 µM | 6 | | | | |
| 156100 | PHOSPHODIESTERASE PDE6 | 43975 | BOV | 2 | 100 µM | 36 | | | | |

*BATCH: REPRESENTS COMPOUNDS TESTED CONCURRENTLY IN THE SAME ASSAY(S).
◆ DENOTES ITEM MEETING CRITERIA FOR SIGNIFICANCE
† RESULTS WITH ≥ 50% STIMULATION OR INHIBITION ARE BOLDFACED. (NEGATIVE VALUES CORRESPOND TO STIMULATION BINDING OR ENZYME ACTIVITY)
R = ADDITIONAL COMMENTS
BOV = BOVINE; HUM = HUMAN

FIG. 22B

| CAT.# | TARGET | BATCH* | SPP. | n= | CONC. | † % INHIBITION | | IC$_{50}$ | K$_i$ | n$_H$ | R |
|---|---|---|---|---|---|---|---|---|---|---|---|
| | | | | | | % | -100 -50 0 50 100 | | | | |
| 178010 | PROTEIN SERINE/THREONINE KINASE PKC, NON-SELECTIVE | 45090 | RAT | 2<br>2<br>2 | 1000 µM<br>300 µM<br>100 µM | 85<br>71<br>53 | → → → → → | <100 µM | | | |
| ♦<br>♦<br>♦ | | | | | | | | | | | |

*BATCH: REPRESENTS COMPOUNDS TESTED CONCURRENTLY IN THE SAME ASSAY(S).
♦ DENOTES ITEM MEETING CRITERIA FOR SIGNIFICANCE
† RESULTS WITH ≥ 50% STIMULATION OR INHIBITION ARE BOLDFACED. (NEGATIVE VALUES CORRESPOND TO STIMULATION BINDING OR ENZYME ACTIVITY)
R = ADDITIONAL COMMENTS

FIG. 29

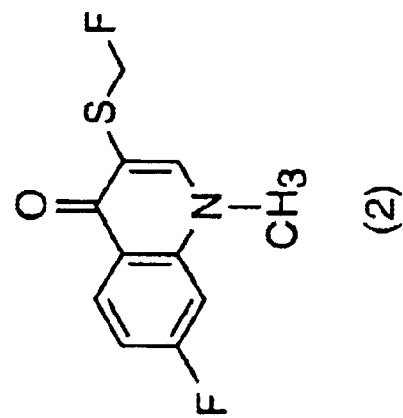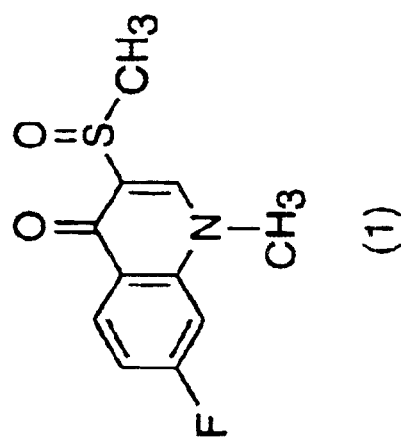
FIG. 32

| CAT.# | TARGET | BATCH* | SPP. | n= | CONC. | † % INHIBITION -100 -50 0 50 100 % | IC₅₀ | Kᵢ | nH | R |
|---|---|---|---|---|---|---|---|---|---|---|
| 146000 | PHOSPHODIESTERASE PDE1 | 45373 | BOV | 2 | 100 µM | 29 | | | | |
| 148000 | PHOSPHODIESTERASE PDE2 | 45375 | HUM | 2 | 100 µM | 10 | | | | |
| 152000 | PHOSPHODIESTERASE PDE3 | 45376 | HUM | 2 | 100 µM | 2 | | | | |
| 154000 | PHOSPHODIESTERASE PDE4 | 45253 | HUM | 2 | 100 µM | 12 | | | | |
| 156000 | PHOSPHODIESTERASE PDE5 | 45452 | HUM | 2 | 100 µM | 4 | | | | |
| 156100 | PHOSPHODIESTERASE PDE6 | 45453 | BOV | 2 | 100 µM | 23 | | | | |
| 180010 | PROTEIN SERINE/THREONINE KINASE PKCα | 45273 | HUM | 2 | 1000 µM | 10 | | | | |
| 178010 | PROTEIN SERINE/THREONINE KINASE PKC, NON-SELECTIVE | 45090 | RAT | 2 | 1000 µM | 74 | | | | |
|  |  | 45491 | RAT | 2 | 300 µM | 54 | | | | |
|  |  |  |  | 2 | 100 µM | 50 | | | | |

*BATCH: REPRESENTS COMPOUNDS TESTED CONCURRENTLY IN THE SAME ASSAY(S).

♦ DENOTES ITEM MEETING CRITERIA FOR SIGNIFICANCE

† RESULTS WITH ≥ 50% STIMULATION OR INHIBITION ARE BOLDFACED. (NEGATIVE VALUES CORRESPOND TO STIMULATION BINDING OR ENZYME ACTIVITY)

R = ADDITIONAL COMMENTS

BOV = BOVINE; HUM = HUMAN

| CAT.# | TARGET | BATCH* | SPP. | n= | CONC. | †% INHIBITION -100 -50 0 50 100 % | IC$_{50}$ | K$_i$ | nH | R |
|---|---|---|---|---|---|---|---|---|---|---|
| 214510 | CALCIUM CHANNEL TYPE L, BENZOTHIAZEPINE | 45139 | RAT | 2 | 1000 µM | 13 | | | | |
| 214600 | CALCIUM CHANNEL TYPE L DIHYDROPYRIDINE | 45167 | RAT | 2 | 1000 µM | 27 | | | | |
| 215000 | CALCIUM CHANNEL TYPE L PHENYLALKYLAMINE | 45262 | RAT | 2 | 1000 µM | 7 | | | | |
| 242500 | INOSITOL TRISPHOSPHATE IP$_3$ | 45039 | RAT | 2 | 1000 µM | 17 | | | | |

*BATCH: REPRESENTS COMPOUNDS TESTED CONCURRENTLY IN THE SAME ASSAY(S).
♦ DENOTES ITEM MEETING CRITERIA FOR SIGNIFICANCE
† RESULTS WITH ≥ 50% STIMULATION OR INHIBITION ARE BOLDFACED. (NEGATIVE VALUES CORRESPOND TO STIMULATION BINDING OR ENZYME ACTIVITY)
R = ADDITIONAL COMMENTS
BOV = BOVINE; HUM = HUMAN ized floosequinan deriva-
USE OF MONOCHLOROFLOSEQUINAN IN THE TREATMENT OF SEXUAL DYSFUNCTION This application for patent under 35 U.S.C. 111(a) claims priority in Provisional Application Ser. No. 60/403,033 filed on Aug. 13, 2002, Ser. No. 60/361,146 filed on Mar. 1, 2002, Ser. No. 60/360,829 filed on Mar. 18, 2002 and Ser. No. 60/360,954 filed on Mar. 1, 2002 under 35 U.S.C. 111(b).

FIELD OF THE INVENTION

The present invention relates to methods for the treatment of sexual dysfunction in males and females (including but not limited to erectile dysfunction in males) and, more particularly, to the use of halogenated flosequinan derivatives (and enantiomers of the same) in treatment of said sexual dysfunction. The present invention also relates to compositions and methods for the treatment of cardiovascular disease.

BACKGROUND

A. Sexual Dysfunction

Impotence or erectile insufficiency is a widespread disorder that is thought to affect about twelve percent of adult men under age forty-five, about twenty percent of men at age sixty, and about fifty-five percent of men at age seventy-five.

There is more than one cause of erectile dysfunction. For example, erectile dysfunction can be psychological, resulting from anxiety or depression, with no apparent somatic or organic impairment. Such erectile dysfunction, which is referred to as "psychogenic," is responsible for about fifteen to twenty percent of cases of impotence. In other cases, the erectile dysfunction is associated with atherosclerosis of the arteries supplying blood to the penis; such dysfunction is referred to as "arteriogenic" or "atherosclerotic." About forty to sixty percent of cases of impotence are arteriogenic in origin.

In still other cases, there is leakage from veins in the penis such that sufficient pressure for an erection can be neither obtained nor maintained. This dysfunction is referred to as "venous leakage," or "abnormal drainage." This condition is often exacerbated by the presence of some arteriogenic dysfunction whereby the supply of blood to the penis is impaired. In still other cases, the dysfunction is associated with a neuropathy, such as nerve damage arising from, for example, surgery or a pelvic injury, in the nervous system affecting the penis. Such a dysfunction is referred to as "neurogenic" and this accounts for about ten to fifteen percent of cases of impotence.

There is also a high incidence of erectile insufficiency among diabetics, particularly those with insulin-dependent diabetes mellitus. Erectile dysfunction in diabetics is often classified as "diabetogenic," although the underlying dysfunction is usually neurogenic associated with neuropathy, but may be arteriogenic or neurogenic and arteriogenic. About half of diabetic males suffer from erectile insufficiency, and about half of the cases of neurogenic impotence are in diabetics.

Additionally, erectile insufficiency is sometimes a side effect of certain drugs, such as beta-blockers that are administered to reduce blood pressure in persons suffering from hypertension, or drugs administered to treat depression or anxiety. Excessive alcohol consumption has also been linked to erectile insufficiency. Circumcision in males, which removes highly sensitive penile tissue (Cold, C. J. and Taylor, J. R., "The Prepuce" *British Journal of Urology*, 83, Suppl. 1:34–44, 1999) and subjects the glans and shaft of the penis to desensitization through keratinization of the remaining tissue, is also believed to be a contributing factor to some forms of erectile insufficiency (Fink K S, Carson C C, DeVellis R F. "Adult circumcision outcomes study: effect on erectile function, penile sensitivity, sexual activity and satisfaction" J Urol, 167:2113–6, 2002). Additionally, one cause of erectile insufficiency may act synergistically with one or more other causes of erectile insufficiency. In this regard, routine infant circumcision may be a latent causative factor in all instances of erectile insufficiency in circumcised males.

A number of methods to treat impotence are available. These treatments include pharmacological treatments, surgery and, in cases of psychogenic dysfunction, psychological counseling is sometimes effective. Psychogenic impotence often can be cured by counseling coupled with a demonstration to the patient that he is capable of having a full erection by inducing such an erection once or a few times in the patients. Insufficiency due to excessive alcohol consumption is sometimes cured by reducing or elimination such consumption.

In rare cases, where the insufficiency is physical because of venous leakage, surgery can usually be employed to repair the venous lesion and thereby either cure the insufficiency or, if there remains an erectile insufficiency after repair of the venous lesion, render the insufficiency amenable to treatment by pharmacological methods. Also, penile implants, which provide a mechanical means to produce an erection sufficient for vaginal penetration, are widely used to treat impotence. In recent years, implants have been employed, especially in cases where pharmacological intervention is ineffective, which are usually cases of severe atherogenic impotence. Treatment of impotence with penile implants, however, entails serious disadvantages. Such treatment requires surgery and necessitates total destruction of the erectile tissues of the penis, forever precluding normal erection.

Pharmacological methods of treatment are also available. Such methods, however, have not proven to be highly satisfactory and can be accompanied by severe side-effects. Papaverine is now widely used to treat impotence, although papaverine is ineffective in overcoming impotence due, at least in part, to severe atherosclerosis. Papaverine is effective in cases where the dysfunction is psychogenic or neurogenic and severe atherosclerosis is not involved. Injection of papaverine, a smooth muscle relaxant, or phenoxybenzamine, a non-specific blocker and hypotensive, into a corpus cavernosum has been found to cause an erection sufficient for vaginal penetration. Also, in cases where severe atherosclerosis is not a cause of the dysfunction, intracavernosal injection of phentolamine, an α-adrenergic blocker, causes an erection sufficient for vaginal penetration. The resulting erection is one of significantly shorter duration than that induced by intracavernosal injection of papaverine or phenoxybenzamine and is of such short duration that satisfactory sexual relations are difficult or impossible.

Treatment of impotence with papaverine or phenoxybenzamine often results in priapism, a locking-up of an erection for a long period of time, typically a few hours and sometimes longer than twenty-four hours. Priapism is a serious, deleterious side effect of treatment of erectile insufficiency with these drugs. Beyond the embarrassment that may be caused for some men, priapism is usually painful, irreversibly damages erectile tissue, and, to be relieved, requires bleeding or pharmacological intervention, such as injection of a sympathomimetic drug, such as adrenaline.

Even if priapism does not occur with use of papaverine, such use is associated with a painful, burning sensation in the first two or so minutes after the injection and there are indications that repeated use of papaverine causes undesirable, extensive intracavernous fibrosis. Further, as indicated above, impotence arising from severe atherosclerosis is not susceptible to treatment with papaverine, phenoxybenzamine, phentolamine or papaverine together with phentolamine. In any case, phenoxybenzamine is not suitable for use in treating impotence because it is a carcinogen.

Sildenafil citrate (Viagra) has also been utilized as a pharmacological treatment for impotence. However, sildenafil citrate has a lack of specificity for its target, enzyme phosphodiesterase 5 (PDE5), and exerts a definite inhibition on the enzyme phosphodiesterase 6 (PDE6), located in the retina. It has been shown that the inhibition of PDE6 results in color vision defects as a side effect of treatment with sildenafil citrate. Furthermore, side effects such as flushing, headache, nasal congestion, and dyspepsia (heartburn) have also been associated with sildenafil citrate treatment of impotence. (See, Moreira et al., "Side-effect profile of sildenafil citrate (Viagra) in clinical practice," *Urology*, 56(3): 474–76 (2000)).

Females have sexual dysfunction. Post-menopausal women often complain of discomfort with intercourse, dryness of the vagina and diminished vaginal arousal. Studies comparing sexual dysfunction in couples have revealed 40% of the men had erectile or ejaculatory dysfunction whereas 63% of the women had arousal or orgasmic dysfunctions. Similar to male sexual dysfunction, the prevalence of female sexual dysfunction has been shown to increase with age and be associated with the presence of vascular risk factors and the development of the menopause.

The clitoris is the homologue of the penis. It is a cylindrical, erectile organ composed of the glans, corporal body and the crura. The corporal body is surrounded by a fibrous sheath, tunica albuginea, which encases cavernosal tissue consisting of sinusoids and surrounding smooth muscle. The clitoris responds to sexual excitement by tumescence and erection, although this does not occur with the degree of pressure elevation as found during penile erection. The characteristics of the clitoral blood flow, however, approximately parallel those of the male. See K. Park et al., "Vasculogenic female sexual dysfunction: The hemodynamic basis for vaginal engorgement insufficiency and clitoral erectile insufficiency," *Int. J. Impotence Res.* 9:27 (1997).

Post-menopausal women and women with a history of vascular risk factors have been shown to have significantly more complaints of self-reported female vaginal and clitoral dysfunctions than pre-menopausal women or women without vascular risk factors. Such problems include, but are not limited to, atherosclerosis-induced vaginal engorgement insufficiency and clitoral erectile insufficiency syndromes.

B. Cardiovascular Disease

Cardiovascular disease is the number one cause of death in the United States. Medical Sciences Bulletin, No. 238; p. 1 (1997). While cardiovascular disease presents many different clinical manifestations, hypertension and congestive heart failure (CHF) are major components of this disease state. Uncontrolled hypertension can result in myocardial infarction and stroke. Congestive heart failure, if untreated, is an ultimately fatal disease that kills more than half its victims within five years of initial diagnosis. CHF affects about 3 million people in the United States and about 15 million worldwide. Currently, an estimated 400,000 new cases are diagnosed in the United States each year, and CHF is responsible for about 900,000 hospitalizations a year.

The current treatment approaches involve antihypertensive compounds, such as: beta-blockers, calcium channel blockers (especially dihydropyrimidines), angiotensin-converting enzyme (ACE) inhibitors, diuretics, and alpha-blockers. However, many patients fail to respond to (or tolerate poorly) these compounds.

For example, many patients do not respond to diuretics (with or without digitalis). Moreover, many patients cannot tolerate (or respond poorly to) ACE inhibitors. In addition the use of beta blockers has been associated with loss of glycemic control. Studies on the Glycemic and Lipidemic Effect of Atenolol and Propranolol in Normal and Diabetic Rats, (Abstract), Arzneimittelforschung, 44(4): 496–501 (April, 1994).

What is needed is a pharmaceutical that is effective in the treatment of sexual dysfunction in males and females but lacking in significant side effects. Additionally, what is needed is a pharmacological intervention for cardiovascular disease [including, but limited to, hypertension and congestive heart failure (also referred to as "CHF") that is less disruptive to the patient and is be better tolerated in comparison to existing treatment modalities.

SUMMARY OF THE INVENTION

The present invention relates to methods for the treatment of sexual dysfunction in males and females (including but not limited to erectile dysfunction) using halogenated derivatives of flosequinan and enantiomers of these same halogenated flosequinan derivatives. The present invention also describes methods for the synthesis of halogenated derivates of flosequinan and the enantiomers of these halogenated flosequinan derivatives.

The present invention also provides methods for the therapeutic use of halogenated derivates of flosequinan and the enantiomers of these same halogenated flosequinan derivatives for improving blood flow and supply to female sexual organs, and more particularly, methods for the treatment of female erectile dysfunction. In selected embodiment the methods of the present invention comprise the utilization of these pharmaceutical compositions to induce clitoral erections in females having erectile dysfunction.

The present invention also relates to compositions and methods for the treatment of cardiovascular disease.

A. Synthesis of Enantiomers of Derivatives of Flosequinan

I. Synthesis of Monochloroflosequinan

The present invention relates to heterocyclic compositions and methods for their synthesis. The compositions comprise a racemic mixture of monochloroflosequinan, and derivatives (e.g. the sulfone) thereof. Other compositions comprise enantiomers of monochloroflosequinan. The compositions also comprise chlorodesoxyflosequinan.

In one embodiment, the present invention contemplates compositions comprising racemic monochloroflosequinan (i.e. racemic 3-chloromethylsulfinyl-7-fluoro-1-methyl-4-quinolone). In another embodiment, the present invention contemplates compositions comprising the sulfone derivative of racemic monochloroflosequinan (i.e. 3-chloromethylsulfonyl-7-fluoro-1-methyl-4-quinolone). In one embodiment, the present invention contemplates compositions comprising a purified enantiomer of monochloroflosequinan, including derivatives thereof. In one embodiment, said purified enantiomer of monochloroflosequinan is a (+)-enantiomer (i.e. (S)-(+)-3-chloromethylsulfinyl-7-fluoro-1-methyl-4-quinolone). In another embodiment, said composition is substantially free of the (−)-enantiomer of monochloroflosequinan. In yet another embodiment, said purified enantiomer of monochloroflosequinan is a (−)-enantiomer (i.e. (R)-(−)-3-chloromethylsulfinyl-7-fluoro-1-methyl-4-quinolone). In another embodiment, said composition is substantially free of the (+)-enantiomer of monochloroflosequinan.

In some embodiments, a composition comprising a substantially purified enantiomer of monochloroflosequinan is contemplated. In some embodiments, the purified enantiomer (i.e. the (+)- or the (−)-enantiomer of monochloroflosequinan) represents at least 80% of the purified enantiomer preparation, more preferably at least 90%, more preferably at least 95% and even more preferably, at least 98% of the preparation. Likewise, the other enantiomer represents less than 20%, 10%, 5% or 2% of the preparation.

In some embodiments, a composition comprising an enantiomer of monochloroflosequinan (i.e. (S)-(+)-3-chloromethylsulfinyl-7-fluoro-1-methyl-4-quinolone or (R)-(−)-3-chloromethylsulfinyl-7-fluoro-1-methyl-4-quinolone) in enantiomeric excess is contemplated. In some embodiments, the major enantiomer in the composition is in at least 90% enantiomeric excess, and more preferably, 95% enantiomeric excess. In some embodiments, a composition comprising (S)-(+)-3-chloromethylsulfinyl-7-fluoro-1-methyl-4-quinolone having an optical purity of at least 85% is contemplated. In other embodiments, a composition comprising (S)-(+)-3-chloromethylsulfinyl-7-fluoro-1-methyl-4-quinolone having an optical purity of at least 95% is contemplated. In other embodiments, a composition comprising (R)-(−)-3-chloromethylsulfinyl-7-fluoro-1-methyl-4-quinolone having an optical purity of at least 85% is contemplated. In yet other embodiments, a composition comprising (R)-(−)-3-chloromethylsulfinyl-7-fluoro-1-methyl-4-quinolone having an optical purity of at least 95% is contemplated.

In one embodiment, the present invention contemplates compositions comprising chlorodesoxyflosequinan (i.e. 3-chloromethylthio-7-fluoro-1-methyl-4-quinolone).

In one embodiment, the present invention contemplates methods for the synthesis of racemic monochloroflosequinan. In another embodiment, the present invention contemplates methods for the synthesis of the sulfone derivative of racemic monochloroflosequinan. In yet other embodiments, the present invention contemplates methods for the stereopreferred synthesis (e.g. the preferential synthesis of one enantiomer) and separation of enantiomers of monochloroflosequinan. In one embodiment, a method for the synthesis of the (+)-enantiomer of monochloroflosequinan (i.e. (S)-(+)-3-chloromethylsulfinyl-7-fluoro-1-methyl-4-quinolone) in enantiomeric excess is contemplated. The method further provides additional separation steps. In another embodiment, a method for the synthesis of the (−)-enantiomer of monochloroflosequinan (i.e. (R)-(−)-3-chloromethylsulfinyl-7-fluoro-1-methyl-4-quinolone) in enantiomeric excess is contemplated. The method further provides additional separation steps. In some embodiments, the present invention provides methods of synthesis of chlorodesoxyflosequinan (i.e. 3-chloromethylthio-7-fluoro-1-methyl-4-quinolone).

In some embodiments, the present invention provides a method, comprising: a) providing: i) flosequinan, and ii) triphenyl phosphine; and b) reacting said flosequinan and triphenyl phosphine in an organic solvent under conditions such that desoxyflosequinan (7-fluoro-1-methyl-3-methylthio-4-quinolone) is produced; and c) further reacting said desoxyflosequinan with N-chlorosuccinimide and 2,2'-azobisisobutyronitrile in an organic solvent under conditions such that chlorodesoxyflosequinan (3-chloromethylthio-7-fluoro-1-methyl-4-quinolone) is produced. A variety of solvents can be used in this reaction. In some embodiments, said organic solvent in said reacting step b) is selected from the group consisting of carbon tetrachloride, xylene and toluene. In some embodiments, said providing step a) optionally provides iii) a catalyst, and said reacting step b) occurs in the presence of said catalyst. In some embodiments, said organic solvent in said reacting step b) is selected from the group consisting of xylene and toluene. A variety of solvents can be used in this reaction. A variety of catalysts are contemplated for this reaction. In some embodiments, said catalyst is tetrabromomethane. In some embodiments, said organic solvent in step c) is selected from the group consisting of carbon tetrachloride and benzene.

In another embodiment, the present invention provides a method, comprising: a) providing: i) flosequinan, ii) thionyl chloride, and iii) pyridine; and b) reacting said flosequinan, thionyl chloride and pyridine in an organic solvent under conditions such that chlorodesoxyflosequinan (3-chloromethylthio-7-fluoro-1-methyl-4-quinolone) is produced.

In another embodiment, the present invention provides a method, comprising: a) providing: i) chlorodesoxyflosequinan (3-chloromethylthio-7-fluoro-1-methyl-4-quinolone), ii) hydrogen peroxide, and iii) potassium carbonate; and b) reacting said chlorodesoxyflosequinan, hydrogen peroxide and potassium carbonate in a solvent under conditions such that monochloroflosequinan (3-chloromethylsulfinyl-7-fluoro-1-methyl-4-quinolone) is produced.

In yet other embodiments, the present invention provides a method, comprising: a) providing: i) flosequinan, and ii) N-chlorosuccinimide; and b) reacting said flosequinan and N-chlorosuccinimide in an organic solvent under conditions such that monochloroflosequinan (3-chloromethylsulfinyl-7-fluoro-1-methyl-4-quinolone) is produced. A variety of solvents are contemplated. In some embodiments, said organic solvent is selected from the group consisting of carbon tetrachloride and benzene. In other embodiments, when said organic solvent is carbon tetrachloride, said reacting step b) additionally includes 2,2'-azobisisobutyronitrile.

In another embodiment, the present invention provides a method, comprising: a) providing: i) chlorodesoxyflosequinan (3-chloromethylthio-7-fluoro-1-methyl-4-quinolone), and ii) a camphor based reagent; and b) reacting said chlorodesoxyflosequinan and camphor based reagent in an organic solvent under conditions such that an enantiomer of monochloroflosequinan is produced in enantiomeric excess. In some embodiments said camphor based reagent is (R)-(−)-(10-camphorsulfonyl) oxaziridine. In such embodiments, said enantiomer of monochloroflosequinan is (S)-(+)-3-chloromethylsulfinyl-7-fluoro-1-methyl-4-quinolone. In yet other embodiments, said camphor based reagent is (S)-(+)-(10-camphorsulfonyl) oxaziridine. In such embodiments, said enantiomer of monochloroflosequinan is (R)-(−)-3-chloromethylsulfinyl-7-fluoro-1-methyl-4-quinolone.

In some embodiments, a one-step method of synthesis of 3-chloromethylsulfinyl-7-fluoro-1-methyl-4-quinolone is contemplated. The method comprises: a) providing: i) flosequinan, and ii) N-chlorosuccinimide; and b) reacting, in an organic solvent, said flosequinan with said N-chlorosuccinimide under conditions such that 3-chloromethylsulfinyl-7-fluoro-1-methyl-4-quinolone is produced. A variety of solvents are contemplated. In some embodiments, said organic solvent is selected from the group consisting of carbon tetrachloride and benzene. In embodiments wherein the solvent is carbon tetrachloride, the reaction additionally includes 2,2'-azobisisobutyronitrile (AIBN).

In other embodiments, a three-step method of synthesis of 3-chloromethylsulfinyl-7-fluoro-1-methyl-4-quinolone is contemplated. The method comprises: a) providing: i) racemic flosequinan, and ii) triphenyl phosphine; and b) reacting said racemic flosequinan and said triphenylphosphine in an organic solvent under conditions such that 7-fluoro-1-methyl-3-methylthio-4-quinolone is produced; and c) further reacting said 7-fluoro-1-methyl-3-methylthio-4-quinolone with N-chlorosuccinimide and 2,2'-azobisisobutyronitrile in an organic solvent under conditions such that 3-chloromethylthio-7-fluoro-1-methyl-4-quinolone is produced; and d) reacting said 3-chloromethylthio-7-fluoro-1-methyl-4-quinolone with hydrogen peroxide under conditions such that 3-chloromethylsulfinyl-7-fluoro-1-methyl-4-quinolone is produced. A variety of solvents are contemplated. In some embodiments, the solvent in step b) is carbon tetrachloride. In some embodiments, the solvent in step c) is carbon tetrachloride. In some embodiments, potassium carbonate is included in said reacting step d).

In other embodiments, alternative methods for the synthesis of 3-chloromethylthio-7-fluoro-1-methyl-4-quinolone are contemplated. In one embodiment, the method comprises: a) providing: i) racemic flosequinan, ii) thionyl chloride, and iii) pyridine; and b) reacting said racemic flosequinan, thionyl chloride and pyridine under conditions such that 3-chloromethylthio-7-fluoro-1-methyl-4-quinolone is produced.

In yet other embodiments, methods for the synthesis of the sulfone derivative of monochloroflosequinan are contemplated. In one embodiment, the method comprises: a) providing: i) monochloroflosequinan (3-chloromethylsulfinyl-7-fluoro-1-methyl-4-quinolone), and ii) m-chloroperoxybenzoic acid; and b) reacting said monochloroflosequinan and said m-chloroperoxybenzoic acid under conditions such that monochloroflosequinan sulfone (3-chloromethylsulfonyl-7-fluoro-1-methyl-4-quinolone) is produced.

In other embodiments, 3-chloromethylthio-7-fluoro-1-methyl-4-quinolone is used in stereopreferred oxidation reactions to produce (S)-(+)-3-chloromethylsulfinyl-7-fluoro-1-methyl-4-quinolone or (R)-(−)-3-chloromethylsulfinyl-7-fluoro-1-methyl-4-quinolone. The mixture of enantiomers produced may then be subjected to further separation procedures. In one embodiment, the 3-chloromethylthio-7-fluoro-1-methyl-4-quinolone used in the subsequent synthesis and separation of enantiomers of monochloroflosequinan is synthesized by a method comprising: a) providing: i) racemic flosequinan, ii) triphenylphosphine, and iii) a catalyst; and b) reacting, in a solvent, said racemic flosequinan and said triphenylphosphine in the presence of said catalyst under conditions such that 7-fluoro-1-methyl-3-methylthio-4-quinolone is produced; and c) further reacting said 7-fluoro-1-methyl-3-methylthio-4-quinolone in a solvent with N-chlorosuccinimide and 2,2'-azobisisobutyronitrile under conditions such that 3-chloromethylthio-7-fluoro-1-methyl-4-quinolone is produced. Again, a variety of solvents are contemplated. In some embodiments, said solvent in step b) is toluene and said catalyst is tetrabromomethane ($CBr_4$).

In some embodiments, the method further provides the synthesis of (R)-(−)-3-chloromethylsulfinyl-7-fluoro-1-methyl-4-quinolone. The method further comprises d) reacting said 3-chloromethylthio-7-fluoro-1-methyl-4-quinolone with (S)-(+)-(10-camphorsulfonyl)oxaziridine under conditions such that (R)-(−)-3-chloromethylsulfinyl-7-fluoro-1-methyl-4-quinolone is produced in enantiomeric excess.

In other embodiments, the method further provides the synthesis of (S)-(+)-3-chloromethylsulfinyl-7-fluoro-1-methyl-4-quinolone. The method further comprises d) reacting said 3-chloromethylthio-7-fluoro-1-methyl-4-quinolone with (R)-(−)-(10-camphorsulfonyl)oxaziridine under conditions such that (S)-(+)-3-chloromethylsulfinyl-7-fluoro-1-methyl-4-quinolone is produced in enantiomeric excess.

In some embodiments, racemic flosequinan is reacted with triphenyl phosphine and a catalyst in anhydrous xylene to produce 7-fluoro-1-methyl-3-methylthio-4-quinolone. In some embodiments, the catalyst is tetrabromomethane ($CBr_4$). Thus, in one embodiment, a method of synthesis of 7-fluoro-1-methyl-3-methylthio-4-quinolone is provided, comprising: a) providing: i) racemic flosequinan, ii) anhydrous xylene, iii) a catalyst, and iv) triphenyl phosphine; and b) reacting said racemic flosequinan and said triphenyl phosphine in said anhydrous xylene in the presence of said catalyst under conditions such that 7-fluoro-1-methyl-3-methylthio-4-quinolone is produced. In one embodiment, said catalyst is tetrabromomethane ($CBr_4$).

II. Synthesis of Dichloroflosequinan

In one embodiment the present invention teaches a dichloro heterocyclic compound corresponding to 3-dichloromethylsulfinyl-7-fluoro-1-methyl-4-quinolone (dichloroflosequinan) and derivative thereof.

In another embodiment, the present invention contemplates a method for the synthesis of 3-dichloromethylsulfinyl-7-fluoro-1-methyl-4-quinolone (dichloroflosequinan) comprising: a) providing, i) 3-dichloromethylthio-7-fluoro-1-methyl-4-quinolone, ii) dichloromethane (DCM), and iii) m-chloroperbenzoic acid (MCPBA); and b) reacting, i) 3-dichloromethylthio-7-fluoro-1-methyl-4-quinolone, ii) dichloromethane (DCM), and iii) m-chloroperbenzoic acid ("MCPBA") under conditions such that 3-dichloromethylsulfinyl-7-fluoro-1-methyl-4-quinolone is produced.

In another embodiment, the present invention contemplates a method for the synthesis of 3-dichloromethylsulfinyl-7-fluoro-1-methyl-4-quinolone (dichloroflosequinan) comprising: a) providing the compounds comprising i) thionyl chloride, ii) pyridine, iii) 3-chloromethylsulfinyl-7-fluoro-1-methyl-4-quinolone (mono-chloroflosequinan), iv) dichloromethane (DCM), and v) m-chloroperbenzoic acid ("MCPBA"); and b) reacting said i) thionyl chloride, ii) pyridine, iii) 3-chloromethylsulfinyl-7-fluoro-1-methyl-4-quinolone (mono-chloroflosequinan), iv) dichloromethane (DCM), and v) m-chloroperbenzoic acid ("MCPBA") under conditions such that 3-dichloromethylsulfinyl-7-fluoro-1-methyl-4-quinolone is produced.

III. Synthesis of Carboxyflosequinan

The present invention relates to compositions comprising carboxyflosequinan and the synthesis of the same.

In one embodiment, the present invention teaches a carboxylated heterocyclic compound corresponding to 3-carboxymethylsulfinyl-7-fluoro-1-methyl-4-quinolone (carboxyflosequinan) and derivatives thereof.

In one embodiment, the present invention teaches providing, 3-cyanomethylthio-7-fluoro-1-methyl-4-quinolone and a first acid followed by the reaction of said 3-cyanomethylthio-7-fluoro-1-methyl-4-quinolone and first acid under conditions such that 3-carboxymethylthio-7-fluoro-1-methyl-4-quinolone is produced.

In another embodiment the present invention further contemplates the reaction of 3-carboxymethylthio-7-fluoro-1-methyl-4-quinolone with a second acid and a peroxide under conditions such that 3-carboxymethylsulfinyl-7-fluoro-1-methyl-4-quinolone is produced.

IV. Synthesis of Fluoroflosequinan

In one embodiment, the present invention contemplates compositions comprising racemic monofluoroflosequinan (7-fluoro-3-fluoromethylsulfinyl-1-methyl-4-quinolone).

In one embodiments, the present invention contemplates compositions comprising difluoroflosequinan (3-difluoromethylsulfinyl-7-fluoro-1-methyl-4-quinolone). In another other embodiments, the present invention contemplates compositions comprising the sulfone derivative of difluoroflosequinan.

In one embodiment, the present invention contemplates methods for the synthesis of racemic monofluoroflosequinan. In one embodiment, the method comprises: a) providing: i) 7-fluoro-3-fluoromethylthio-1-methyl-4-quinolone and ii) m-chloroperbenzoic acid (MCPBA); and b) reacting said 7-fluoro-3-fluoromethylthio-1-methyl-4-quinolone and m-chloroperbenzoic acid in a solvent under conditions such that 7-fluoro-3-fluoromethylsulfinyl-1-methyl-4-quinolone is produced. In some embodiments, the solvent is dichloromethane (DCM). In another embodiment, a method of synthesis of 7-fluoro-3-fluoromethylthio-1-methyl-4-quinolone is contemplated. In one embodiment, the method comprises: a) providing: i) 7-fluoro-1-methyl-3-methylsulfinyl-4-quinolone (flosequinan), and ii) (diethylamino)sulfur trifluoride (DAST); and b) reacting said flosequinan and (diethylamino)sulfur trifluoride in a solvent under conditions such that 7-fluoro-3-fluoromethylthio-1-methyl-4-quinolone is produced. In some embodiments, the solvent is dichloromethane (DCM). In some embodiments, a catalyst is provided. The reaction time of step b) is reduced in the presence of the catalyst. In some embodiments, the catalyst is antimony chloride ($SbCl_3$).

In one embodiment, the present invention contemplates methods of synthesis of difluoroflosequinan (3-difluoromethylsulfinyl-7-fluoro-1-methyl-4-quinolone). In another embodiment, a second fluorine atom is introduced onto a side chain of 7-fluoro-3-fluoromethylthio-1-methyl-4-quinolone, to produce 3-difluoromethylthio-7-fluoro-1-methyl-4-quinolone, which is subsequently oxidized to produce 3-difluoromethylsulfinyl-7-fluoro-1-methyl-4-quinolone. In yet another embodiment, the method comprises: a) providing (i) 7-fluoro-3-fluoromethylthio-1-methyl-4-quinolone, (ii) SELECTFLUOR and (iii) triethylamine and b) reacting said 7-fluoro-3-fluoromethylthio-1-methyl-4-quinolone, SELECTFLUOR™ and triethylamine in a solvent under conditions such that 3-difluoromethylthio-7-fluoro-1-methyl-4-quinolone is produced and c) further reacting said 3-difluoromethylthio-7-fluoro-1-methyl-4-quinolone with m-chloroperbenzoic acid (MCPBA) in a solvent under conditions such that 3-difluoromethylsulfinyl-7-fluoro-1-methyl-4-quinolone is produced. In some embodiments, the solvent in step b) is acetronitrile. In some embodiments, the solvent in step c) is dichloromethane (DCM).

B. Treatment of Sexual Dysfunction with Halogenated Derivatives of Flosequinan and the Enantiomers of these Same Halogenated Flosequinan Derivatives.

In selected embodiments the present invention provides for the administration of halogenated heterocyclic compounds and the enantiomers of said halogenated heterocyclic compounds for the treament of sexual dysfunction in patients who are substantially free of symptoms of cardiac disease and who are not concurrently being treated with drugs which cause hypotensive effects (such as nitrites and nitrates). In one embodiment, the present invention provides for the administration of monochloroflosequinan for the treatment of sexual dysfunction in said patients. In a preferred embodiment, the present invention provides for the administration of the (+) enantiomer of monochloroflosequinan [e.g. (S)-(+)-3-chloromethylsulfinyl-7-fluoro-1-methyl-4-quinolone] for the treatment of sexual dysfunction in said patients. In another embodiment, said (+) enantiomer of monochloroflosequinan is substantially free of the (−) enantiomer of flosequinan.

In one embodiment, the present invention provides a method, comprising: a) providing: i) a patient suffering from at least one symptom of sexual dysfunction and, ii) a pharmaceutical composition comprising a substantially purified (+) enantiomer of monochloroflosequinan; and b) administering said pharmaceutical composition to said patient such that at least one symptom of sexual dysfunction is reduced.

A variety of such symptoms are contemplated, including but not limited to, poor blood flow to the sexual organs and/or failure to achieve orgasm. In one embodiment, the present invention contemplates administering monochloroflosequinan to said male or female under conditions such that blood flow to the sexual organs of said male or female is improved. In another embodiment, the present invention contemplates administering the (+) enantiomer of monochloroflosequinan to said male or female under conditions such that blood flow to the sexual organs of said male or female is improved.

It is not intended that the methods of the present invention be limited to a patient who is substantially free from cardiac disease. However, in one embodiment, the patient is substantially free from cardiac disease. In another embodiment, said patient is not free from cardiac disease. In one embodiment, the patient is male. In another embodiment, the patient is female. In one embodiment, said administering step is selected from the group consisting of intranasal and respiratory inhalation.

It is not intended that the methods of the present invention be limited to a patient who has been, or is being, treated with a drug that causes hypotensive effects. In one embodiment the present invention provides a method comprising, a) providing: i) a patient suffering from at least one symptom of sexual dysfunction who is not being treated with a drug that causes hypotensive effects and ii) a pharmaceutical composition comprising a purified (+) enantiomer of monochloroflosequinan, or a pharmaceutically acceptable salt thereof, and b) administering said pharmaceutical composition to said patient under conditions such that at least one symptom of sexual dysfuction is reduced.

A variety of such symptoms are contemplated, including but not limited to, poor blood flow to the sexual organs and/or failure to achieve orgasm. In one embodiment, the present invention contemplates administering monochloroflosequinan to a male or female under conditions such that blood flow to the sexual organs of said male or female is improved. In another embodiment, the present invention contemplates administering the (+) enantiomer of monochloroflosequinan to a male or female under conditions such that blood flow to the sexual organs of said male or female is improved.

It is not intended that the methods of the present invention be limited to a patient who is being, or has been, treated with a nitrate or nitrite. However, in another embodiment, the method comprises a) providing: i) a patient (either male or female) suffering from at least one symptom of sexual dysfunction (and who is not being concurrently treated with a nitrite or nitrate) and ii) a pharmaceutical composition comprising a monochloroflosequinan and b) administering said monochloroflosequinan to said patient under conditions such that at least one symptom of sexual dysfunction is reduced.

A variety of such symptoms are contemplated, including but not limited to, poor blood flow to the sexual organs and/or failure to achieve orgasm. In one embodiment, the present invention contemplates administering said monochloroflosequinan to said male or female under conditions such that blood flow to the sexual organs of said male or female is improved. In one embodiment, said patient is substantially free from cardiac disease. In another embodiment, said administering step is selected from the group consisting of intranasal and respiratory inhalation. In yet another embodiment, said patient is not concurrently being treated with a nitrite or nitrate (for example glycerol reinitiate, isosorbide dinitrate, isosorbide-5'-mononitrate, and erythrityl tetranitrate).

In one embodiment the present invention provides a method comprising: a) providing, i) a male or female subject with erectile dysfunction and ii) monochloroflosequinan (or a pharmaceutically acceptable salt thereof) and b) introducing said monochloroflosequinan to said male or female subject such that an erection (i.e. penile or clitoral) is produced. In another embodiment, the present invention provides a method comprising: a) providing, i) a male or female subject with erectile dysfunction and ii) the (+) enantiomer of monochloroflosequinan (or a pharmaceutically acceptable salt thereof) and; b) introducing said (+) enantiomer of monochloroflosequinan to said male or female subject such that an erection (i.e. penile or clitoral) is produced.

It is not intended that the present invention be limited by the method of introduction of the halogenated derivatives of flosequinan and the enantiomers of halogenated flosequinan derivatives. In one embodiment, monochloroflosequinan is introduced into the male or female orally. In one embodiment, approximately 200 milligrams of racemic monochloroflosequinan is administered in an oral dosage form.

In one embodiment, the present invention contemplates the administration of a single dose per day of approximately two hundred milligrams of the (+) enantiomer of monochloroflosequinan to an adult human male or female. In another embodiment this single daily dose of the (+) enantiomer of monochloroflosequinan is between approximately fifty to approximately seventy-five milligrams. In another embodiment this single daily dose of the (+) enantiomer of monochloroflosequinan is between approximately twenty to approximately fifty milligrams per day. In a preferred embodiment this single daily dose of the (+) enantiomer of monochloroflosequinan is between approximately ten to approximately twenty milligrams per day.

The present invention also contemplates the administration of multiple dosages the halogenated derivates of flosequinan (and the sulfone of halogenated flosequinan derivatives) including, but not limited to, the administration of multiple dosages of the (+) enantiomer of monochloroflosequinan.

In other embodiments the halogenated derivates of flosequinan (and the sulfone of halogenated flosequinan derivatives) described by the present invention are introduced cutaneously, transurethrally, by standard injection, intracavernosally, intranasally or through respiratory inhalation.

Furthermore, the methods of the present invention are not limited by the degree of response in a male or female subject. In one embodiment, a penile erection is induced sufficient for vaginal penetration. In another embodiment, the clitoris becomes tumescent to some degree.

Likewise, the present invention also contemplates the use of sexual stimulation in addition to the application of a pharmaceutical composition.

In another embodiment the present invention contemplates, a) providing: i) a male, having a penis, with erectile dysfunction, ii) a halogenated derivates of flosequinan, and iii) sexual stimulation; and b) introducing said enantiomer of flosequinan, a derivative of flosequinan or monochloroflosequinan and sexual stimulation to the male such that an erection is produced.

In another embodiment the present invention contemplates, a) providing: i) a male, having a penis, with erectile dysfunction, ii) monochloroflosequinan, or a pharmaceutically acceptable salt thereof, and iii) sexual stimulation; and b) introducing said enantiomer of flosequinan, a derivative of flosequinan or monochloroflosequinan and sexual stimulation to the male such that an erection is produced.

In another embodiment, the method comprises a) providing: i) a male, having a penis, with erectile dysfunction, ii) a halogenated derivates of flosequinan, and iii) sexual stimulation; and b) introducing said pharmaceutical composition and sexual stimulation to the male such that an erection is produced.

In another embodiment, the method comprises a) providing: i) a male, having a penis, with erectile dysfunction, ii) monochloroflosequinan, and iii) sexual stimulation; and b) introducing said pharmaceutical composition and sexual stimulation to the male such that an erection is produced.

In another embodiment, the present invention also contemplates the use of sexual stimulation in addition to the application of a pharmaceutical composition. For example, one embodiment comprises a) providing: i) a female, having a clitoris, with erectile dysfunction, ii) a halogenated derivates of flosequinan, and iii) sexual stimulation; and b) introducing said flosequinan and sexual stimulation to the female such that an erection is produced.

In another embodiment, the method comprises a) providing: i) a female, having a clitoris, with erectile dysfunction, ii) monochloroflosequinan, and iii) sexual stimulation; and b) introducing said pharmaceutical composition and sexual stimulation to the female such that an erection is produced.

Likewise, the present invention is not limited by the nature of the sexual stimulation. In one embodiment, the sexual stimulation is sexually explicit media. In another embodiment, the sexual stimulation involves manipulation of the penis, such as with vibration. In another embodiment, the sexual stimulation involves manipulation of the clitoris, such as with vibration or digital stimulation.

It is not intended that the present invention be limited by the nature of the formulation. In selected embodiments, the present invention contemplates the formulation of racemic monochloroflosequinan, the enantiomers of monochloroflosequinan, dichloroflosequinan, monofluoroflosequinan, difluoroflosequinan and/or carboxyflosequinan as a therapeutic for the treatment of sexual dysfunction in males and females. In other embodiments the present invention contemplates the formulation of the sulfone of monochloroflosequinan, dichloroflosequinan, monofluoroflosequinan, and difluoroflosequinan as a therapeutic for the treatment of sexual dysfunction in males and females. In a preferred embodiment, the present invention describes the formulation of the (+) enantiomer of monochloroflosequinan [e.g. (S)-(+)-3-chloromethylsulfinyl-7-fluoro-1-methyl-4-quinolone] as a therapeutic for the treatment of sexual dysfunction in males and females.

C. Treatment of Cardiovascular Disease with Halogenated Derivatives of Flosequinan and the Enantiomers of these Same Halogenated Flosequinan Derivatives.

In selected embodiments the present invention contemplates the administration of halogenated derivatives of flosequinan (and the enantiomers of said halogenated derivates of flosequinan) for the treatment of cardiovascular disease. These halogenated flosequinan derivatives (and the enantiomers of said halogenated derivates of flosequinan) include (but are not limited to) racemic monochloroflosequinan, the (+) enantiomer of monochloroflosequinan, the (−) enantiomer of monochloroflosequinan, carboxyflosequinan, dichloroflosequinan, monofluoroflosequinan, and difluoroflosequinan. In other embodiments the present invention also contemplates the administration of the sulfone of monochloroflosequinan, dichloroflosequinan, monofluoroflosequinan, and/or difluoroflosequinan as a therapeutic for the treatment of cardiovascular disease. In selected embodiments the present invention contemplates the administration of these halogenated flosequinan derivatives, enantiomers, and sulfones to subjects who are not concurrently administered nitrites and nitrates.

In one embodiment, the present invention contemplates a method, comprising: a) providing: i) a patient presenting at least one symptom of cardiovascular disease, and ii) a halogenated derivative of flosequinan; and b) administering said preparation to said patient (e.g. such that said symptom is reduced). A variety of such symptoms of cardiovascular disease are contemplated. It is not intended that the present invention be limited to the reduction of a particular symptom of cardiovascular disease. In a preferred embodiment, the a symptom of hypertension is reduced.

Hypertension is an abnormal increase of blood pressure in the arteries continuing over a period of time. It occurs when the arterioles, the small blood vessels that branch off from the arteries, become constricted. This constriction of the arterioles makes it difficult for blood to flow which increases pressure against the artery walls.

A blood pressure reading of approximately 110/60 to 140/90 is considered to be in the normal range. The first number (110) is the systolic pressure which measures the blood pressure in the arteries when the heart is contracting and pumping blood. The second number (60) is the diastolic pressure which measures the blood pressure in the arteries when the heart is at rest. Hypertension adds to the workload of the heart and arteries. Over time, this can lead to heart and blood vessel damage which causes hardening of the arteries, heart failure, stroke, kidneys problems, blindness, and brain damage. In one embodiment of the present invention, a symptom of cardiovascular disease comprises a measured blood pressure of approximately 140/90 or higher. In a preferred embodiment, the diagnosis of said hypertensive blood pressure (e.g. approximately 140/90 or higher) is confirmed by a plurality of measurements of approximately 140/90 or higher spaced over the period of at least two weeks. It is not intended that the present invention be limited by the means by which blood pressure is measured. Moreover, additional symptoms of hypertension also include, but are not limited to, tiredness, confusion, nausea, vomiting, anxiety, excessive perspiration, muscle tremor, chest pain, nosebleed, and buzzing in the ears.

In another embodiment, the present invention contemplates compositions and methods to reduce the symptoms of CHF (also referred to as 'heart failure'). CHF is characterized by an inadequacy of the heart so that, as a pump, it fails to maintain the circulation of blood, such that congestion and edema develop in the tissues of the heart are reduced. Symptoms of CHF include, but are not limited to, shortness of breath, pitting edema, an enlarged and tender liver, engorged neck veins, and pulmonary rales in various combinations.

It is not intended that the present invention be limited by the method by which CHF is diagnosed. CHF may be diagnosed based on a medical history and complete physical examination, which may include a blood pressure check, listening to the subject's heart through a stethoscope and taking the subject's pulse. At physical exam a Health Care Provider (including, but not limited to, Physicians, Nurse Practitioners, or Physician's Assistants) may look for the symptoms of CHF (as listed above).

If a Health Care Provider does not find enough symptoms to make a diagnosis, but is still suspicious that the subject has CHF, then her or she may order further tests. These test include, but are not limited to, blood tests to assess for anemia and thyroid function, urine tests to measure sugar, an Electrocardiogram (EKG), an exercise stress test, an Echocardiogram, a stress echocardiogram, radionuclide imaging tests (such as a radionuclide ventriculogram).

More invasive exploratory tests may also be ordered in conjunction with, or instead of the above. These tests include a coronary angiogram, in which a contrast dye is delivered by catheter to the coronary arteries to visualize the blood vessels and identify heart damage or dysfunction.

The present invention is not limited by the degree of response by the subject. It is expected that the administration of a halogenated derivative of flosequinan will reduce the symptoms associated with cardiovascular diseases including, but not limited to, angina pectoris, myocardial infarction, congestive heart failure, cardiomyopathy, hypertension, arterial stenosis, and venous stenosis. In a preferred embodiment, halogenated derivatives of flosequinan are administered to reduce the symptoms associated with hypertension.

In another embodiment, a halogenated derivative of flosequinan is administered to reduce the symptoms of CHF. The symptoms of CHF include, but are not limited to, shortness of breath, pitting edema, an enlarged and tender liver, engorged neck veins, and pulmonary rales in various combinations.

Symptoms are "reduced" when the magnitude (e.g. intensity) or frequency of symptoms is reduced. It is not intended that the present invention be limited only to cases where the symptoms are eliminated. The present invention specifically contemplates treatment such that symptoms are reduced (and the condition of the subject is thereby "improved"), albeit not completely eliminated. Moreover, it is sufficient if one or more (e.g., a subset) of symptoms are reduced.

While it is not intended that the present invention be limited by any specific dosage or dosage form, in one embodiment, it is contemplated that a human subject will be given a single oral dosage (per day) of approximately 200 milligrams of a halogenated derivative of flosequinan. In another embodiment said dosage is between approximately twenty-five to approximately seventy-five milligrams. In another embodiment, said dosage is between approximately one hundred and twenty-five and approximately two hundred milligrams.

In another embodiment, the administration of said halogenated derivative of flosequinan comprises three daily doses, before meals, each dose of up to approximately two hundred milligrams per dose. In another embodiment, said daily doses comprise between approximately twenty-five to approximately seventy-five milligrams per dose. In another embodiment, said daily doses comprise between approximately one hundred and twenty-five and approximately two hundred milligrams per dose.

In selected embodiments said halogenated derivative of flosequinan is introduced orally, cutaneously, by standard injection (e.g. intravenously), or intranasally.

In one embodiment, the method comprises a) providing: i) a patient suffering from symptoms of cardiac disease who is not being administered nitrates or nitrites; and ii) a halogenated derivative of flosequinan; and b) introducing said halogenated derivative of flosequinan to said patient such that said symptoms of cardiac disease are reduced.

In one embodiment, the method comprises a) providing: i) a subject suffering from symptoms of cardiovascular disease; and ii) a halogenated derivative of flosequinan or a pharmaceutically acceptable salt thereof; and b) administering said halogenated derivative of flosequinan to the subject such that symptoms are reduced. In one embodiment, said cardiovascular disease is selected from the group consisting of hypertension, angina pectoris, myocardial infarction, and congestive heart failure. Said administering step is selected from the routes consisting of intranasal and respiratory inhalation.

In another embodiment, the method comprises a) providing: i) a subject suffering from symptoms of cardiovascular disease who is not being treated with a drug that causes hypotensive effects, and ii) a halogenated derivative of flosequinan, or a pharmaceutically acceptable salt thereof; and b) administering said halogenated derivative of flosequinan to the subject such that such symptoms are reduced.

In another embodiment, the method comprises a) providing: i) a subject suffering from symptoms of cardiovascular disease who is not being treated with a nitrite or nitrate, and ii) a halogenated derivative of flosequinan, or a pharmaceutically acceptable salt thereof; and b) introducing said halogenated derivative of flosequinan to the subject such that said symptoms are reduced. Said nitrate is selected from the group consisting of glyceryl trinitrate, isosorbide dinitrate, isosorbide-5'-mononitrate, and erythrityl tetranitrate.

It is not intended that the present invention be limited by the method of introduction of a halogenated derivative of flosequinan, or a pharmaceutically acceptable salt thereof. In one embodiment, said halogenated derivative of flosequinan is introduced orally. In one embodiment, an adult human is provided an oral dosage, as a single dose per day, in the range between 10 to 200 milligrams of a halogenated derivative of flosequinan. In other embodiment, a halogenated derivative of flosequinan is introduced cutaneously, by standard injection, intranasally, or through respiratory inhalation.

The present invention is not limited by the degree of response by the subject. In one embodiment, relief of pain from angina pectoris is sufficient.

It is not intended that the present invention be limited by the nature of the formulation. In one embodiment, the present invention contemplates a mixture of a halogenated derivative of flosequinan and a carrier, i.e. a mixture comprising lactose.

In one embodiment, the halogenated derivative of flosequinan recited in the present invention are introduced into a subject by oral administration or cutaneous administration. In another embodiment, said subject is an adult human and said oral administration comprises up to approximately 200 milligrams of a halogenated derivative of flosequinan.

In some embodiments any of the halogenated derivatives of flosequinan, recited in the present invention, are administered to a subject who is not being concurrently treated with a nitrite or nitrate. In one embodiment said nitrate is selected from the group consisting of glyceryl trinitrate, isosorbide dinitrate, isosorbide-5-mononitrate and erythrityl tetranitrate.

The present invention also contemplates a method, comprising: a) providing: i) a subject suffering from a symptom of a cardiovascular disease selected from the group of hypertension and congestive heart failure and; ii) a halogenated derivative of flosequinan and; b) administering said halogenated derivative of flosequinan to said subject under conditions such that said symptom is reduced. In one embodiment, the halogenated derivative of flosequinan is introduced into said subject by oral or cutaneous administration. In one embodiment said subject is an adult human and said oral administration comprises up to approximately 200 milligrams of said halogenated derivative of flosequinan.

DESCRIPTION OF THE DRAWINGS

FIG. 14 depicts the results of in vitro phosphodiesterase inhibition assays using monochloroflosequinan sulfone.

FIG. 16A and FIG. 16B depict the results of in vitro phosphodiesterase inhibition assays using monochloroflosequinan.

FIG. 22A and FIG. 22B depict the results of in vitro PDE enzyme inhibition assays using dichloroflosequinan.

FIG. 29 depicts the results of enzyme (PKC) inhibition assays with 3-carboxymethylsulfinyl-7-fluoro-1-methyl-4-quinolone.

FIG. 32 depicts the chemical synthesis of 7-fluoro-3-fluoromethylthio-1-methyl-4-quinolone in the presence of a catalyst (Antimony chloride).

FIG. 34A and FIG. 34B depict the results of enzyme inhibition and radioligand binding assays with monofluoroflosequinan.

DEFINITIONS

Figure 1:
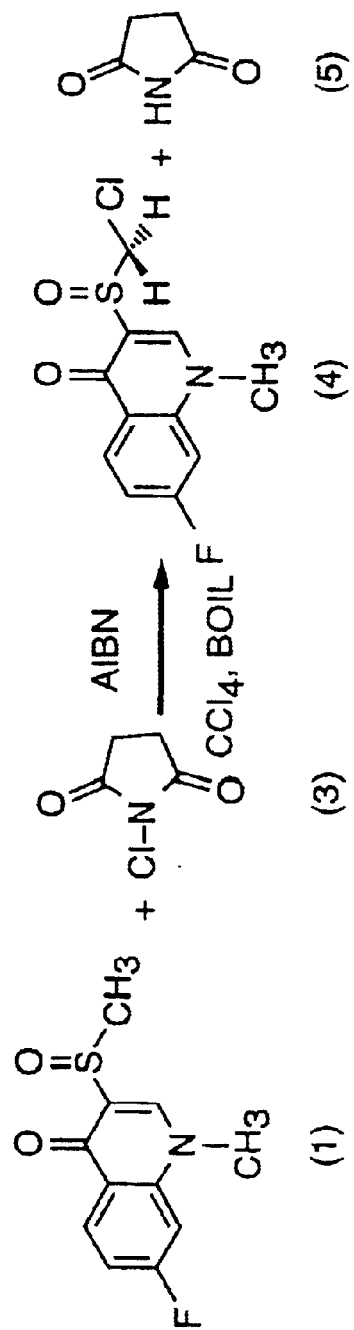
FIG. 1 depicts a one-step chemical synthesis of racemic monochloroflosequinan. Racemic flosequinan is chlorinated as described to produce monochloroflosequinan.

As used herein, "R and S" are used to denote the absolute configuration of the molecule about its chiral center(s).

As used herein, the prefixes "(+) and (−)" are employed to designate the sign of rotation of plane-polarized light by the compound, with (−) meaning that the compound is levorotatory (rotates to the left). A compound prefixed with (+) is dextrorotatory (rotates to the right).

As used herein, the terms "enantiomer" or "enantiomeric isomer" refer to stereoisomers of molecules that are non-superimposable mirror images of each other. Enantiomers have identical physical properties, such as melting points and boiling points, and also have identical spectroscopic properties. Enantiomers differ from each other with respect to their interaction with plane-polarized light and with respect to biological activity.

As used herein, the term "stereoisomer" refers to compounds that have their atoms connected in the same order but differ in the arrangement of their atoms in space. (e.g. L-alanine and D-alanine).

As used herein, the terms "racemic", "racemic mixture", or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

As used herein, the phrase "enantiomeric excess" or "e.e." refers to a reaction product wherein one enantiomer is produced in excess of the other and the percentage of the excess enantiomer is calculated using either (or both) of the following algorithms:

Algorithm No. 1: enantiomeric excess=(specific rotation of the reaction product/specific rotation of the pure enantiomer in excess)×100.

Algorithm No. 2: enantiomeric excess=[(moles of major enantiomer−moles of other enantiomer/total moles of both enantiomers)]×100.

As an example (the values in this example are offered for illustration only and do not represent data subsequently expressed in the "Experimental" section of this application), the observed rotation of a reaction product +8.52 degrees of rotation and the specific rotation of the R-configured enantiomer is reported as +15.00 degrees of rotation. The sign of the specific rotation of the reaction product indicates which enantiomer is in excess (e.g. in this example the R-configured isomer is in excess). If these values are inserted into Algorithm No. 1, the enantiomeric excess=(+8.52/+15.00)(100)=56.8% in excess of the R-isomer.

As used herein, the terms "purified enantiomer" and "purified enantiomer preparation" are meant to indicate a preparation (e.g. derived from non-optically active starting material, substrates or intermediates) wherein one enantiomer (for example, the (+) enantiomer) is enriched over the other, and more preferably, wherein the other enantiomer (for example the (−) enantiomer) represents less than 20%, more preferably less than 10% [e.g. in this particular instance, the (+) enantiomer is substantially free of the (−) enantiomer], and more preferably less than 5% and still more preferably, less than 2% of the preparation. A purified enantiomer may be synthesized substantially free of the other enantiomer, or a purified enantiomer may be synthesized in a stereopreferred procedure, followed by separation steps, or a purified enantiomer may be derived from a racemic mixture.

Whether expressed as a "purified enantiomer" or "a compound in enantiomeric excess", the terms are meant to indicate that the amount of one enantiomer exceeds the amount of the other. Thus, when referring to an enantiomer preparation, both (or either of) the percent of the major enantiomer (e.g. by weight) and (or) the percent enantiomeric excess of the major enantiomer may be used to determine whether the preparation represents a purified enantiomer preparation.

As used herein, the term "optical purity" refers to the ratio of the observed optical rotation of a sample consisting of a mixture of enantiomers to the optical rotation of one pure enantiomer.

As used herein, the term "camphor based reagent" refers to a reagent (or reagents) comprising a camphor moiety, as shown below:

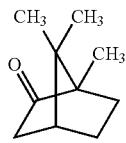

Camphor based reagents include, but are not limited to the following:
(R)-(−)-(10-camphorsulfonyl)oxaziridine:

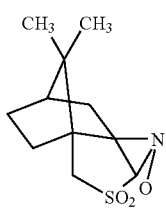

(S)-(+)-(10-camphorsulfonyl)oxaziridine:

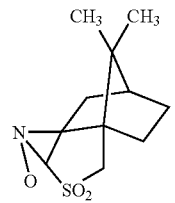

and (−)-(8,8-dichlorocamphorylsulfonyl)oxaziridine:

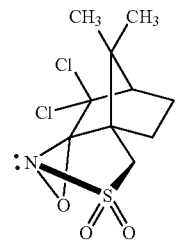

As used herein, the phrase "flosequinan" refers to 7-fluoro-1-methyl-3-(methylsulphinyl)-4(1H)-quinolinone which may also be described as 7-fluoro-1-methyl-3-(methylsulfinyl)-4(1H)-quinolone) and as 7-fluoro-1-methyl-3-methylsulfinyl-4-quinolone having the chemical structure of:

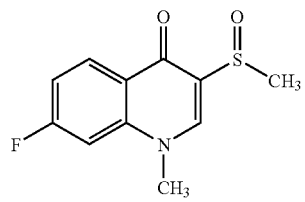

As used herein, the phrase "racemic flosequinan" or "flosequinan racemate" refers to a mixture of the two enantiomers of flosequinan. An ideal racemic mixture of the enantiomers of flosequinan refers to a 1:1 mixture of the S-(−)- and R-(+)-enantiomers of flosequinan, such that the optical rotation of the (+)-enantiomer cancels out the optical rotation of the (−)-enantiomer.

As used herein, "desoxyflosequinan" refers to 7-fluoro-1-methyl-3-methylthio-4-quinolone having the chemical structure of:

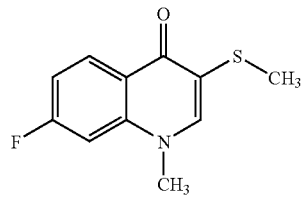

As used herein, "monochloroflosequinan" refers to the chemical composition designated as 3-chloromethylsulfinyl-7-fluoro-1-methyl-4-quinolone having the chemical structure corresponding to:

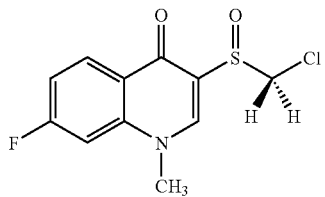

As used herein, the phrase "racemic monochloroflosequinan" or "monochloroflosequinan racemate" refers to a mixture of the two enantiomers of monochloroflosequinan. An ideal racemic mixture of the enantiomers of monochloroflosequinan refers to a 1:1 mixture of the (+)- and (−)-enantiomers of monochloroflosequinan, such that the optical rotation of the (+)-enantiomer cancels out the optical rotation of the (−)-enantiomer.

As used herein, "chlorodesoxyflosequinan" refers to the chemical composition designated as 3-chloromethylthio-7-fluoro-1-methyl-4-quinolone having the chemical structure corresponding to:

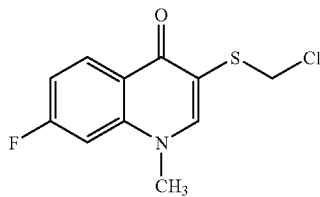

As used herein the "sulfone derivative of monochloroflosequinan" or "monochloroflosequinan sulfone" refers to the chemical composition designated as 3-chloromethylsulfonyl-7-fluoro-1-methyl-4-quinolone having the chemical structure corresponding to:

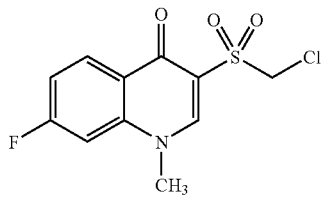

As used herein, the "(+)-enantiomer of monochloroflosequinan" or "(S)-(+)-monochloroflosequinan" refers to the chemical composition designated as (+)-3-chloromethylsulfinyl-7-fluoro-1-methyl-4-quinolone or (S)-(+)-3-chloromethylsulfinyl-7-fluoro-1-methyl-4-quinolone having the structure corresponding to:

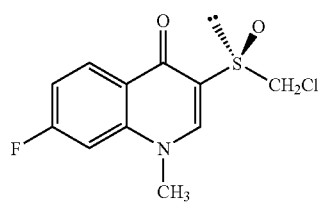

As used herein, the "(−)-enantiomer of monochloroflosequinan" or "(R)-(−)-monochloroflosequinan" refers to the chemical composition designated as (−)-3-chloromethylsulfinyl-7-fluoro-1-methyl-4-quinolone or (R)-(−)-3-chloromethylsulfinyl-7-fluoro-1-methyl-4-quinolone having the structure corresponding to:

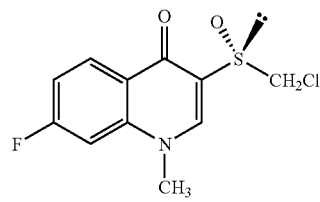

As used herein, a "derivative of flosequinan" refers to any halogenated, nonhalogenated derivative of flosequinan or an enantiomer of any halogenated, nonhalogenated derivative of flosequinan.

As used herein the terms, "halogenated derivative of flosequinan" and "halogenated flosequinan derivative" refers to a composition comprising flosequinan with the addition of one or more halogen atom(s) [for example fluorine, chlorine, and/or bromine] at any position within a molecule of flosequinan. Halogenated derivatives of flosequinan may, or may not be, optically active and, therefore, may or may not exist as enantiomers.

As used herein, the phrase "methylsulphinyl derivatives of quinolinone" refers to chemical compositions comprising quinolinone with a methylsulphinyl group attached. Examples include flosequinan (7-fluoro-1-methyl-3-(methylsulphinyl)-4(1H)-quinolone; 7-fluoro-1-methyl-3-(methylsufinyl)-4(1H)-quinolinone):

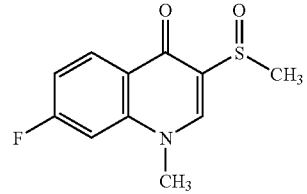

and sulfone metabolites of flosequinan:

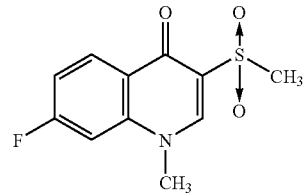

As used herein, "room temperature", "RT" or "ambient temperature" is approximately 18° C. to 21° C.

As used herein, "overnight" is approximately 8 hours, more preferably 12 hours, more typically 17 hours, but can be up to approximately 30 hours.

As used herein, the term "heterocyclic compound" refers to a compound comprising a ring composed of atoms of more than one kind.

As used herein, "optical activity" refers to the property of certain substances to rotate plane polarized light. A compound or mixture of compounds which is "optically inactive" produces no net rotation of plane polarized light.

As used herein, a "catalyst" refers to a substance that, when added to a reaction mixture, changes (e.g. speeds up) the rate of attainment of equilibrium in the system without itself undergoing a permanent chemical change. Examples of suitable catalysts contemplated for use in the present invention include, but are not limited to, tetrabromomethane (CBr$_4$), carbon tetraiodide and iodide.

As used herein, an "organic solvent" refers to an organic substance that will dissolve other substances. Examples of organic solvents suitable for use in embodiments of the present invention include, but are not limited to carbon tetrachloride (CCl$_4$), xylene, toluene, benzene and methylene dichloride.

As used herein, the term "IBMX" corresponds to the structure having the chemical formula: 3-isobutyl-1-methylxanthine (available from Sigma).

As used herein, the phrases "pharmaceutical composition" and "therapeutic preparation" refer to any composition comprising an active compound or drug [for example, but not limited to, monochloroflosequinan] formulated substances comprising substantially physiologically acceptable solution(s) [for example, but not limited, to saline] and/or fillers [for example, but not limited, cellulose]. Pharmaceutical composition and therapeutic preparation may or may not also contain: i) pH modulating reagents and/or ii) preservatives.

As used herein, the phrase "pharmaceutically acceptable salts" or "a pharmaceutically acceptable salt thereof" refer to salts prepared from pharmaceutically acceptable non-toxic acids or bases including inorganic acids and bases and organic acids and bases. Since the compound of the present invention is basic, salts may be prepared from pharmaceutically acceptable non-toxic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Preferred acid addition salts are the chloride and sulfate salts.

As used herein, a patient who is "substantially free from cardiac disease" and a patient who is "substantially free from symptoms of cardiac disease" indicate that the patient has not been diagnosed with angina, myocardial infarction, congestive heart failure and that symptoms of angina, ischemia, myocardial infarction, and/or congestive heart failure have not been detected.

As used herein, "drugs that have hypotensive effects" are those drugs which, when administered, cause the patient's end-diastolic blood pressure to be reduced. Nitrates are commonly used drugs which have hypotensive effects.

As used herein, "nitrates" are compounds that contain the —NO$_3$— moiety. Nitrates typically used in the clinic are shown in Table 1.

As used herein, "nitrites" are compounds that contain the —NO$_2$— moiety. Nitrites typically used in the clinic are shown in Table 1.

As used herein, the term "erectile dysfunction" refers to certain disorders of the cavernous tissue of the penis and the associated facia which produce impotence, the inability to attain a sexually functional erection. In the female "erectile dysfunction" is associated with disorders (including but not limited to impaired blood flow to the clitoris) which impair or prevent the clitoris from becoming tumescent in response to any form of sexual stimulation.

As used herein, "symptoms of erectile dysfunction" refers to any of the following symptoms: penile flaccidity, lack of penile tumescence, lack of penile rigidity, and inability to produce an erection sufficient for vaginal penetration. Symptoms are "reduced" when the magnitude (e.g. intensity) or frequency of symptoms is reduced. It is not intended that the present invention be limited only to cases where the symptoms are eliminated. The present invention specifically contemplates treatment such that symptoms are reduced (and the condition of the patient is thereby "improved"), albeit not completely eliminated.

| NONPROPRIETARY NAMES AND TRADE NAMES | CHEMICAL STRUCTURE | PREPARATIONS, USUAL DOSES, AND ROUTES OF ADMINISTRATION* |
|---|---|---|
| Amyl nitrite (isoamyl nitrite) | (H$_3$C)$_2$CHCH$_2$CH$_2$ONO | Inh: 0.18 or 0.3 ml, inhalation |
| Nitroglycerin (glyceryl trinitrate; NITRO-BID, NITROSTAT, NITROL, NITRO-DUR, others) | H$_2$C—O—NO$_2$<br>HC—O—NO$_2$<br>H$_2$C—O—NO$_2$ | T: 0.15 to 0.6 mg as needed<br>S: 0.4 mg per spray as needed<br>C: 2.5 to 9 mg two to four times daily<br>B: 1 mg every 3 to 5 h<br>O: 1.25 to 5 cm (½ to 2 in.), topically to skin every 4 to 8 h<br>D: 1 disc (2.5 to 15 mg) every 24 h<br>IV: 5 µg/min; increments of 5 µg/min |
| Isosorbide dinitrate (ISORDIL, SORBITRATE, DILATRATE, others) | (bicyclic structure with HC—O—NO$_2$ and O$_2$N—O—CH) | T: 2.5 to 10 mg every 2 to 3 h<br>T(C): 5 to 10 mg every 2 to 3 h<br>T(O): 10 to 40 mg every 6 h<br>O C: 40 to 80 mg every 8 to 12 h |

| NONPROPRIETARY NAMES AND TRADE NAMES | CHEMICAL STRUCTURE | PREPARATIONS, USUAL DOSES, AND ROUTES OF ADMINISTRATION* |
|---|---|---|
| Isosorbide-5-mononitrate (IMDUR, ISMO, others) | 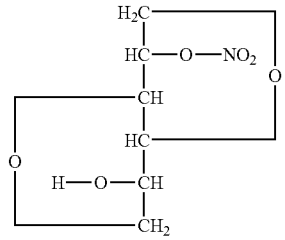 | T: 10 to 40 mg twice daily<br>C: 60 mg daily |
| Erythrityl tetranitrate (CARDILATE) | 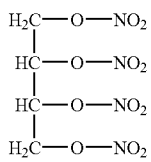 | T: 5 to 10 mg as needed<br>T(O): 10 mg three times daily |

B, buccal (transmucosal) tablet; C, sustained-release capsule or tablet; D, transdermal disc; Inh, inhalant; IV intravenous injection; O, ointment; S, lingual spray; T, tablet for sublingual use; T(C), chewable tablet; T(O), oral tablet or capsule.

As used herein, "symptoms of sexual dysfunction" includes, but is not limited to, poor blood flow to the sexual organs and/or failure to achieve orgasm. Symptoms are "reduced" when the magnitude (e.g. intensity) or frequency of symptoms is reduced. It is not intended that the present invention be limited only to cases where the symptoms are eliminated. The present invention specifically contemplates treatment such that symptoms are reduced (and the condition of the patient is thereby "improved"), albeit not completely eliminated.

As used herein "standard injection" refers to the placement of a pharmaceutical composition into a subject (e.g., with a hypodermic needle). For example, such injection can be made subcutaneously, intravenously, intramuscularly, intracavernosally, etc.

As used herein, "intracavernosal" injection is injection into the corpus cavernosum of the penis.

As used herein, an "erection" refers to the condition of a penis whereby it is at least semi-rigid as opposed to being in a flaccid state.

As used herein, "by oral administration" refers to the introduction of a pharmaceutical composition into a subject by way of the oral cavity (e.g., in aqueous liquid or solid form).

As used herein, "cutaneously" refers to the introduction of a pharmaceutical composition into a subject by application to the surface of the skin such that the composition is absorbed into the subject.

As used herein, "transurethrally" refers to the introduction of a pharmaceutical composition to the urethra of a subject such that the composition is absorbed into the subject.

As used herein, "intranasally" refers to the introduction of a pharmaceutical composition within the nasal cavity.

As used herein, "respiratory inhalation" refers to the introduction of a pharmaceutical composition within the respiratory tract.

As used herein, "sufficient for vaginal penetration" refers to the state of an erection such that the penis is capable of entering a vagina without manual manipulation.

As used herein, "sexual stimulation" refers to activity that would induce an erection in a male without erectile dysfunction (e.g., sexually explicit media, manual manipulation, vibration, live erotic entertainment, etc.). In the female, "sexual stimulation" refers to activity (e.g., sexually explicit media, manual manipulation, vibration, live erotic entertainment, etc.) that would induce a sexual response in females without sexual dysfunction. Examples of female sexual response include, but are not limited to, increased vaginal lubrication and increased tumescence of the clitoris.

As used herein, "sexually explicit media" refers to films, videos, books, magazines, etc. that depict sexual activity.

As used herein "single dosage" refers to a pharmaceutical composition of a formulation that is capable of achieving its intended effect in a single administration or application.

As used herein carboxyflosequinan refers to the chemical composition designated as 3-carboxymethylsufinyl-7-fluoro-3-methyl-4-quinolone having the chemical structure corresponding to:

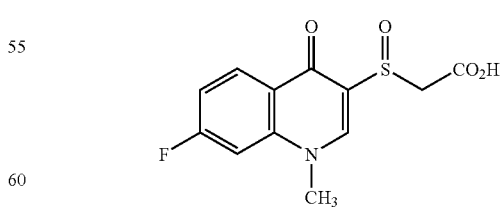

As used herein monofluoroflosequinan refers to the chemical composition designated as 7-fluoro-3-fluoromethylsulfinyl-1-methyl-4-quinolone having the chemical structure corresponding to the structure depicted below:

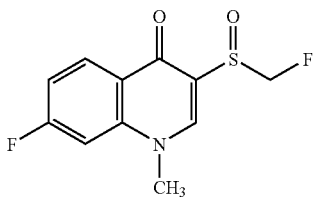

As used herein, "difluoroflosequinan" refers to the chemical composition designated as 3-difluoromethylsulfinyl-7-fluoro-1-methyl-4-quinolone having the chemical structure corresponding to:

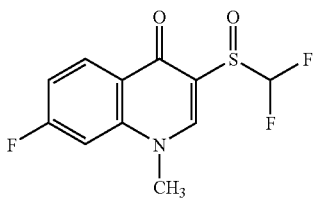

As used herein, the "sulfone derivative of difluoroflosequinan" refers to the chemical composition designated as 3-difluoromethylsulfonyl-7-fluoro-1-methyl-4-quinolone having the chemical structure corresponding to:

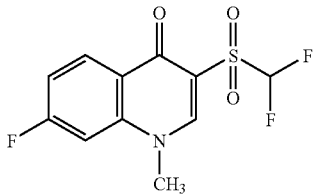

As used herein, "symptoms of cardiovascular disease" refers to any clinical manifestation of a disease state associated with the heart and vasculature. For example, said clinical manifestation include: angina pectoris, myocardial infarction, congestive heart failure, cardiomyopathy, hypertension, arterial stenosis, and venous stenosis. The present invention specifically contemplates treatment such that symptoms are reduced (and the condition of the subject is thereby "improved"), albeit not completely eliminated.

As used herein, "congestive heart failure" is a specific cardiovascular disease which is characterized, but not limited to, the following symptoms: shortness of breath, pitting edema, an enlarged and tender liver, engorged neck veins, and pulmonary rales in various combinations.

DETAILED DESCRIPTION OF THE INVENTION

The present invention relates to methods for the treatment of sexual dysfunction in males and females (including but not limited to erectile dysfunction) using halogenated derivatives of flosequinan and enantiomers of these same halogenated flosequinan derivatives. The present invention also describes methods for the synthesis of halogenated derivates of flosequinan and the enantiomers of these halogenated flosequinan derivatives. In preferred embodiments the present invention describes the administration, for the treatment of sexual dysfunction, of halogenated derivatives of flosequinan (and the enantiomers of these same halogenated flosequinan derivatives) to patients who are substantially free from symptoms of cardiac disease and who are not concurrently being treated with drugs which cause hypotensive effects, such as nitrites and nitrates.

However, it is not intended that the present invention be limited to the administration of halogenated flosequinan derivatives to subjects who are substantially free from symptoms of cardiac disease and who are not concurrently being treated with drugs which cause hypotensive effects, such as nitrites and nitrates. Indeed, in some embodiments, the present invention contemplates the administration of halogenated flosequinan derivatives in the treatment of cardiovascular disease.

In one embodiment, racemic monochloroflosequinan is administered. Importantly, racemic monochloroflosequinan may potentiate the hypotensive effects of nitrates, and its administration to patients who are concurrently using organic nitrates in any form may be contraindicated. It is contemplated that said racemic monochloroflosequinan be administered cutaneously, transurethrally, by standard injection, intracavernosally, intranasally or through respiratory inhalation. It is not intended that the methods of the present invention be limited to the mode of administration of said racemic monochloroflosequinan.

In one embodiment, the present invention contemplates the administration of the halogenated derivatives of flosequinan in concentrations sufficient to induce an erection in a human male suffering from impotence of any origin, other than anatomical deficiencies (i.e., lacking a penis or a significant portion thereof) that preclude an erection sufficient for vaginal penetration. In another embodiment, the present invention contemplates the administration of the enantiomers of these same halogenated flosequinan derivatives in concentrations sufficient to induce an erection in a human male suffering from impotence of any origin, other than anatomical deficiencies (i.e., lacking a penis or a significant portion thereof) that preclude an erection sufficient for vaginal penetration. In a preferred embodiment, the present invention contemplates the administration of (+) enantiomer of monochloroflosequinan [e.g. (S)-(+)-3-chloromethylsulfinyl-7-fluoro-1-methyl-4-quinolone] in concentrations sufficient to induce an erection in a human male suffering from impotence of any origin, other than anatomical deficiencies (i.e., lacking a penis or a significant portion thereof) that preclude an erection sufficient for vaginal penetration. In particular, these compositions may be used to induce an erection in a male suffering from impotence caused by severe atherosclerosis, and also impotence that is neurogenic or psychogenic in origin.

The present invention is not limited by a specific means of producing halogenated derivative of flosequinan or the enantiomers of halogenated flosequinan derivatives. However, to the extent that racemic flosequinan is used as a reagent in the preparation of said halogenated flosequinan derivatives (or the enantiomers of said halogenated flosequinan derivatives) said racemic flosequinan may be produced according the Teaching provided by U.S. Pat. Nos. 5,079,264 and 5,011,931 to MacLean et al., hereby incorporated by reference. In addition, a protocol for resolving the enantiomers of flosequinan (from a racemic mixture) is set forth in Morita et al., "Synthesis and Absolute Configuration of the Enantiomers of 7-Fluoro-1-methyl-3-(methylsulfinyl)-4(1H)-quinolinone (Flosequinan)," *Chem. Pharm. Bull.*, 42(10): 2157–2160 (1994), hereby incorporated by reference.

In addition to the protocols, as set out in U.S. Pat. Nos. 5,079,264 and 5,011,931 to MacLean et al, racemic flosequinan may be synthesized according to the protocol set out in Example 8 of the instant application.

A. Synthesis of Halogenated Derivatives of Flosequinan and the Synthesis of the Enantiomers of Halogenated Flosequinan Derivatives I. Monochloroflosequinan In one embodiment, the present invention describes the administration of racemic monochloroflosequinan (and derivates thereof) in the treatment of sexual dysfunction in males and females. In one embodiment, said monochloroflosequinan derivative is the sulfone derivative of monochloroflosequinan. In a one embodiment, the present invention describes the administration of a substantially purified enantiomer of monochloroflosequinan. In a preferred embodiment, said substantially purified enantiomer is the (+)-enantiomer of monochloroflosequinan (i.e. (S)-(+)-3-chloromethylsulfinyl-7-fluoro-1-methyl-4-quinolone). In one embodiment, said (+)-enantiomer of monochloroflosequinan is substantially free of the (−)-enantiomer of monochloroflosequinan.

In other embodiments, said substantially purified enantiomer of monochloroflosequinan is the (−)-enantiomer of monochloroflosequinan (i.e. (R)-(−)-3-chloromethylsulfinyl-7-fluoro-1-methyl-4-quinolone). In one embodiments, said (−)-enantiomer of monochloroflosequinan is substantially free of the (+)-enantiomer of monochloroflosequinan. It is not intended that the present invention be limited to complete separation of enantiomers, or 100% percent purity. It is sufficient that the preparation is enriched for one enantiomer (e.g. a 50:50 mixture becomes a 60:40 mixture).

Methods of producing a racemic mixture of flosequinan, as set out in U.S. Pat. Nos. 5,079,264 and 5,011,931 to MacLean et al., are hereby incorporated by reference. In one embodiment, racemic flosequinan is prepared according to the protocol set out in Example 8.

Without limiting the invention to any particular mechanism, racemic monochloroflosequinan, the enantiomers of monochloroflosequinan, and the sulfone derivatives of monochloroflosequinan are enzyme inhibitors. In specific examples, these compounds differentially inhibit various phosphodiesterases (e.g. PDE 1–6). The enzyme inhibition of racemic monochloroflosequinan, the enantiomers of monochloroflosequinan, and the sulfone derivatives of monochloroflosequinan has utility, for example, in therapeutics. Therefore, the present invention contemplates formulations and the administration of formulations to patients.

i. Synthesis of Racemic Monochloroflosequinan

In one embodiment, the synthesis of racemic monochloroflosequinan (3-chloromethylsulfinyl-7-fluoro-1-methyl-4-quinolone) may be carried out as a one step procedure, involving the direct chlorination of racemic flosequinan. In one embodiment, N-chlorosuccinimide is used in the chlorination. In one embodiment, the solvent is carbon tetrachloride (see Example 1), while in another embodiment the solvent is benzene (see Example 3).

In other embodiments, the synthesis of racemic monochloroflosequinan is carried out as a three step procedure, as described in more detail in Example 2. Briefly, in the first step, racemic flosequinan is reduced to desoxyflosequinan (7-fluoro-1-methyl-3-methylthio-4-quinolone). In the second step, desoxyflosequinan is chlorinated using N-chlorosuccinimide, to produce chlorodesoxyflosequinan (3-chloromethylthio-7-fluoro-1-methyl-4-quinolone). In the third step, chlorodesoxyflosequinan is subjected to oxidation to produce 3-chloromethylsulfinyl-7-fluoro-1-methyl-4-quinolone (monochloroflosequinan). Such oxidation may be accomplished using hydrogen peroxide.

In other embodiments, chlorodesoxyflosequinan is synthesized by reacting flosequinan with thionyl chloride and pyridine, as described in more detail in Example 4.

In yet other embodiments, the synthesis of monochloroflosequinan sulfone (3-chloromethylsulfonyl-7-fluoro-1-methyl-4-quinolone) is contemplated. In one embodiment, the synthesis of monochloroflosequinan sulfone is carried out by m-chloroperoxybenzoic acid oxidation of monochloroflosequinan, as described in Example 5.

ii. Synthesis of Monochloroflosequinan Enantiomers

In other embodiments, the synthesis and separation of enantiomers of monochloroflosequinan is contemplated. The (R)-(−)-enantiomer of monochloroflosequinan is synthesized by the stereopreferred oxidation of 3-chloromethylthio-7-fluoro-1-methyl-4-quinolone, followed by suitable separation procedures (see part C of Example 6). The (S)-(+)-enantiomer of monochloroflosequinan is synthesized by the stereopreferred oxidation of 3-chloromethylthio-7-fluoro-1-methyl-4-quinolone, followed by suitable separation procedures (see part D of Example 6).

The 3-chloromethylthio-7-fluoro-1-methyl-4-quinolone used as a substrate for the stereopreferred oxidation reactions may be synthesized by chlorination of 7-fluoro-1-methyl-3-methylthio-4-quinolone. In one embodiment, the chlorination is accomplished by the use of N-chlorosuccinimide (NCS) (see part B of Example 6). The 7-fluoro-1-methyl-3-methylthio-4-quinolone which serves as a substrate for the chlorination reaction may be produced by the catalytically reduction of 7-fluoro-1-methyl-3-methylsulfinyl-4-quinolone (see part A of Example 6). A variety of catalysts are contemplated, including but not limited to tetrabromomethane, carbon tetraiodide and iodide. In one embodiment tetrabromomethane is used with toluene as the solvent (see part A of Example 6). In another embodiment, anhydrous xylene is contemplated as the solvent, with tetrabromomethane as the catalyst (see Example 7).

The present invention also contemplates the formulation of comprising a racemic mixture of monochloroflosequinan, the enantiomers of monochloroflosequinan (and derivatives thereof) as a pharmaceutically acceptable salt. In addition, pharmaceutical formulations of a racemic mixture of monochloroflosequinan, the enantiomers of monochloroflosequinan (and derivatives thereof) may also contain binders, fillers, carriers, preservatives, stabilizing agents, emulsifiers, buffers and excipients as, for example, pharmaceutical grades of mannitol, lactose, starch, magnesium stearate, sodium saccharin, cellulose, and magnesium carbonate. The present invention also contemplates the administration of a racemic mixture of monochloroflosequinan, the enantiomers of monochloroflosequinan (and derivatives thereof) as a pharmaceutically acceptable salt or formulation. The present invention also contemplates the administration of a racemic mixture of monochloroflosequinan, the enantiomers of monochloroflosequinan (and derivatives thereof) formulations to a subject.

II. Use and Synthesis of Dichloroflosequinan Enantiomers

In one embodiment, the present invention describes the administration of dichloroflosequinan in the treatment of sexual dysfunction in males and females.

Methods of producing flosequinan, as set out in U.S. Pat. Nos. 5,079,264 and 5,011,931 to MacLean et al., are hereby incorporated by reference. In one embodiment, flosequinan is prepared according to the protocol set out in Example 11.

Furthermore methods for the preparation on monochloroflosequinan (a starting reagent, in a preferred embodiment, for the synthesis of dichloroflosequinan) is prepared according to the protocol set out in Example 12.

Without limiting the invention to any particular mechanism, dichloroflosequinan is also an enzyme inhibitor. In a specific example, dichloroflosequinan inhibits phosphodiesterases (herein after, "PDE"). This effect of dichloroflosequinan on enzyme activity, more particularly PDE, has utility in therapeutics.

The present invention also contemplates the formulation of dichloroflosequinan as a pharmaceutically acceptable salt. In addition, pharmaceutical formulations of dichloroflosequinan may also contain binders, fillers, carriers, preservatives, stabilizing agents, emulsifiers, buffers and excipients as, for example, pharmaceutical grades of mannitol, lactose, starch, magnesium stearate, sodium saccharin, cellulose, and magnesium carbonate. The present invention also contemplates the administration of dichloroflosequinan as a pharmaceutically acceptable salt or formulation. The present invention also contemplates the administration of dichloroflosequinan formulations to a patient.

The present invention teaches compositions and methods for the synthesis of 3-dichloromethylsulfinyl-7-fluoro-1-methyl-4-quinolone (dichloroflosequinan).

It is not intended that the present invention be limited to any particular method for the synthesis of 3-dichloromethylsulfinyl-7-fluoro-1-methyl-4-quinolone (dichloroflosequinan). In one embodiment, 3-dichloromethylthio-7-fluoro-1-methyl-4-quinolone is prepared and then reacted to produce 3-dichloromethylsulfinyl-7-fluoro-1-methyl-4-quinolone (dichloroflosequinan) in the following two step reaction.

1. Step One 3-dichloromethylthio-7-fluoro-1-methyl-4-quinolone [Compound (2) of FIG. 1] was prepared by reacting of monochloroflosequinan (3-chloromethylsulfinyl-7-fluoro-1-methyl-4-quinolone) [Compound (1) of FIG. 1] with thionyl chloride ("SOCl$_2$") and pyridine at a low temperature. This mixture was stirred and cooled, thereby, producing a solid that was filtered off, washed, and dried under vacuum.

2. Step Two

The 3-dichloromethylthio-7-fluoro-1-methyl-4-quinolone [Compound (2) of FIG. 1], prepared in step one, was then dissolved in dichloromethane ("DCM") and m-chloroperbenzoic acid ("MCPBA") at room temperature. This mixture was washed with Na$_2$CO$_3$, and the water layer was extracted with DCM.

The combined DCM solutions containing product were dried over Na$_2$SO$_4$ and concentrated to yield a final product of dichloroflosequinan.

III. Carboxyflosequinan

In one embodiment, the present invention describes the administration of carboxyflosequinan in the treatment of sexual dysfunction in males and females.

Methods of producing a racemic mixture of flosequinan, as set out in U.S. Pat. Nos. 5,079,264 and 5,011,931 to MacLean et al., are hereby incorporated by reference. In one embodiment, flosequinan is prepared according to the protocol set out in Example 15. The synthesis of carboxyflosequinan is set out in Example 14.

Without limiting the invention to any particular mechanism, carboxyflosequinan is also an enzyme inhibitors. In a specific example, carboxyflosequinan inhibit protein kinase C (herein after PKC). This effect of carboxyflosequinan on enzyme activity, more particularly on PKC, has utility in therapeutics.

IV. Fluorinated Flosequinan Derivatives

In one embodiment, the present invention describes the administration of monofluoroflosequinan, difluoroflosequinan, and difluoroflosequinan sulfone in the treatment of sexual dysfunction in males and females.

Without limiting the invention to any particular mechanism, monofluoroflosequinan and difluoroflosequinan are enzyme inhibitors. In a specific example, monofluoroflosequinan and difluoroflosequinan inhibit protein kinase C (herein after PKC). In another example, difluoroflosequinan (and its sulfone derivative) inhibit phosphodiesterases (herein after PDE). This effect of monofluoroflosequinan and difluoroflosequinan on enzyme activity, more particularly on PKC and PDE, has utility in therapeutics.

The present invention also contemplates the formulation of monofluoroflosequinan, difluoroflosequinan, and the sulfone derivative difluoroflosequinan as a pharmaceutically acceptable salt. In addition, pharmaceutical formulations of monofluoroflosequinan, difluoroflosequinan, and the sulfone derivative difluoroflosequinan may also contain binders, fillers, carriers, preservatives, stabilizing agents, emulsifiers, buffers and excipients as, for example, pharmaceutical grades of mannitol, lactose, starch, magnesium stearate, sodium saccharin, cellulose, and magnesium carbonate. The present invention also contemplates the administration of monofluoroflosequinan, difluoroflosequinan, and the sulfone derivative difluoroflosequinan as a pharmaceutically acceptable salt or formulation. The present invention also contemplates the administration of dichloroflosequinan and monofluoroflosequinan, difluoroflosequinan, and the sulfone derivative difluoroflosequinan formulations to a subject.

Figure 31:
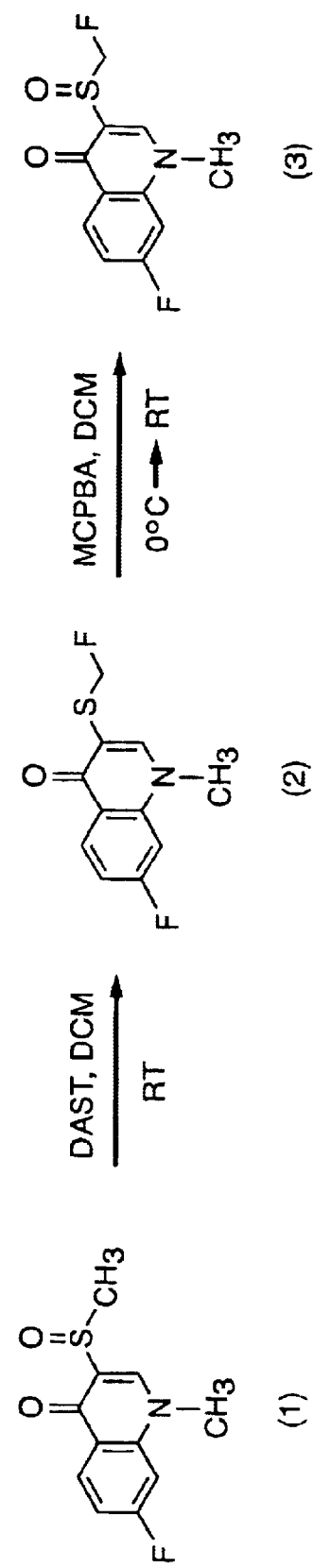
FIG. 31 depicts the steps in the chemical synthesis of 7-fluoro-3-fluoromethylsulfinyl-1-methyl-4-quinolone. Flosequinan (1) is reacted as described to generate 7-fluoro-3-fluoromethylthio-1-methyl-4-quinolone (2). 7-Fluoro-3-fluoromethylthio-1-methyl-4-quinolone (2) is reacted as described to generate 7-fluoro-3-fluoromethylsulfinyl-1-methyl-4-quinolone (3).

The synthesis of monofluoroflosequinan was carried out in two stages (see FIG. 31). Briefly, in the first stage, flosequinan was fluorinated by DAST in DCM at room temperature. This reaction was accompanied by the deoxygenation of the sulfoxide to the sulfide. In the second stage, MCPBA was used to oxidize the sulfide back to the sulfoxide.

In the first stage, DAST was added to a solution of flosequinan in DCM at 20° C. The mixture was stirred at room temperature (25° C.) for three days, then diluted with ether. In a preferred embodiment, the time required for this conversion can be reduced by the use of a suitable catalyst, including but not limited to antimony chloride (SbCl$_3$). In one embodiment, antimony chloride was used and the reaction time was 7 hours (see FIG. 32).

Figure 33:
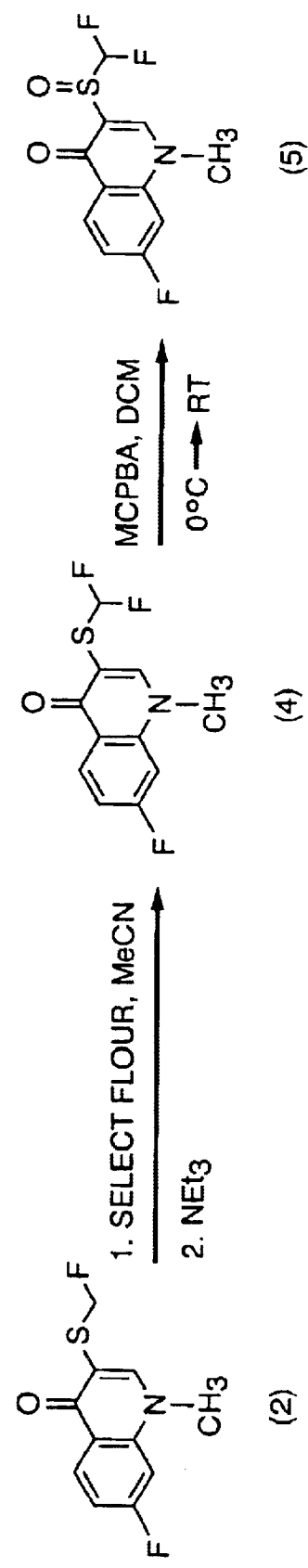
FIG. 33 depicts the steps in the chemical synthesis of 3-difluoromethylsulfinyl-7-fluoro-1-methyl-4-quinolone (5). 7-fluoro-3-fluoromethylthio-1-methyl-4-quinolone (2) is reacted as described to generate 3-difluoromethylthio-7-fluoro-1-methyl-4-quinolone (4). 3-difluoromethylthio-7-fluoro-1-methyl-4-quinolone (4) is reacted as described to generate 3-difluoromethylsulfinyl-7-fluoro-1-methyl-4-quinolone (5).

Since a few attempts to further fluorinate α-fluorosulfoxide (monofluoroflosequinan) were unsuccessful, the second fluorine atom was introduced into a side chain at an intermediate sulfide stage (see FIG. 33). Specifically, α-fluorosulfide (7-fluoro-3-fluoromethylthio-1-methyl-4-quinolone) was fluorinated with SELECT-FLUOR to give a complicated mixture, but a triplet in the $^1$H NMR spectrum (δ=7.10 ppm, J=58.9 Hz) was assigned to α,α-difluorosulfide (3-difluoromethylthio-7-fluoro-1-methyl-4-quinolone). The mixture was subsequently oxidized with MCPBA, to secure the desired α,α-sulfoxide (3-difluoromethylsulfinyl-7-fluoro-1-methyl-4-quinolone), although in low total yield. The fluorination reaction was not optimized.

Figure 35:
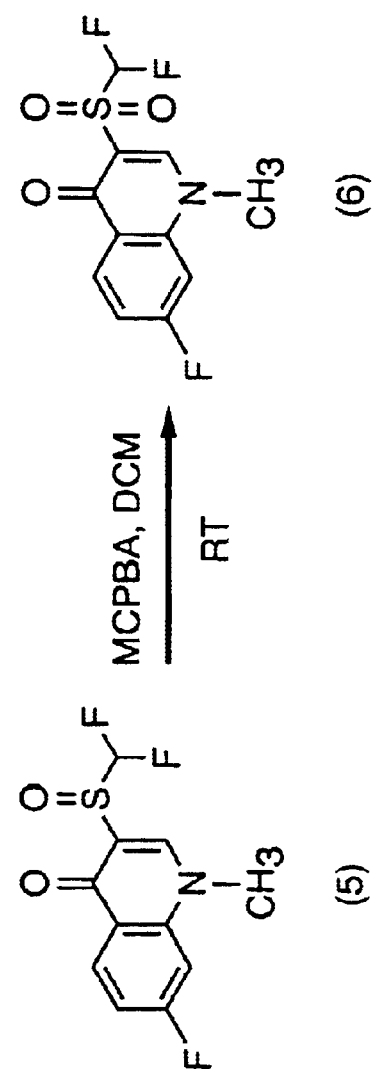
FIG. 35 depicts the synthesis of a sulfone derivative of difluoroflosequinan (5) corresponding to the chemical composition designated as 3-difluoromethylsulfonyl-7-fluoro-1-methyl-4-quinolone (6).

Difluoroflosequinan sulfone (3-difluoromethylsulfonyl-7-fluoro-1-methyl-4-quinolone) was prepared by MCPBA oxidation of difluoroflosequinan (3-difluoromethylsulfinyl-7-fluoro-1-methyl-4-quinolone). This synthesis is described in experimental Example 22 and is depicted in FIG. 35.

V. Enantiomers of Monochloroflosequinan

The present invention contemplates the use of the (+) and (−) enantiomers of monochloroflosequinan in the treatment of sexual dysfunction.

Many organic compounds, including monochloroflosequinan, exist in optically active forms (i.e., they have the ability to rotate the plane of plane-polarized light). In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory (rotates to the left). A compound prefixed with (+) or d is dextrorotatory (rotates to the right). For a given chemical structure, these compounds, called "stercoisomers," are identical except that they are mirror images of one another. A specific stereoisomer may also be referred to as an "enantiomer.

The present invention is not limited by any specific means for the stereopreferred synthesis or resolution of the (+) or (−) enantiomers of monochloroflosequinan. However, the (R)-(−)-enantiomer of monochloroflosequinan is synthesized by the stereopreferred oxidation of 3-chloromethylthio-7-fluoro-1-methyl-4-quinolone, followed by suitable separation procedures (see part C. of Example 6). The (S)-(+)-enantiomer of monochloroflosequinan is synthesized by the stereopreferred oxidation of 3-chloromethylthio-7-fluoro-1-methyl-4-quinolone, followed by suitable separation procedures (see part D. of Example 6).

The 3-chloromethylthio-7-fluoro-1-methyl-4-quinolone used as a substrate for the stereopreferred oxidation reactions may be synthesized by chlorination of 7-fluoro-1-methyl-3-methylthio-4-quinolone. In one embodiment, the chlorination is accomplished by the use of N-chlorosuccinimide (see part B. of Example 6). The 7-fluoro-1-methyl-3-methylthio-4-quinolone which serves as a substrate for the chlorination reaction may be produced by the catalytical reduction of 7-fluoro-1-methyl-3-methylsulfinyl-4-quinolone (see part A. of Example 6). A variety of catalysts are contemplated, including but not limited to tetrabromomethane, carbon tetraiodide and iodide. In one embodiment tetrabromomethane is used with toluene as the solvent (see part A. of Example 6). In another embodiment, anhydrous xylene is contemplated as the solvent, with tetrabromomethane as the catalyst (see Example 7).

While it is not necessary to understand any particular mechanism to carry out the present invention, it is believed that in some circumstances, enantiomers of monochloroflosequinan can act as a direct-acting vasodilator to relax the corpus cavernosum smooth muscle cells, which in turn increases blood flow into the cavernosa space. This then leads to increased cavernosa pressure to produce an erect penis or clitoris.

The action of the enantiomers monochloroflosequinan in the body are not precisely understood. Its activity in the body may be attributed to monochloroflosequinan itself and/or well as its sulfone metabolite It is not intended that the present invention be limited to any particular mechanism to reduce symptoms of sexual dysfunction. In one embodiment, the (+) and (−) enantiomers of flosequinan were subjected to biochemical assays to determine their respective percent inhibition of PDE3. In one embodiment, it was shown that the (+) enantiomer of flosequinan has an eight-fold increase in PDE3 inhibition as compared to that of the (−) enantiomer of flosequinan at the same molar concentration. Moreover, in the same embodiment, the (+) enantiomer of flosequinan exhibited greater inhibition of PDE3 than a racemic mixture of flosequinan at the same molar concentration.

VI. The Sulfone of Monochloroflosequinan

The present invention contemplates the use of monochloroflosequinan sulfone (3-chloromethylsulfonyl-7-fluoro-1-methyl-4-quinolone) in the treatment of sexual dysfunction. In one embodiment, the synthesis of monochloroflosequinan sulfone is carried out by m-chloroperoxybenzoic acid oxidation of monochloroflosequinan, as described in Example 5.

B. Diagnosis of Male Erectile Dysfunction

Determination whether a human male is suffering from impotence that is substantially only neurogenic or psychogenic is readily made by a person skilled in the art using a number of readily available diagnostic procedures. Thus, a male suffering from impotence can first be given a physical examination with particular attention to possible penile and scrotal pathology, whereby any anatomical deficiency precluding an erection sufficient for vaginal penetration can be detected. In the absence of such an anatomical deficiency, the male can be subjected to tests, whereby penile venous leakage or severe or untreatable atherosclerosis can be detected.

Such tests include determination of the penobrachial blood pressure index (PBPI), doppler investigation of the penile arteries, and a papaverine test. The PBPI is the penile systolic blood pressure divided by the systolic blood pressure determined at one of the arms. These blood pressures can be determined by any number of standard techniques. Thus, the penile systolic blood pressure can be determined by i) placing an inflatable cuff around the base of the free part of the penis in the flaccid state which is capable of being used to apply variable pressure, readable from a gauge, to an object around which the cuff is placed, ii) localizing the penile arteries with a Doppler ultrasound probe (e.g., 8 MHz probe, such as the Mini Doplex D500 available from Huntleigh Technology, Luton, United Kingdom), and then iii) inflating and deflating the cuff and ascertaining the pressure at which the Doppler sound reappears.

The pressure at which the Doppler sound reappears is the penile systolic blood pressure. A male's penile blood pressure is regarded as normal if his PBPI is >0.80. With regard to Doppler investigation, each of the two penile cavernous arteries is investigated distal to the aforementioned cuff using the Doppler ultrasound problem. The function of each of the two arteries is assessed by Doppler ultrasound using an arbitrary scale of 0, 1, 2 or 3, where 0 means that the function is so deficient that the artery cannot be located and 3 means that the artery is well enough that maximal Doppler sound is observed.

In the papaverine test, a tourniquet is placed at the base of the free part of the penis and tightened and then, with the patient seated, 30 mg of papaverine in 1 ml of a physiologically acceptable fluid (e.g., physiological saline or phosphate-buffered saline) is injected into the penile cavernous body. In persons suspected of having impotence due to a suprasacral nerve lesion or a psychogenic dysfunction, only 15 mg of papaverine is administered, because of the high incidence of papaverine-induced priapism in such cases.

Five minutes after the injection, the tourniquet is removed and an ultrasound Doppler investigation of the penile cavernous arteries is carried out as described above. The function of the arteries is regarded as normal if both of them score a 3 on the arbitrary scale. After the Doppler investigation, penile vibration, at about a 4 Hz with an amplitude of about 1.2 mm (carried out with, e.g., a Vibrector, from Multicept, Gentofte, Denmark) is carried out for five to ten minutes and then erectile response is evaluated.

Erectile response is classified as full rigidity, if the angle between the penis and the legs in the standing position is >90°, and tumescence or no response if the angle is less than or equal to 45°. An impotent male, who does not have an anatomical deficiency that would preclude having an erection sufficient for vaginal penetration, who has a PBPI >0.80, who has scores of 2 or 3 in Doppler ultrasound investigations of both of the cavernous arteries of the penis, after papaverine injection as described above, and who has a fully rigid erection after papaverine injection and vibration as described above, is suffering from impotence that is "substantially only neurogenic or psychogenic" in origin.

It is possible that atherosclerosis or venous leakage contributes to such impotence, and atherosclerosis likely does contribute if the score is less than 3 in the Doppler investigation of one or both of the cavernous arteries after papaverine injection; but any venous leakage or atherosclerosis in such impotence is not untreatable and, consequently, is not a substantial factor in the impotence and such atherosclerosis, if any, is less than severe.

Impotence, which is a side-effect of drugs such as beta-blockers, is deemed to be neurogenic impotence in the present specification. Similarly, impotence which is a result of alcoholism or excessive consumption of alcohol, is deemed to be neurogenic or psychogenic impotence, for purposes of the present specification. Thus, a male who is diagnosed in accordance with the present specification as suffering from impotence that is "substantially only neurogenic or psychogenic" in origin is suffering from impotence that is substantially only neurogenic, psychogenic or neurogenic and psychogenic in origin, even though an underlying cause of the impotence has been identified as a side-effect of a drug, alcoholism or excessive consumption of alcohol.

Generally, a male with a PBPI less than about 0.60, with scores of 0 in Doppler investigations of both penile cavernous arteries (after papaverine injection as described above), and with a less than fully rigid erection after papaverine injection and vibration will have impotence caused by "untreatable" atherosclerosis. Methods are available to ascertain whether impotence is untreatable because of venous leakage.

One method of ascertaining whether untreatable venous leakage is a cause of impotence is by cavernosometry, optionally supplemented with cavernosography. (See, e.g., Delcour et al., *Radiology* 161: 799 (1986); Porst et al., *J. Urol.* 137: 1163 (1987); Lue et al., *J. Urol.* 37: 829 (1987)). Cavernosometry can be done using, both before and after intracavernosal injection of 60 mg of papaverine (in 1 ml of physiological saline), infusion of physiological saline through a 19-gauge needle into one corpus cavernosum with a 21-gauge needle inserted into the other corpus cavernosum for measurement of intracorporal pressure (which is recorded on a plotter). The infusion rates needed to induce and maintain an erection are measured. If the infusion rate needed to maintain an erection is greater than 50 ml/min before administration of the papaverine and greater than 15 ml/min after administration of the papaverine, untreatable venous leakage is present. As long as an erection can be achieved at some flow rate less than about 100 ml/min before injection of the papaverine and less than about 50 ml/min after the injection of papaverine, it might be possible, using cavernosography, to locate the venous lesion associated with the leakage, and thereby confirm the diagnosis based on cavernosometry and provide information for possible surgical correction for the leakage. In the cavernosography, the penis is X-rayed, both before and after intracavernosal injection of 60 mg papaverine (in 1 ml of physiological saline), while infusing contrast medium into the corpus cavernosum (e.g., through a 19-gauge needle) at a flow rate that maintains an erection during the X-ray. Numerous contrast media suitable for the procedure are available in the art; these are typically aqueous solutions of iodinated compounds that provide between about 180 mg/ml and about 360 mg/ml of iodine. Examples are a solution of iohexol providing 240 mg/ml of iodine sold by Winthrop Pharmaceuticals, New York, N.Y., USA, and a solution of iopamidol providing 300 mg/ml iodine sold by Astra Meditec, Goteborg, Sweden. Typically 50–100 ml of the contrast medium will be employed for each x-ray (i.e., before and then after the injection of papaverine). In the cavernosometry and cavernosography, 30 mg papaverine (in 1 ml physiological saline) coupled with stimulation by vibration can be employed in place of 60 mg papaverine (in 1 ml physiological saline).

C. Diagnosis of Female Erectile Dysfunction

Females have sexual dysfunction. Post-menopausal women often complain of discomfort with intercourse, dryness of the vagina and diminished vaginal arousal. Studies comparing sexual dysfunction in couples have revealed 40% of the men had erectile or ejaculatory dysfunction, whereas 63% of the women had arousal or orgasmic dysfunctions. Similar to male sexual dysfunction, the prevalence of female sexual dysfunction has been shown to increase with age and be associated with the presence of vascular risk factors and the development of the menopause.

The clitoris is the homologue of the penis. It is a cylindrical, erectile organ composed of the glans, corporal body and the crura. The corporal body is surrounded by a fibrous sheath, tunica albuginea, which encases cavernosal tissue consisting of sinusoids and surrounding smooth muscle. The clitoris responds to sexual excitement by tumescence and erection, although this does not occur with the degree of pressure elevation as found during penile erection. The characteristics of the clitoral blood flow, however, approximately parallel those of the male. See K. Park et al., "Vasculogenic female sexual dysfunction: The hemodynamic basis for vaginal engorgement insufficiency and clitoral erectile insufficiency," *Int. J. Impotence Res.* 9:27 (1997).

Post-menopausal women and women with a history of vascular risk factors have been shown to have significantly more complaints of self-reported female vaginal and clitoral dysfunctions than pre-menopausal women or women without vascular risk factors. Such problems include, but are not limited to, atherosclerosis-induced vaginal engorgement insufficiency and clitoral erectile insufficiency syndromes.

Determination whether a human female is suffering from poor blood flow or supply is readily made by a person skilled in the art using a number of readily available diagnostic procedures. The human vagina receives arterial blood supply from the vaginal artery, the vaginal branch of the uterine artery, the internal pudendal artery, and the vaginal branches of the middle rectal artery. Blood flow in these areas can readily be assessed by a number of techniques. Arterial blood can be obtained and the blood levels of cholesterol and triglycerides can be analyzed as a first step. However, the preferred method is imaging.

While relatively non-invasive imaging is preferred, more invasive techniques can be used. For example, vaginal wall blood flow can be measured by laser Doppler flow probes placed into the vaginal muscularis layer within the spongy region of blood-filled spaces and vascular smooth muscle. Clitoral intracavernosal erectile tissue blood flow can be measured with a similar laser Doppler flow probe placed into the corporal bodies. The flow probes are connected to a laser Doppler flowmeter (Transonic Systems, Inc.) which is calibrated against an internal standard reading flow in units of m/min/100 gm of tissue.

The laser Doppler probe uses the Doppler shift of a projected beam of laser light that registers on a photodetector. Static tissues will produce no Doppler shift in wavelength but moving red blood cells will produce a shift proportional to the red cell velocity.

D. Treatment of Male and Female Erectile Dysfunction

It is not intended that the present invention be limited by the formulation of any of the compositions described in the instant application. That is to say, racemic monochloroflosequinan, the enantiomers of monochloroflosequinan, the sulfone of monochloroflosequinan, monofluoroflosequinan, difluoroflosequinan and/or carboxyflosequinan may be formulated in a variety of therapeutic preparations. In selected embodiments, these compounds may be provided as a therapeutic preparation by combining the compound(s) a physiologically tolerable liquid, gel or solid carrier, diluents, adjuvants and/or excipients. More specifically, such therapeutic preparations may contain binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These formulation typically contain 1%–95% may be provided as a therapeutic preparation by combining the (+) enantiomer monochloroflosequinan with a physiologically tolerable liquid, gel or solid carrier, diluents, adjuvants and/or excipients. More specifically, such therapeutic preparations may contain binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%–95% of active ingredient (e.g. halogentated flosequinan derivatives and the enantiomers of halogentated flosequinan derivatives). In preferred embodiments these formulations contain 2%–70% of active ingredient.

In a preferred embodiment, the (+) enantiomer of monochloroflosequinan is provided as a therapeutic preparation. In another embodiment, (+) enantiomer of monochloroflosequinan is combined with other chemotherapeutic agents.

The present invention is not limited by the method of introduction of the therapeutic preparations into the body. Among other methods, the present invention contemplates administering cutaneously, orally, intracavernosally, transurethrally, by standard injection (e.g. intravenous or intramuscular), intranasally or through respiratory inhalation.

It is believed that oral administration of the (+) enantiomer of monochloroflosequinan enantiomer and pharmaceutical compositions comprising the (+) enantiomer of monochloroflosequinan is an effective mode of administration. Peak plasma concentrations of the (+) enantiomer of monochloroflosequinan are observed 1–2 hours following oral administration, while peak metabolite plasma levels are observed about seven hours following oral dosage. In one embodiment, the enantiomer of flosequinan or monochloroflosequinan is introduced into the male or female orally. It is believed that an oral dosage up to approximately 200 milligrams of a racemic mixture of flosequinan or monochloroflosequinan is an effective oral dosage. It is also believed that the oral administration of a purified of enantiomer of flosequinan or monochloroflosequinan is effective at even lower dosages (e.g. less than 200 mg). While the present invention is not limited to a specific dosage level, in one embodiment, the male or female is an adult human and the oral dosage of a purified enantiomer of flosequinan or monochloroflosequinan is in a single dose per day of up to approximately two hundred milligrams, more preferably, between approximately fifty to approximately seventy-five milligrams. In an even more preferred embodiment, a purified enantiomer of flosequinan is administered in a single oral dose per day of between approximately twenty and approximately fifty, and even more preferably, between approximately ten and approximately twenty milligrams per day.

The enantiomers of monochloroflosequinan are water soluble as well as soluble in many organic solvents. Thus, while the present invention is not limited by the form of oral administration, aqueous and organic solutions of monochloroflosequinan enantiomer for oral administration are contemplated. Monochloroflosequinan enantiomers can be associated with a solid pharmaceutical carrier for solid oral administration (i.e., in pill form). One skilled in the art is able to readily prepare such solid formulations, and in one embodiment, the inactive ingredients include croscarmellose sodium, hydroxypropyl methylcellulose, lactose, magnesium stearate, methocel E5, microcrystalline cellulose, povidine, propylene glycol and titanium dioxide.

Therapeutic formulations comprising monochloroflosequinan enantiomers may also be administered cutaneously in a carrier adapted for topical administration. Such carriers include creams, ointments, lotions, pastes, jellies, sprays, aerosols, bath oils, or other pharmaceutical carriers which accomplish direct contact between the active ingredient and the pore of the skin. In general, pharmaceutical preparations may comprise from about 0.001% to about 10%, and preferably from about 0.01 to 5% by w/w of the active compound (e.g., (+)-monochloroflosequinan) in a suitable carrier. In some cases it may be necessary to dissolve the (+)-monochloroflosequinan in an appropriate solvent such as ethanol or DMSO (dimethylsulfoxide). Likewise, the present invention can be incorporated in other products associated with sexual activity. For example, a coated, erection inducing condom as disclosed in U.S. Pat. No. 4,829,991, hereby incorporated by reference, can be utilized with flosequinan monochloroflosequinan enantiomers or pharmaceutical compositions comprising flosequinan or monochloroflosequinan enantiomers.

While the present invention is not limited by a specific method of introducing monochloroflosequinan enantiomers, and pharmaceutical preparations thereof, injection monochloroflosequinan enantiomers can be carried out by any conventional injection means (e.g., employing an hypodermic syringe and needle or a similar device such as the NovolinPen. sold by Squibb-Novo, Inc., Princeton, N.J., USA). This injection administer by self injection or by another person (such as a partner during sexual relations or a physician prior to sexual relations) injecting the male whose erection is to be induced. In one embodiment, monochloroflosequinan enantiomers are introduced intracavernosally as described in U.S. Pat. No. 5,447,912 to Gerstenberg et al., hereby incorporated by reference.

Monochloroflosequinan enantiomers (or a pharmaceutical composition comprising monochloroflosequinan), are dissolved or suspended, such that the resulting composition is suitable for intracavernosal injection. Such a physiologically acceptable composition can also include a non-irritant preservative, such as, e.g., benzalkonium chloride at 0.05% (w/v) to 0.2% (w/v). As the skilled artisan will understand, there are numerous non-toxic salts of VIP, PHM and α-adrenergic blockers that can be employed in a physiologically acceptable composition for use in the methods herein, including, among others, the chloride, bromide, acetate, sulfate, and mesylate salts.

In carrying out the methods recited in selected embodiment of the present invention it is preferred that, for a period of time between about 1 minute and about 15 minutes (preferably about 5 minutes–10 minutes), the penis is constricted near the base thereof and between the base and the point at which the injection into a corpus cavernosum occurs, in order to limit loss of injected fluid from the corpus cavernosum before the ingredients in the fluid, that are active in inducing erection, have been able to have erection-inducing effects. The constriction can be effected by any means known in the art, such as with a tourniquet, cuff, rubber band or the like, or even manually, in order to slow the release of the injected fluid and the pharmacologically active substance(s) therein into the general circulation.

Likewise, the present invention is not limited by a particular method for introducing halogenated derivatives of flosequinan, the enantiomers of halogenated derivatives of flosequinan and pharmaceutical compositions of the same transurethrally. In a preferred embodiment, the (+) enantiomer of monochloroflosequinan, or a pharmaceutical composition thereof, is introduced to the urethra in a carrier as described for cutaneously administration. Devices and methods for transurethral introduction of pharmaceutical compositions is described in U.S. Pat. No. 5,474,535 to Place et al.; Voss, U.S. Pat. No. 4,801,587 and Kock, EPA 0357581, all hereby incorporated by reference.

Additional methods of the transurethral introduction of compositions described in the present invention include the use of medicated catheters, such as those used to prevent or treat localized infections and irritation of the urethra and bladder (See U.S. Pat. No. 4,640,912, hereby incorporated by reference). Alternatively, transurethral administration of pharmaceutical compositions is presented in U.S. Pat. Nos. 4,478,822, 4,610,868, 4,640,912 and 4,746,508, all hereby incorporated by reference, and medicated urethral suppositories, inserts or plugs, typically containing anti-infective agents or spermicide are disclosed in U.S. Pat. Nos. 1,897,423, 2,584,166, 2,696,209 and 3,373,746, all incorporated by reference.

While the present invention is not limited to the method of injecting halogenated derivatives of flosequinan and the enantiomers of halogenated derivatives of flosequinan, in one embodiment these compound are injected with a standard syringe. One skilled in the art would be capable of injecting, for example, the (+) enantiomer of monochloroflosequinan (or a pharmaceutical composition comprising the (+) enantiomer of monochloroflosequinan with a carrier as described above) for intracavernosal injection.

Halogenated derivatives of flosequinan, the enantiomers of halogenated derivatives of flosequinan and pharmaceutical compositions of the same may also be administered intranasally. In selected embodiments, formulations suitable for intranasal administration include ointments, creams, lotions, pastes, gels, sprays, aerosols, oils and other pharmaceutical carriers which accomplish direct contact between monoflosequinan or a pharmaceutical composition comprising monoflosequinan and the nasal cavity. Examples of pharmaceutical compositions administered intranasally are described in U.S. Pat. Nos. 5,393,773 and 5,554,639 to Craig et al.; and U.S. Pat. No. 5,801,161 to Merkus, all hereby incorporated by reference.

Halogenated derivatives of flosequinan, the enantiomers of halogenated derivatives of flosequinan and pharmaceutical compositions of the same may also be administered via respiratory inhalation. Formulations suitable for respiratory inhalation include ointments, creams, lotions, pastes, gels, sprays, aerosols, oils and other pharmaceutical carriers. Examples of pharmaceutical compositions administered through respiratory inhalation are described in U.S. Pat. Nos. 4,552,891 to Hu et al.; U.S. Pat. No. 5,869,479 to Kreutner et al., and U.S. Pat. No. 5,864,037 to Chasis et al.

In some embodiments, intranasal administration and respiratory inhalation are the preferred modes of administration due to the ease of administration and faster onset of therapeutic activity. It is contemplated that intranasal administration and respiratory inhalation are advantageous as they may allow a smaller effective dosage to be administered than would be possible with the oral route of administration. A preferred mode of administration comprises administration to the lung. Intrapulmonary delivery of pharmacological agents to patients can be accomplished via aerosolization. Alternatively, the agent may be administered to the lung through a bronchoscope. Of course, the therapeutic agents may be investigated for their efficacy via other routes of administration, including parenteral administration.

In one embodiment, the administration of the compositions of the present invention is accompanied by sexual stimulation to induce an erection. The sexual stimulation can begin before or after the introduction the halogenated derivatives of flosequinan, the enantiomers of halogenated derivatives of flosequinan, and/or pharmaceutical compositions of the same. If the stimulation begins after the injection, it is preferably begun within 5 to 10 minutes to insure that there is significant overlap of the pharmacological effects of the pharmaceutical composition administered and the simulative effects of the sexual stimulation. Whether the stimulation begins before or after the injection, it will continue preferably at least until an erection sufficient for vaginal penetration is achieved.

Sexual stimulation as prescribed by these methods, includes any form of sexual stimulation that would induce an erection in a normal male who is not suffering from erectile insufficiency. The sexual stimulation can be that which occurs in the course of sexual relations between the subject and another person or can be outside sexual relations with another person. Examples of methods of sexual stimulation include, alone or in combination, touching or erotically manipulating erogenous areas of the genital organs or other erogenous parts of the body; providing visual stimulation, as with a sexually explicit media (e.g., pornographic film) or other form of sexually stimulative show or display. Additionally, providing vibratory stimulation to the penis, at between about 30 Hz and about 100 Hz with an amplitude of about 1 mm to about 5 mm, as can be provided, for example, by resting the penis on the table of a vibrating apparatus such as that of a Vibrector system (Multicept, Genofte, Denmark).

In inducing an erection in an impotent male outside of sexual relations, as, for example, when a physician induces an erection in a patient suffering from psychogenic impotence, a preferred method of sexual stimulation includes providing visual stimulation, as with a pornographic film, simultaneously with vibratory stimulation of the penis, as with a Vibrector system set to between about 30 Hz and about 60 Hz (usually about 50 Hz) in frequency and between about 1 mm and about 2.5 mm (usually about 2.2 mm) in amplitude.

From the above, it should be clear that the present invention provides methods of treatment of sexual dysfunction (e.g. erectile dysfunction) with halogenated derivatives of flosequinan, the enantiomers of halogenated derivatives of flosequinan and/or pharmaceutical compositions of the same. In preferred embodiments, racemic monochloroflosequinan and/or monochloroflosequinan enantiomers (and pharmaceutical compositions of the same) comprising flosequinan are administered therapeutically to patients demonstrating at least one symptom of sexual dysfunction.

E. The Treatment of Cardiovascular Disease

The present invention also relates to methods for the treatment of cardiovascular disease. In one embodiment, the present invention contemplates compositions and methods for the treatment of CHF and hypertension.

In another embodiment, the present invention contemplates compositions and methods for the treatment of CHF and hypertension in subjects who are not concurrently being treated with nitrites or nitrates. In a preferred embodiment, the present invention contemplates the administration halogenated derivatives of flosequinan in methods for treating CHF and hypertension. It is contemplated that the halogenated derivatives of flosequinan, described in various embodiment of the present invention, may be administered cutaneously, by standard injection, intranasally, or through respiratory inhalation. It is not intended that the methods of the present invention be limited to the mode of administration of the halogenated derivatives of flosequinan.

1. Evaluation of Compounds for Efficacy as Anti-Hypertensives

The antihypertensive effects exerted by the halogenated derivatives of flosequinan are readily demonstrated by means of tests on known strains of laboratory animals. It is not intended that the present invention be limited by the species of animal used as a test platform. Suitable animal models include, but are not limited to, species including rodents, non-human primates, ovines, bovines, ruminants, lagomorphs, porcines, caprines, equines, canines, felines, and aves.

In one embodiment, female rats (weight range 180–240 g) of the Aoki-Okamoto strain of spontaneously hypertensive can be used. The rats are divided into groups of four and will be fasted overnight before administration of a halogenated derivative of flosequinan (or a combination of the halogenated flosequinan derivative). Blood pressure will be determined in the following way.

The rats are placed in a restraining cage, maintained at 38° C., with their tails protruding through holes in the cage. After 30 minutes in the cage, blood pressure will be measured using an inflatable cuff placed round the base of the tail and arterial pulsations will be monitored with a pneumatic pulse transducer. In other animal models, however, a limb or a phalanx as a site to monitor blood pressure. A pressure, greater than the expected blood pressure, will be applied to the cuff and this pressure will be slowly reduced. The pressure in the cuff at which arterial pulsations reappears will be recorded as the blood pressure. The rats will be removed from the cage and each group will be orally administered a given dose of a halogenated flosequinan derivative. In addition to the pre-dose reading, blood pressure will be measured at 1.5 and 5.0 hours after dosing. In one embodiment, a effective dosage will be defined as follows.

A halogenated derivative of flosequinan will be tested initially at a given dose level (for example 90 mg/kg). If the compound is considered sufficiently active (giving a reduction of blood pressure equal to or greater than of approximately 15% after correction) it will be retested at a lower dose level, for example 30 mg/kg. By testing at successively lower dose levels, a threshold antihypertensive dose (dose giving a reduction of blood pressure of between 5 and 15% after correction) will be determined.

Compounds which are inactive at a particular dose level and which produce a reduction of blood pressure equal to or greater than 15% after correction at the next highest dose level will be designated as having a threshold antihypertensive dose within the range covered by the two dose levels.

The above described protocol is suited it a variety of hypertensive and normotensive animal models. In a preferred embodiment, a normotensive marmoset monkey will be used.

2. Evaluation of Compounds for Efficacy in the Treatment of CHF a. Surgical Preparation Mature *M. fascicularis* primates will be premedicated with ketamine hydrochloride (15 mg/kg im) and glycopyrrolate (0.01 mg/kg im). Following intubation, anesthesia will be maintained with 0.5% to 1% isoflurane. A left thoracotomy, including removal of the fourth or fifth rib, will be performed under sterile conditions and the pericardium will be opened and reflected to expose the heart. Silastic catheters attached to subcutaneous vascular access ports (VAPs; Access Technology) will be inserted into the descending thoracic aorta and into the right atrium via the atrial appendage. To measure LV pressure, a solid-state micromanometer (available from Konigsberg Instruments) will be introduced via a stab wound in the ventricular apex and secured with a purse-string suture. A unipolar pacing lead will be sutured to the posterior wall of the LV and connected to a programmable pacemaker (for example a Medtronic, Model Minix 8340) that will be situated subcutaneously over the left chest wall. Internal electrocardiogram (ECG) leads will be sutured to the chest wall. All catheters and wires will be tunneled subcutaneously to the dorsal midline below the scapula. Transdermal titanium skin buttons (available from Konigsberg Instruments) attached to the wires from the LV pressure transducer and ECG leads will be secured along the midline, while the catheter VAPs will be situated in subcutaneous pockets. The chest will be closed in layers and negative intrapleural pressure restored via a temporary chest tube. Antibiotics (Cefazolin, 30 mg/kg) will be administered subcutaneously prior to surgery and post-operatively for 10 days (30 mg/kg bid). Buprenorphine (0.01 mg/kg sq) will be administered for analgesia immediately after surgery and as needed the first postoperative week. All monkeys will be allowed to recover for a minimum of 2 weeks after surgery and were conditioned to sit in upright/reclining primate restraint chairs prior to commencement of experimental investigations.

b. Hemodynamic Measurements

Arterial blood pressure will be measured by inserting into the aortic VAP a saline-filled needle-tipped catheter, the other end of which was connected to a Statham P23 XL pressure transducer. Intravenous agents will be delivered via a similar catheter extension set inserted into the right atrial VAP. Left ventricular pressure (LVP) will be measured via the Konigsberg micromanometer and will be cross-calibrated with the aortic pressure signal, and the transthoracic ECG will be measured using a Gould ECG/Biotach amplifier (Gould Instrument Systems). All physiological signals will be sampled at 500 Hz using a computerized digital data acquisition system (Po-Ne-Mah, Gould Instrument Systems), while being simultaneously recorded on digital audio tape (Model RD 111T, Teac) and displayed on an MT 95000 eight-channel thermal-array recorder (Astro-Med). Measurements of heart rate (HR), mean arterial blood pressure (MAP), left ventricular systolic and end-diastolic blood pressures (LVSP and LVEDP, respectively), and the peak positive rate of change in LVP (+dP/dt$_{max}$) will derived using algorithm-based analyses of the digitized waveforms.

c. Myocardial Function Measurements

LV dimensions will be recorded with the primates under ketamine sedation using M-mode echocardiographic imaging (Hewlett Packard Sons 100CF) of the LV via a left transthoracic approach. Images will be recorded on VHS tape for subsequent calculation of LV fractional shortening and wall thickening percentage (WT) from the short axis and wall thickness dimensions. In addition, ejection fraction (EF) will be calculated by applying the Teicholz formula to the respective short axis dimensions measured at end-diastole and end-systole {EDV=[7/(2.4+LVDd)](LVDd$^3$) and ESV=[7/(2.4+LVD$_s$)](LVD$_s^3$) for end diastolic and end systolic volumes, respectively}. Utilizing simultaneous ECG recordings on the videotape, end-diastolic dimensions will be defined as occurring at the peak of the R-wave, while end-systole will be associated with the peak of the T-wave. Systolic WT will be then calculated as the difference between end-systolic and end-diastolic dimensions and is expressed as percent change from end-diastolic thickness [(EST−EDT)/EDT]×100.

It is not intended, however, that the present invention be limited by the species of the animal model used to evaluate the efficacy of a given compound as potential CHF therapeutic. The above described protocol is suited it a variety of hypertensive and normotensive animal models. In a preferred embodiment, a normotensive marmoset monkey will be used.

3. Diagnosis of Cardiovascular Disease

Determination whether an adult human is suffering from cardiovascular disease is readily made by a person skilled in the art using a number of readily available diagnostic procedures. Thus, an adult human suffering from cardiovascular disease can first be given a physical examination with particular attention to possible blood pressure or heart rhythm pathology, whereby many anatomical electrophysiological cardiovascular abnormalities can be detected.

Tests to determine hypertension may be performed by doppler investigation of the venous blood return system sufficiency. Blood pressures can be determined by a number of standard techniques.

Tests to determine myocardial infarction include detecting aberrations in blood enzymes. Following a myocardial infarction the damaged heart cells release of lactate dehydrogenase (LDH) subtypes result in circulating ratios that are not normally observed in a healthy person.

Test to determine angina pectoris include testing procedures as with myocardial infarction, only with the appearance of normal LDH subtype ratios.

Test to determine congestive heart failure include comparisons of blood pressures, cardiac output and stroke volume measurement. Congestive heart failure is a debilitating progressive condition that is fatal if immediate action is not taken.

4. Treatment of Cardiovascular Disease

It is not intended that the present invention be limited by the particular nature of a preparation. In some embodiments, a halogenated derivative of flosequinan (or a combination of halogenated flosequinan derivatives) is provided together with physiologically tolerable liquid, gel or solid carriers, diluents, adjutants and excipients. In addition, enantiomers of flosequinan may be used together with other chemotherapeutic agents. On the other hand, formulations may also contain such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%–95% of active ingredient, preferably 2%–70%.

The present invention is not limited by the method of introduction of the compound to the body. Among other methods, the present invention contemplates administering cutaneously, orally, or by standard injection (e.g. intravenous).

The present invention also contemplates administering a halogenated derivative of flosequinan (or a combination of halogenated flosequinan derivatives) to the subject intranasally or through respiratory inhalation. Formulations suitable for intranasal administration include ointments, creams, lotions, pastes, gels, sprays, aerosols, oils and other pharmaceutical carriers which accomplish direct contact between a halogenated derivative of flosequinan (or a combination of halogenated flosequinan derivatives) or a pharmaceutical composition comprising a halogenated derivative of flosequinan (or a combination of halogenated flosequinan derivatives) and the nasal cavity. Examples of pharmaceutical compositions administered intranasally are described in U.S. Pat. Nos. 5,393,773 and 5,554,639 to Craig et al.; and U.S. Pat. No. 5,801,161 to Merkus, all hereby incorporated by reference. Formulations suitable for respiratory inhalation include ointments, creams, lotions, pastes, gels, sprays, aerosols, oils and other pharmaceutical carriers which accomplish direct contact between an enantiomer of flosequinan or a pharmaceutical composition comprising an enantiomer of flosequinan and the respiratory tract. Examples of pharmaceutical compositions administered through respiratory inhalation are described in U.S. Pat. No. 4,552,891 to Hu et al.; U.S. Pat. No. 5,869,479 to Kreutner et al., and U.S. Pat. No. 5,864,037 to Chasis et al., all hereby incorporated by reference.

In some embodiments, intranasal administration and respiratory inhalation are the preferred modes of administration due to the ease of administration and faster onset of therapeutic activity. It is contemplated that intranasal administration and respiratory inhalation are advantageous as they may allow a smaller effective dosage to be administered than would be possible with the oral route of administration. A preferred mode of administration comprises administration to the lung. Intrapulmonary delivery of pharmacologic agents to subjects can be accomplished via aerosolization. Alternatively, the agent may be administered to the lung through a bronchoscope. Of course, the therapeutic agents may be investigated for their efficacy via other routes of administration, including parenteral administration.

The embodiments of the present invention directed to the administration of halogenated flosequinan derivatives in the treatment of cardiovascular disease are not limited to a specific dosage level. In selected embodiments, however, adult humans will be administered a single dosage (per day) of a halogenated flosequinan derivative in a range from 10 milligrams to approximately 200 milligrams. Multiple dosages (per day) are also contemplated.

Halogenated derivatives of flosequinan are water soluble and soluble in many organic solvents. Thus, while the cardiovascular therapeutic embodiments of the present invention are not limited by the form of oral administration, an aqueous and organic solution of a halogenated derivative of flosequinan (or a combination of halogenated flosequinan derivatives) for oral administration is contemplated. Likewise, a halogenated derivative of flosequinan (or a combination of halogenated flosequinan derivatives) can be associated with a solid pharmaceutical carrier for solid oral administration (i.e., in pill form). One skilled in the art is able to readily prepare such solid formulations and, in selected embodiments, the inactive ingredients include croscarmellose sodium, hydroxypropyl methylcellulose, lactose, magnesium stearate, methocel E5, microcrystalline cellulose, povidine, propylene glycol and titanium dioxide.

A halogenated derivative of flosequinan (or a combination of halogenated flosequinan derivatives) may also be administered (as a cardiovascular therapeutic) cutaneously in a carrier adapted for topical administration. Such carriers include creams, ointments, lotions, pastes, jellies, sprays, aerosols, bath oils, or other pharmaceutical carriers which accomplish direct contact between a halogenated derivative of flosequinan (or a combination of halogenated flosequinan derivatives) and the pore of the skin. In general pharmaceutical preparations may comprise from about 0.001% to about 10%, and preferably from about 0.01 to 5% by w/w of the active compound [e.g., a halogenated derivative of flosequinan (or a combination of halogenated flosequinan derivatives)] in a suitable carrier. In some cases it may be necessary to dissolve the active compound in an appropriate solvent such as ethanol or DMSO (dimethylsulfoxide), and the like, to facilitate incorporation into a pharmaceutical preparation.

While the present invention is not limited by a specific method of introducing (as a cardiovascular therapeutic) a halogenated derivative of flosequinan by injection, injection of a halogenated derivative of flosequinan (or a combination of halogenated flosequinan derivatives) can be carried out by any conventional injection means (e.g., employing an hypodermic syringe and needle or a similar device such as the NovolinPen. sold by Squibb-Novo, Inc., Princeton, N.J., USA). This injection may be by the subject injecting him or herself or by another person injecting the subject.

A halogenated derivative of flosequinan (or a combination of halogenated flosequinan derivatives) can be introduced by injection in a physiologically acceptable composition. Such compositions are aqueous solutions that are physiologically acceptable for administration by injection. The physiologically acceptable carrier is selected such that it is not painful or irritating upon injection. The physiologically acceptable compositions will preferably be sterile at the time of administration by injection.

Among the physiologically acceptable compositions for use in the methods is physiological saline or phosphate buffered saline, in which a halogenated derivative of flosequinan (or a combination of halogenated flosequinan derivatives) are dissolved or suspended, such that the resulting composition is suitable for injection. Such a physiologically acceptable composition can also include a non-irritant preservative, such as, e.g., benzalkonium chloride at 0.05% (w/v) to 0./2% (w/v). As the skilled artisan will understand, there are numerous non-toxic salts of VIP, PHM and alpha adrenergic blockers that can be employed in a physiologically acceptable composition for use in the methods herein, including, among others, the chloride, bromide, acetate, sulfate, and mesylate salts.

The present invention is not limited to the method of injecting the a halogenated derivative of flosequinan or a combination of halogenated flosequinan derivatives, as a cardiovascular therapeutic. In selected embodiments, however, it is contemplated that these compounds will be injected with a standard syringe. One skilled in the art would be capable of injecting a halogenated derivative of flosequinan (or a combination of halogenated flosequinan derivatives) with a carrier as described above.

In view of the above, some embodiment of the present invention contemplate methods for the treatment human cardiovascular disease by the administration of a halogenated derivative of flosequinan (or a combination of halogenated flosequinan derivatives).

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); L (liters); ml (milliliters); μl (microliters); cm (centimeters); mm (millimeters); μm (micrometers); nm (nanometers); ° C. (degrees Centigrade).

A. Synthesis of Monochloroflosequinan

Example 1

Figure 13:
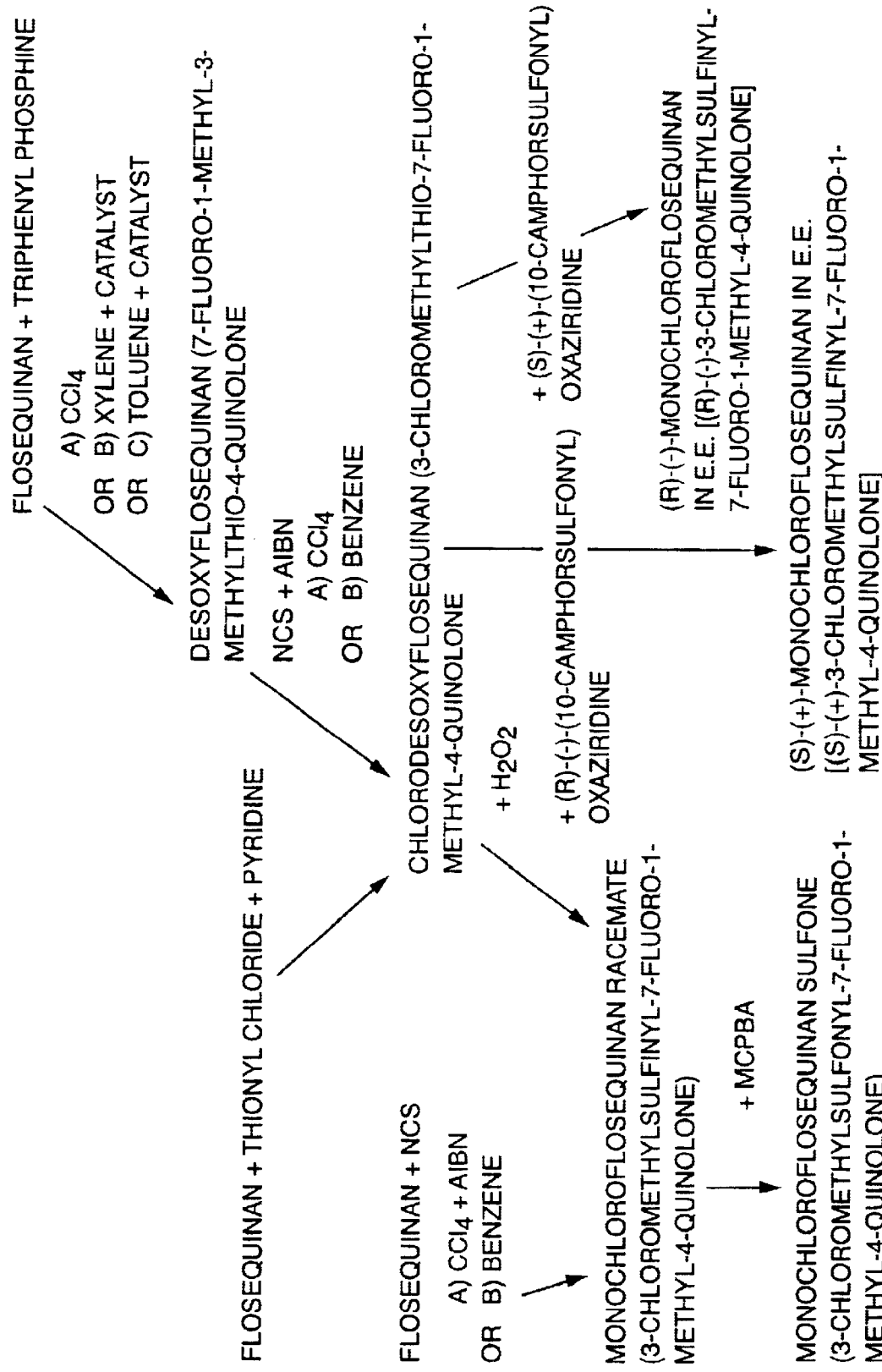
FIG. 13 outlines various chemical reactions described in the description and examples.
Figure 26:
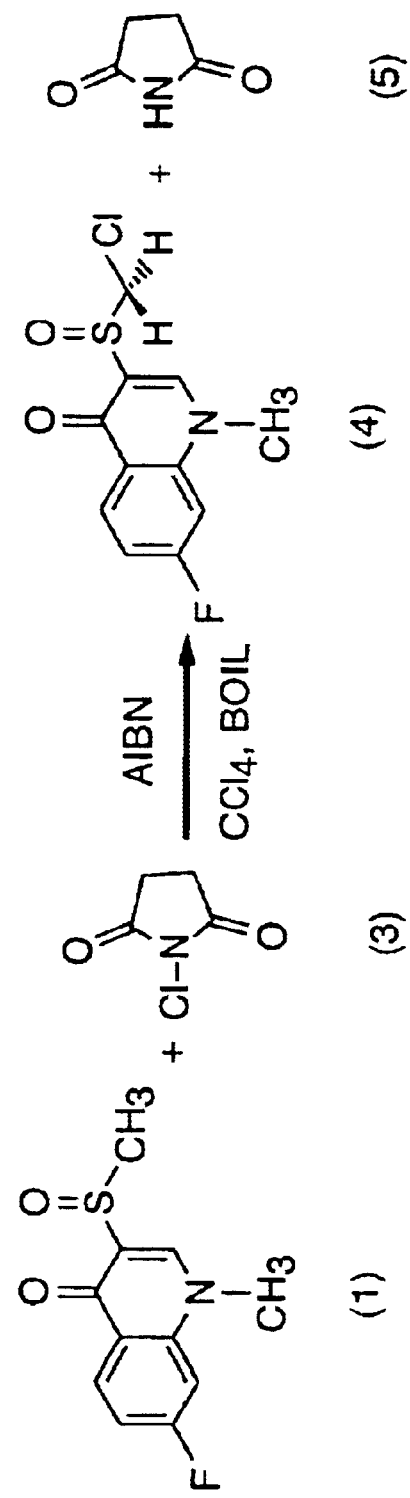
FIG. 26 projects the protocol for the direct chlorination of 7-fluoro-1-methyl-3-methylsulfinyl-4-quinolone (flosequinan).

For reference, FIG. 13 outlines (as a flowchart) the syntheses presented in this section. This example presents a one-step protocol for the synthesis of 3-chloromethylsulfinyl-7-fluoro-1-methyl-4-quinolone (racemic monochloroflosequinan) via the direct chlorination of 7-fluoro-1-methyl-3-methylsulfinyl-4-quinolone (racemic flosequinan) according to the synthetic scheme set out in FIG. 1 and FIG. 26. This overall synthesis is described in more detail according to the following reactions.

900 ml of anhydrous carbon tetrachloride and 25 g (0.015 mol) of 7-fluoro-1-methyl-3-methylsulfinyl-4-quinolone (1) (racemic flosequinan) were placed in a two L, round bottom reaction flask (equipped with a mechanical stirrer, a reflux condenser with gas outlet adapter, a thermometer and a gas inlet adapter in the fourth neck). The reaction flask was then immersed in an oil bath preheated to 95° C. while nitrogen gas was flowed over the reaction mixture (which was gently agitated) at a rate sufficient to prevent the infiltration of air into the reaction mixture. Once this reaction mixture reached a gentle boil, a mixture of N-chlorosuccinimide, compound (3), (15.5 g; 0.116 mole) and 1.1 g of 2,2'-azobisisobutyronitrile (AIBN) was added in five equal portions over 15 minute intervals. The mixture was boiled for an additional 30 minutes. The flask was then cooled to ambient temperature and the precipitated product was collected via filtration through a sintered glass filter. The precipitate was then washed with 50 ml of water, followed by 50 ml of acetone and finally recrystallized from 2.5 L of acetone, yielding 4.416 g of yellow crystals. Another 2.225 g of the product were collected when the first filtrate was concentrated to a volume of 750 ml. In total, 6.64 g (23.1% yield) of 3-chloromethylsulfinyl-7-fluoro-1-methyl-4-quinolone (4) (racemic monochloroflosequinan), of greater than 98% purity (as determined by NMR) were obtained. 1H NMR, $CDCl_3$; δ=3.95 s, 3H, N—$CH_3$; 4.92 dd, 2H, J=11.1 & 7.8 Hz, $CH_2$; 7.18–7.29 m, 2H, H at C6 and C8; 7.95 s, 1H, H at C2; 8.42–8.47 m, 1H, H at C5.

Example 2

Figure 2:
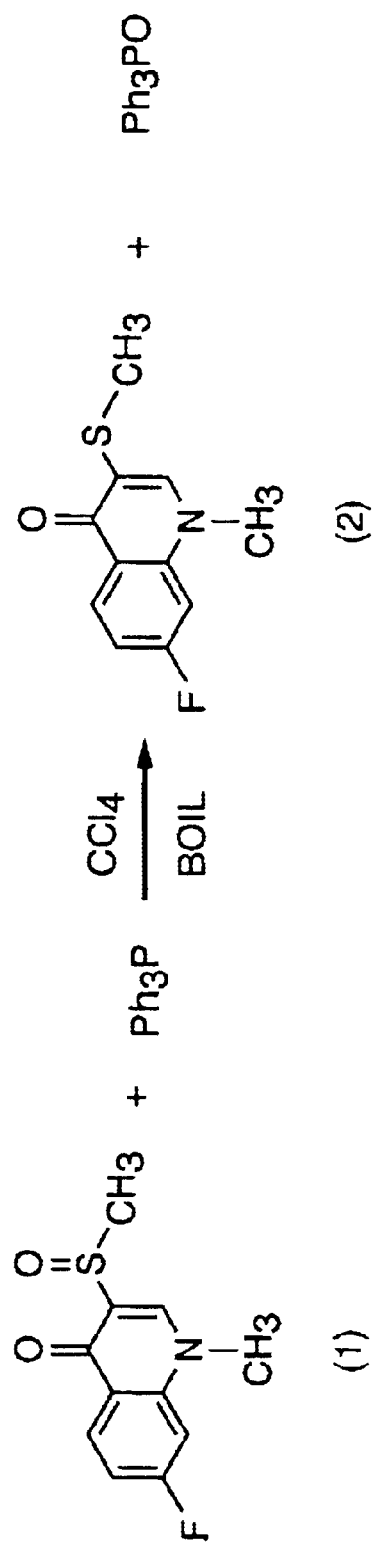
FIG. 2 depicts the first step in a three step protocol for the synthesis of racemic monochloroflosequinan. Triphenylphosphine reduction of flosequinan to 7-fluoro-1-methyl-3-methylthio-4-quinolone (desoxyflosequinan) is depicted.

This example presents an alternative three step protocol for the synthesis of 3-chloromethylsulfinyl-7-fluoro-1-methyl-4-quinolone (racemic monochloroflosequinan) according to the synthetic scheme set out in FIG. 2.

Step 1. Reduction of flosequinan racemate and synthesis of 7-fluoro-1-methyl-3-methylthio-4-quinolone (2) (desoxyflosequinan).

The first step is triphenylphosphine reduction of the flosequinan to 7-fluoro-1-methyl-3-methylthio-4-quinolone (2) (desoxyflosequinan) as depicted schematically in FIG. 2. This reduction is accomplished according to the following protocol.

90 g (0.375 mole) of solid flosequinan racemate (1), 157.5 g (0.6 mole) of triphenyl phosphine ($Ph_3P$) and 3.5 L of carbon tetrachloride ($CCl_4$) were loaded into a 5 L, four neck round bottom flask, equipped with a mechanical stirrer, a thermometer, a reflux condenser with a nitrogen outlet at the top and an inlet for nitrogen. The reaction flask was then placed in an oil bath maintained at a temperature of 85–90° C.

Nitrogen gas then flowed over the reaction mixture at a rate sufficient to prevent the infiltration of air into the reaction mixture, and, thereby, substantially preventing oxidation of the product. The reaction mixture was then stirred and boiled for 2.5 hours. At this time, it was observed that all of the precipitates were dissolved and the color of the reaction mixture changed to an orange brown. The reaction mixture was then cooled to the ambient temperature overnight and the precipitated product was collected on a sintered glass filter. The precipitate was then washed in the filter with two 50 ml aliquots of cold carbon tetrachloride and dried under vacuum of approximately 2.00 mmHg. A 69.3 g of 7-fluoro-1-methyl-3-methylthio-4-quinolone (2) were collected. The approximate 3.5 L of carbon tetrachloride filtrate was concentrated to a final volume of 500 ml. As a result of this concentration an additional 3.3 g of the product (2) were collected. The total yield was 86.4% of 99+% clean (based on NMR spectra). 1H NMR, $CDCl_3$, δ=8.51 dd, 1H, J=6.6 & 9.0 Hz, H at C5; 7.83 s, 1H, H at C2; 7.14 m, 1H, H at C6; 7.05 dd, 1H, J=2.1 & 10.5 Hz, H at C8; 3.79 s, 3H, N—$CH_3$; 2.42 s, 3H, S—$CH_3$.

Step 2. Chlorination of desoxyflosequinan with N-chlorosuccinimide to yield 3-chloromethylthio-7-fluoro-1-methyl-4-quinolone (6) (chlorodesoxyflosequinan).

Figure 3:
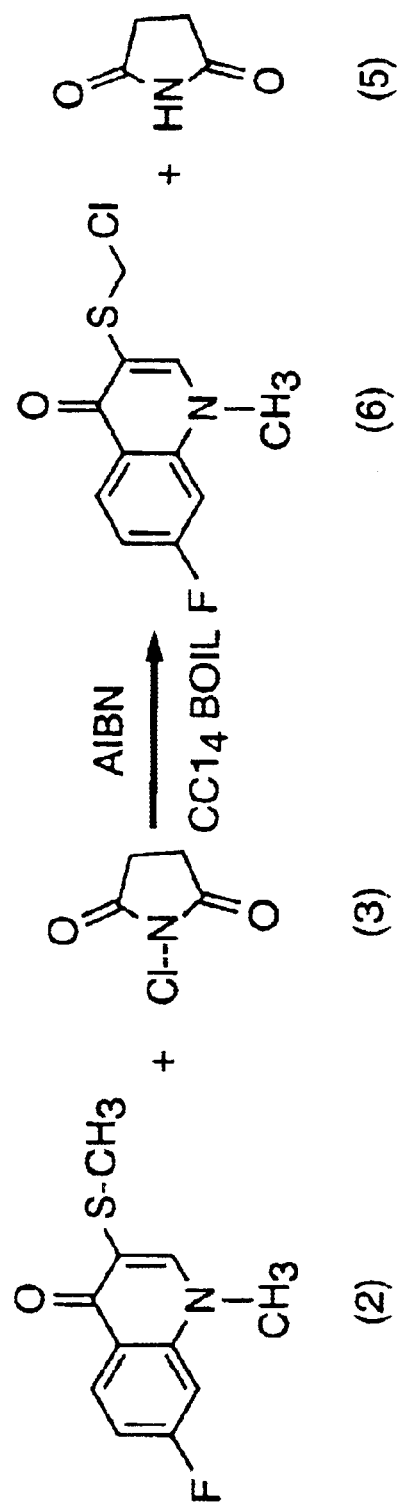
FIG. 3 depicts the second step in a three step protocol for the synthesis of racemic monochloroflosequinan. The chlorination of desoxyflosequinan with N-chlorosuccinimide to yield 3-chloromethylthio-7-fluoro-1-methyl-4-quinolone is depicted.

The reactions in the second step are depicted schematically in FIG. 3. This chlorination is accomplished according to the following protocol.

A solution of 450 mg (2.015 mmol) of 7-fluoro-1-methyl-3-methylthio-4-quinolone (2) (desoxyflosequinan) in 15 ml of carbon tetrachloride was brought to a boil in a round bottom flask. 280 mg (2.097 mmol) of N-chlorosuccinimide (3) with 50 mg of AIBN was added to the desoxyflosequinan and carbon tetrachloride and the resulting mixture was boiled for 6 hours. This solution was evaporated to dryness and the resulting precipitate was then dissolved in 25 ml of ethyl acetate. The solution was washed once with 10 ml of water and twice with 10 ml of brine and concentrated to dryness. The resulting solid was crystallized from 28 ml of acetone yielding 255 mg (49.1% yield) of white crystals of chlorodesoxyflosequinan (6). Chemical purity, based on 1H NMR, was 98+%. 1H NMR, $CDCl_3$, δ=8.50 dd, 1H, J=6.7 & 9.0 Hz, H at C5; 8.01 s, 1H, H at C2; 7.22–7.07 m, 2H, H at C6 and C8; 5.02 s, 2H, $CH_2$; 3.83 s, 3H, N—$CH_3$.

Step 3. Hydrogen peroxide oxidation of 3-chloromethylthio-7-fluoro-1-methyl-4-quinolone (chlorodesoxyflosequinan) to 3-chloromethylsulfinyl-7-fluoro-1-methyl-4-quinolone (4) (monochloroflosequinan).

Figure 4:
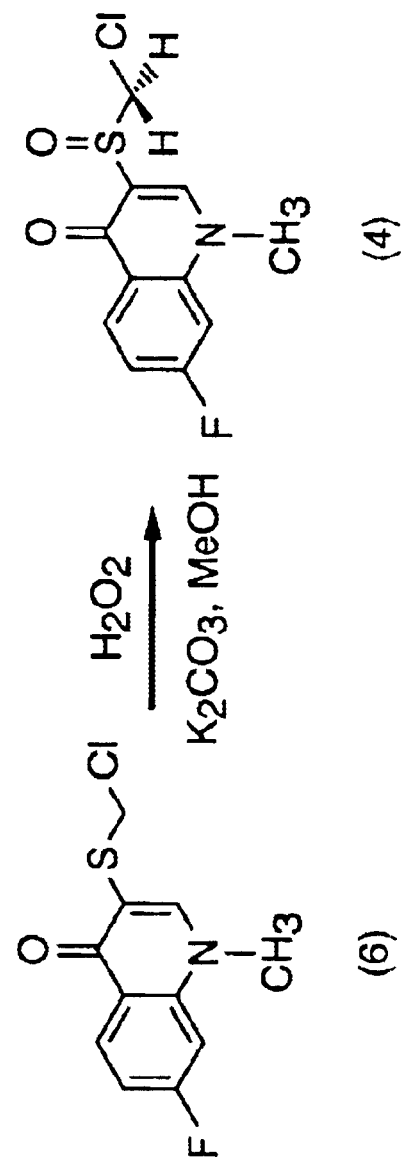
FIG. 4 depicts the third step in a three step protocol for the synthesis of racemic monochloroflosequinan. The hydrogen peroxide oxidation of chlorodesoxyflosequinan to monochloroflosequinan is depicted.

The reactions in the third step are depicted schematically in FIG. 4. This oxidation was accomplished according to the following protocol.

A solution of 250 mg (0.97 mmol) of chlorodesoxyflosequinan in 20 ml of methanol was stirred with 5 ml of 30% hydrogen peroxide and 1.2 g of solid potassium carbonate at ambient temperature overnight. The next day the organic layer was separated and evaporated to dryness yielding 255 mg, (96% yield) of the 97+% (by 1H NMR) clean monochloroflosequinan (4) with an NMR identical with the NMR for monochloroflosequinan synthesized in Example 1.

Example 3

Figure 5:
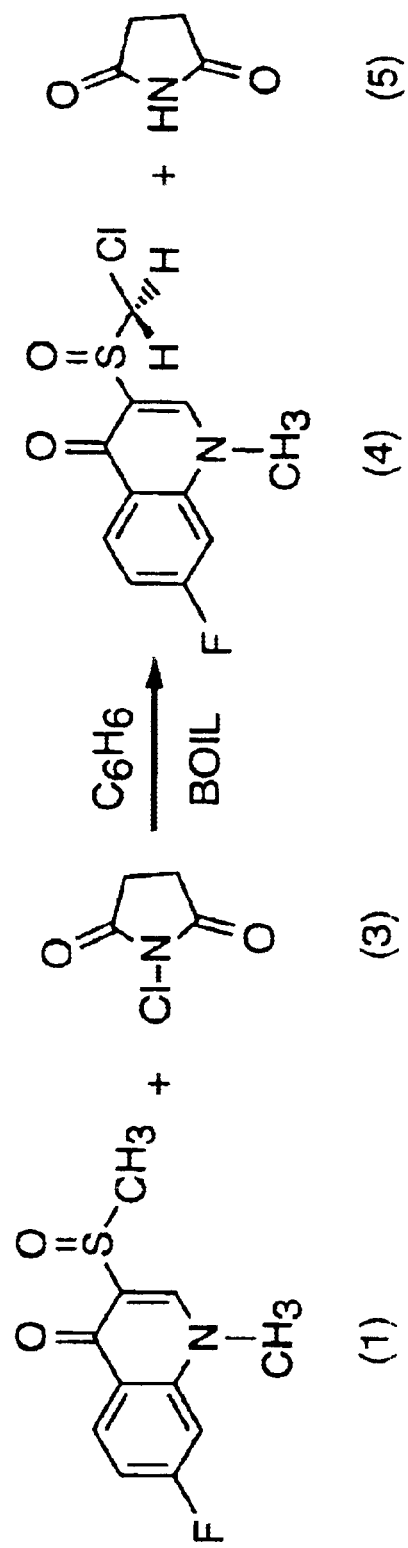
FIG. 5 depicts the synthesis of racemic monochloroflosequinan in an alternative solvent. Flosequinan is reacted as described to produce monochloroflosequinan.

This example presents an alternative solvent used in the synthesis of 3-chloromethylsulfinyl-7-fluoro-1-methyl-4-quinolone (4) (racemic monochloroflosequinan) according to the synthetic scheme set out in FIG. 5. This overall synthesis is described in more detail according to the following reactions.

A mixture of 2.39 g (0.01 mole) of flosequinan (1) and 1.67 g (0.0125 mole) of N-chlorosuccinimide (3) was suspended in 50 ml of anhydrous benzene and placed in a round bottom flask, then stirred and boiled under reflux for 15 minutes. The mixture was cooled to ambient temperature and crystals which precipitated were filtered off and crystallized from 35 ml of anhydrous ethanol, yielding after vacuum drying 2.58 g (94.3% yield) of 98+% clean (by 1H NMR) racemic monochloroflosequinan (4). 1H NMR, $CDCl_3$, δ=8.44 dd, 1H, J=6.0 & 8.7 Hz, H at C5; 7.95 s, 1H, H at C2; 7.29–7.22 m, 1H, H at C6; 7.20 dd, 1H, J=2.1 & 10.2 Hz, H at C8; 4.92 dd, 2H, J=11.1 & 27.0 Hz, $CH_2$; 3.95 s, 3H, N—$CH_3$.

Example 4

Figure 6:
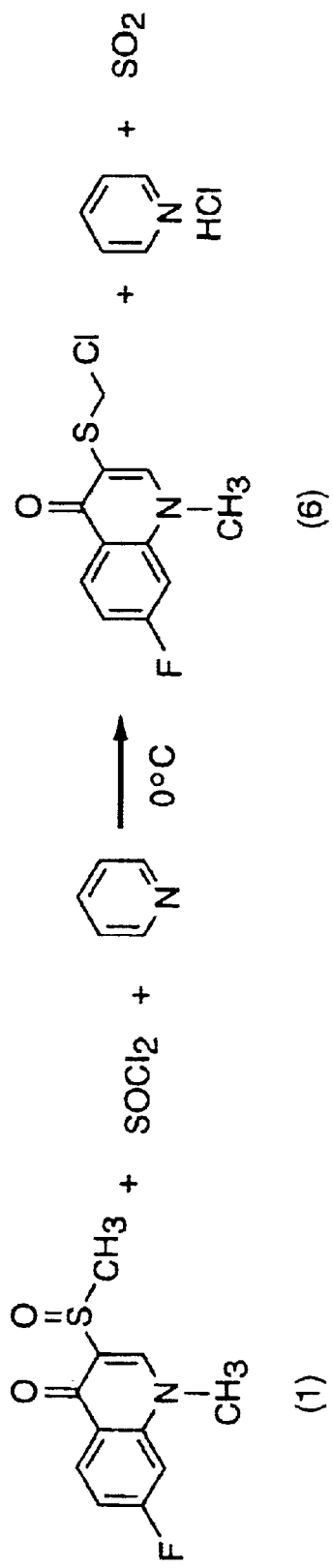
FIG. 6 depicts an alternative protocol for the synthesis of 3-chloromethylthio-7-fluoro-1-methyl-4-quinolone. Racemic flosequinan is reacted as described to produce 3-chloromethylthio-7-fluoro-1-methyl-4-quinolone.

This example presents an alternative protocol for the synthesis of 3-chloromethylthio-7-fluoro-1-methyl-4-quinolone (6) (chlorodesoxyflosequinan) according to the synthetic scheme set out in FIG. 6. This overall synthesis is described in more detail according to the following reactions.

3.59 g (5 mmole) of racemic flosequinan (1) were added (over the course of one minute) to a mixture of thionyl chloride (12 ml) and pyridine (3 ml) with efficient stirring and gentle cooling in a bath of dry ice and acetone, to keep the temperature in the range of 0° C. to 6° C. The mixture was stirred at approximately 0° C. for 5 minutes, cooled to −5° C. and poured as a thin stream into 350 ml of ice-water with efficient stirring. After 10 minutes of stirring at 0° C., a solid was filtered off, washed with water and dried over phosphorous pentoxide, under high vacuum producing 2.82 g (74% yield) of 95% pure (by 1H NMR) 3-chloromethylthio-7-fluoro-1-methyl-4-quinolone (6). 1H NMR, $CDCl_3$, δ=8.50 dd, 1H, J=6.6 & 9.0 Hz, H at C5; 8.01 s, 1H, H at C2; 7.18 ddd, 1H, J=2.1 & 9.0 & 10.2 Hz, H at C6; 7.09 dd, 1H, J=2.1 & 10.2 Hz, H at C8; 5.01 s, 2H, $CH_2$; 3.83 s, 3H, N—$CH_3$.

Example 5

Figure 7:
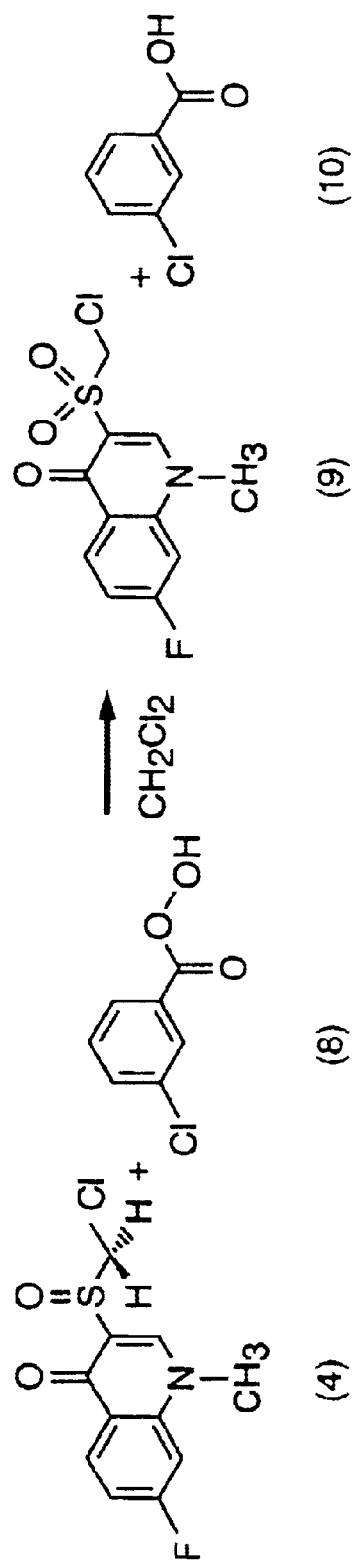
FIG. 7 depicts a protocol for the synthesis of monochloroflosequinan sulfone. Monochloroflosequinan is reacted as described to produce monochloroflosequinan sulfone.

This example presents a protocol for the synthesis of 3-chloromethylsulfonyl-7-fluoro-1-methyl-4-quinolone (9) (monochloroflosequinan sulfone) according to the synthetic scheme set out in FIG. 7. This overall synthesis is described in more detail according to the following reactions.

6.33 g (0.0232 mole) of monochloroflosequinan (4) and 225 ml of methylene dichloride were placed in a 500 ml round bottom flask and stirred. Into this mixture a 5.98 g of 77% pure m-chloroperoxybenzoic acid (8) was added in four equal portions in 15 minute intervals and the mixture was stirred for an additional 30 minutes to complete oxidation. The reaction mixture was then concentrated to a final volume of 100 ml and the crystals which formed were filtered off and washed with two 10 ml portions of methylene dichloride. After high vacuum drying 5.2 g (77.6% yield) of white crystalline 3-chloromethylsulfonyl-7-fluoro-1-methyl-4-quinolone (9) were collected. The product was 99+% pure (by 1H NMR). 1H NMR, $CDCl_3$, δ=8.52 dd, 1H, J=6.3 & 9.0 Hz, H at C5; 8.41 s, 1H, H at C2; 7.20 dd, 1H, J=2.1 & 9.6 Hz, H at C8; 7.32–7.26 m, 1H, H at C6; 5.03 s, 2H, CH$_2$; 3.94 s, 3H, N—CH$_3$.

Example 6

This example presents a protocol for the synthesis and separation of (S)-(+)-3-chloromethylsulfinyl-7-fluoro-1-methyl-4-quinolone and (R)-(−)-3-chloromethylsulfinyl-7-fluoro-1-methyl-4-quinolone.

Figure 8:
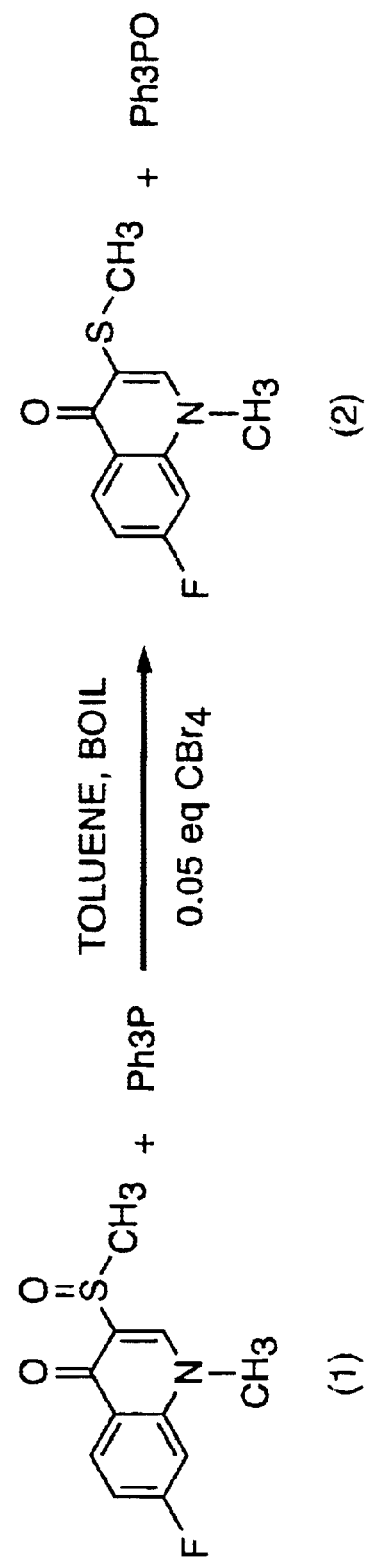
FIG. 8 depicts the first step in the synthesis of e.e. (S)-(+)-3-chloromethylsulfinyl-7-fluoro-1-methyl-4-quinolone and (R)-(−)-3-chloromethylsulfinyl-7-fluoro-1-methyl-4-quinolone. In this step, flosequinan is reacted as described to produce 7-fluoro-1-methyl-3-methylthio-4-quinolone.

A. Catalytical reduction of 7-fluoro-1-methyl-3-methylsulfinyl-4-quinolone. Synthesis of 7-fluoro-1-methyl-3-methylthio-4-quinolone (desoxyflosequinan). (see FIG. 8)

20.0 g (83.6 mmole) of 7-fluoro-1-methyl-3-methylsulfinyl-4-quinolone (1), 25.21 g (96.1 mmole, 1.15 equiv) of triphenylphosphine, 1.39 g (4.2 mmole, 0.05 equiv) of tetrabromomethane and 380 ml of toluene were placed in 500 ml flask equipped in a reflux condenser, and magnetic stirring rod. The mixture was refluxed for one hour and then placed in refrigerator for two hours (at −7° C.). The precipitate which formed was filtered off and washed two times with 25 ml of cold ethyl alcohol and finally vacuum dried yielding 14.75 g (82.7% yield) of 7-fluoro-1-methyl-3-methylthio-4-quinolone (2).

$^1$H NMR, CDCl$_3$, δ=8.512 dd, 1H, J=6.3 & 9.0, H at C5; 7.82 s, 1H, H at C2; 7.14 m, 1H, H at C6; 7.03 dd, 1H, J=2.4 & 10.5 Hz, H at C8; 3.783 s, 3H, N—CH$_3$; 2.427 s, 3H, S—CH$_3$.

Figure 9:
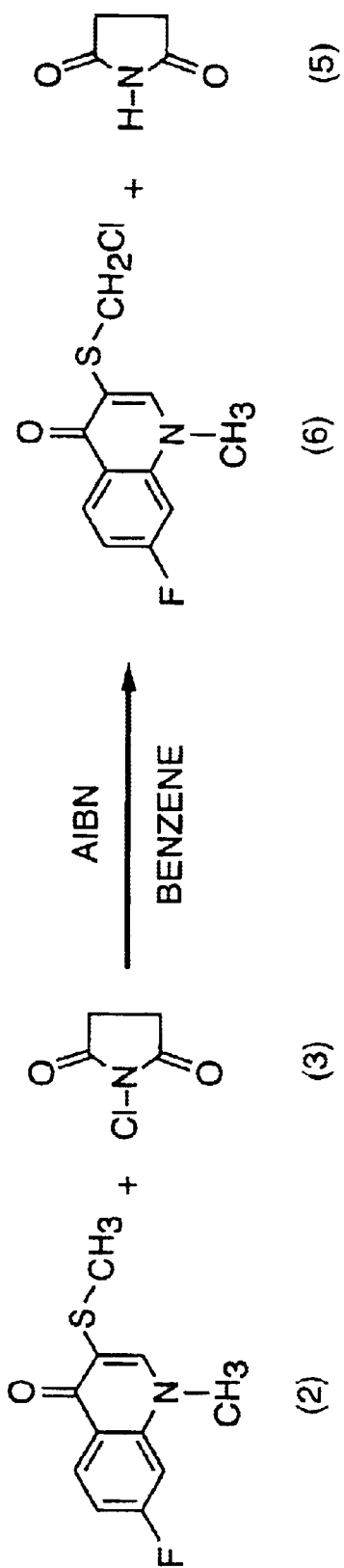
FIG. 9 depicts the second step in the synthesis of e.e. (S)-(+)-3-chloromethylsulfinyl-7-fluoro-1-methyl-4-quinolone and (R)-(−)-3-chloromethylsulfinyl-7-fluoro-1-methyl-4-quinolone. In this step, 7-fluoro-1-methyl-3-methylthio-4-quinolone is chlorinated as described to produce 3-chloromethylthio-7-fluoro-1-methyl-4-quinolone.

B. NCS chlorination of 7-fluoro-1-methyl-3-methylthio-4-quinolone. Synthesis of 3-chloromethylthio-7-fluoro-1-methyl-4-quinolone (chlorodesoxyflosequinan). (see FIG. 9)

12.67 g (56.76 mmol) of 7-fluoro-1-methyl-3-methylthio-4-quinolone (2) and 300 ml of benzene were added into a 500 ml round-bottomed flask and refluxed. Into this boiling solution, a mixture of 9.1 g (68.12 mmol, 1.2 equiv) N-chlorosuccinimide (NCS) (3) and 900 mg of 2,2$^1$-Azobisisobutyronitrile (AIBN) was added in three equal portions every five minutes. After 25 minutes of boiling, the mixture was extracted three times with 50 ml portions of water and the upper-organic layer was concentrated to dryness. The product was transferred on a filter with a total of 50 ml of ethylacetate and vacuum dried yielding 14.91 g (92.7% yield) of yellow crystals of 3-chloromethylthio-7-fluoro-1-methyl-4-quinolone (6).

$^1$HNMR, CDCl$_3$, δ=8.519 dd, J=6.3 & 9.0 Hz, H at C5; 8.017 s, 1H, H at C2; 7.215 m, 1H, H at C6; 7.102 dd, 1H, J=2.7 & 10.5 Hz, H at C8; 5.019 s, 2H, CH$_2$; 3.828 s, 3H, NCH$_3$.

C. Stereopreferred oxidation of 3-chloromethylthio-7-fluoro-1-methyl-4-quinolone. Synthesis of (R)-(−)-3-chloromethylsulfinyl-7-fluoro-1-methyl-4quinolone.

Figure 10:
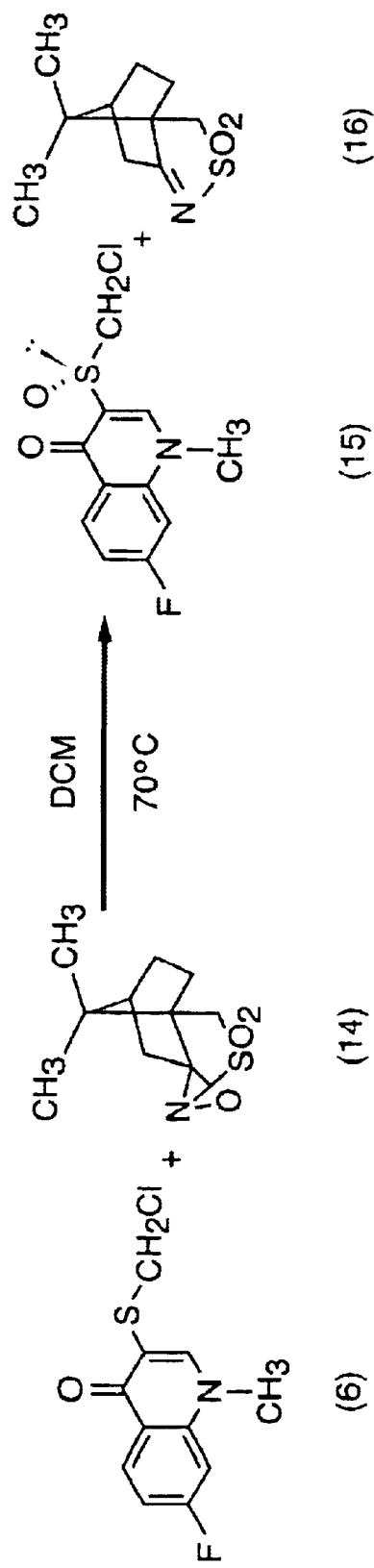
FIG. 10 depicts the stereopreferred oxidation of 3-chloromethylthio-7-fluoro-1-methyl-4-quinolone to produce (R)-(−)-3-chloromethylsulfinyl-7-fluoro-1-methyl-4-quinolone.

7.0 g (27.16 mmol) of 3-chloromethylthio-7-fluoro-1-methyl-4-quinolone (6), 7.47 g (30.45 mmol, 1.12 equiv) of (S)-(+)-(10-camphor sulfonyl) oxaziridine (14) and 100 ml of dichloromethane were placed in a 250 ml pressure flask equipped with a magnetic stirring rod. The flask was tightly closed and placed in an oil bath of 70° C. for 72 hours. After this time the flask was cooled and examined for the presence of the substrates (see FIG. 10). Less than 15% of nonreacted chloromethylthio substrate and no oxaziridine were detected by $^1$H NMR spectroscopy. The dichloromethane solution was concentrated to dryness and crystallized from 100 ml of diethylketone:acetic acid/10:1 mixture to afford 4.36 g of clean (+)-(10-camphor sulfonyl)imine (16). The filtrate was concentrated again and the residue crystallized from 80 ml of anhydrous ethyl alcohol, yielding a mixture of 2.524 g, 37.2% e.e. of (R)-(−)-3-chloromethylsulfinyl-7-fluoro-1-methyl-4-quinolone (15) with 1.1 g of (+)-(10-camphorsulfonyl)imine (16).

The filtrate was concentrated to dryness yielding a mixture composed of: 3.2 g of 79% e.e. (R)-(−)-3-chloromethylsulfinyl-7-fluoro-1-methyl-4-quinolone, 0.88 g of unreacted 3-chloromethylthio-7-fluoro-1-methyl-4-quinolone, 0.7 g of unidentified by product and 2.1 g of (+)-(10-camphorsulfonyl)imine.

This mixture was chromatographed on silica gel column (55 cm+2 cm) using 0.5% methyl alcohol in dichloromethane as eluent. Fraction with R$_f$ value 0.4 were pooled together, concentrated to dryness and crystallized from 45 ml of diethylketone yielding 465 mg of 95.2% e.e. (R)-(−)-3-chloromethylsulfinyl-7-fluoro-1-methyl-4-quinolone. The ratio of (−) to (+) enantiomers was based upon HPLC analysis using:

Column: Chiracel OD-H (15 cm+4.6 mm, 5 μm particle size)

Eluent: Methyl alcohol

This product specific rotation $[\alpha]_D^{20}$=−460.0° was measured in CHCl$_3$ for 1 g/100 ml concentration.

$^1$H NMR, CDCl$_3$, δ=8.47 dd, 1H, J 6.3 & 8.7, H at C5; 7.947 s, 1H, H at C2; 7.264 m, 1H, H at C6; 7.210 dd, 1H, J=2.7 & 10.5, H at C8; 4.923 AB, 2H, J=12.0 & 28.2 Hz, CH$_2$; 3.947 s, 3H, NCH$_3$.

The absolute configuration of the (−)-enantiomer of monochloroflosequinan was determined by X-ray crystallography.

D. Stereopreferred oxidation of 3-chloromethylthio-7-fluoro-1-methyl-4-quinolone. Synthesis of (S)-(+)-3-chloromethylsulfinyl-7-fluoro-1-methyl-4-quinolone.

Figure 11:
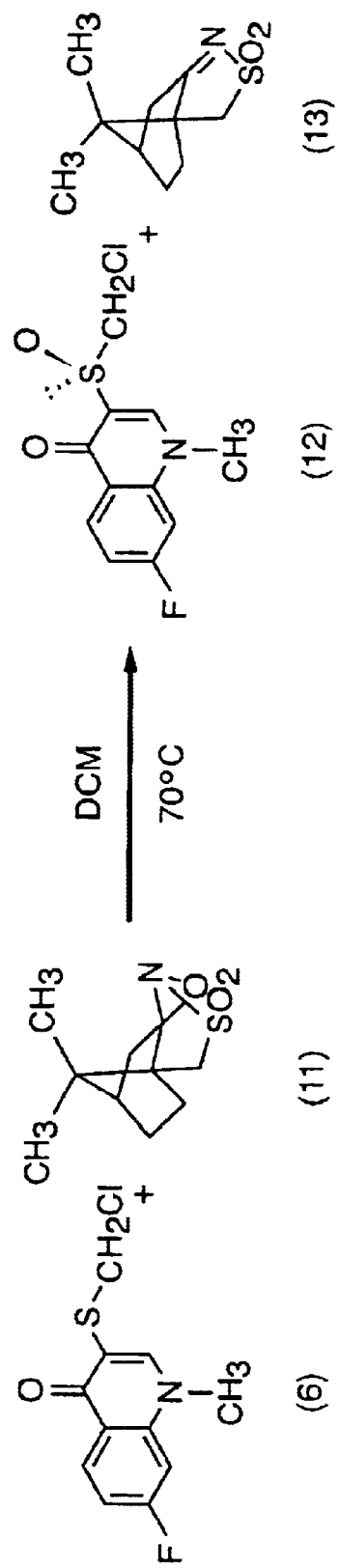
FIG. 11 depicts the stereopreferred oxidation of 3-chloromethylthio-7-fluoro-1-methyl-4-quinolone to produce (S)-(+)-3-chloromethylsulfinyl-7-fluoro-1-methyl-4-quinolone.

7.0 g (27.16 mmol) of 3-chloromethylthio-7-fluoro-1-methyl-4-quinolone (6), 7.47 g (30.45 mmol, 1.12 equivalent) of (R)-(−)-(10-camphorsulfonyl) oxaziridine (11) and 200 ml of dichloromethane were placed in a 250 ml pressure flask equipped with a magnetic stirring rod. The flask was tightly closed and placed in an oil bath of 70° C. for 72 hours. After cooling to ambient temperature, the reaction mixture was concentrated to dryness and crystallized from 88 ml 1:10 mixture of ethylacetate and diethylketone. 1.2 g of 75% e.e. (S)-(+)-3-chloromethylsulfinyl-7-fluoro-1-methyl-4-quinolone (12) in a mixture with 2.5 g of (−)-(10-camphorsulfonyl)imine (13) were collected (see FIG. 11).

This mixture was separated using silica gel column (55 cm+2 cm). The imine was eluted first with 1% acetic acid in dichloromethane solution, while the product stayed absorbed on silica. Solution of (S)-(+)-3-chloromethylsulfinyl-7-fluoro-1-methyl-4-quinolone required 1:10 mixture of methyl alcohol and dichloromethane. Fractions containing (S)-(+)-3-chloromethylsulfinyl-7-fluoro-1-methyl-4-quinolone were pooled together yielding 770 mg of 87.5% e.e. material.

Final crystallization from 8 ml of ethyl acetate-diethylketone/1:10 mixture provided 503 mg of 96% e.e. (S)-(+)-3-chloromethylsulfinyl-7-fluoro-1-methyl-4-quinolone. The ratio of (+) to (−) enantiomers was based upon HPLC analysis using:

Column: Chiracel, OD-H(15 cm + 4.6 mm, 5 μm particle size)
Eluent: Methyl alcohol This product specific rotation $[\alpha]_D^{20}$=+526° was measured in CHCl$_3$ for 1 g/100 ml concentration.

The absolute configuration of the (+)-enantiomer of monochloroflosequinan was determined by X-ray crystallography.

Example 7

This example presents an alternative solvent for the catalytical reduction of flosequinan racemate (1) and synthesis of 7-fluoro-1-methyl-3-methylthio-4-quinolone (desoxyflosequinan) (2).

Figure 12:
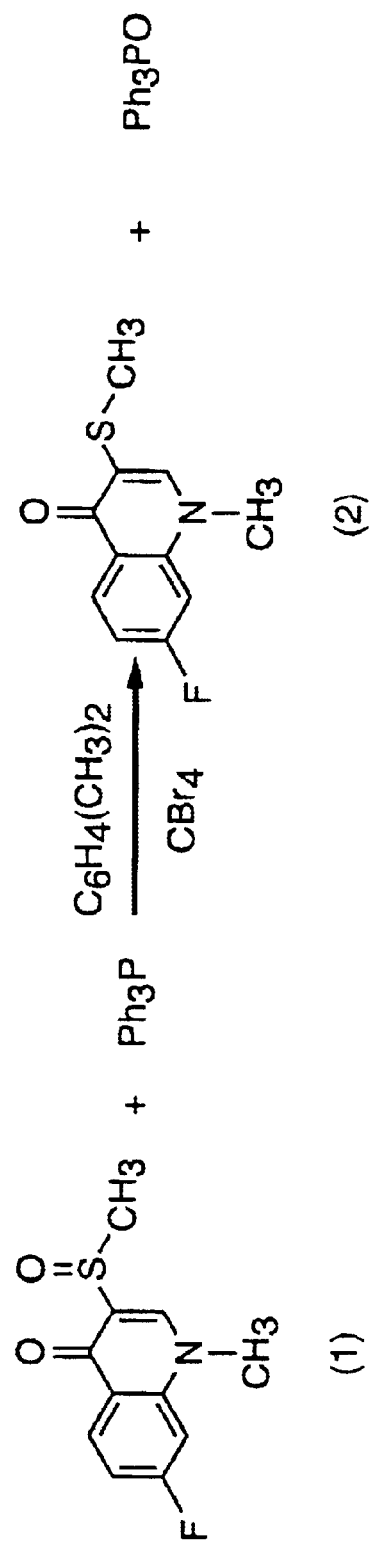
FIG. 12 depicts the use of an alternative solvent (anhydrous xylene) in the reduction of flosequinan to 7-fluoro-1-methyl-3-methylthio-4-quinolone (desoxyflosequinan).

FIG. 12 projects another scheme, using alternative solvents, for the reduction of flosequinan racemate (1) and synthesis of 7-fluoro-1-methyl-3-methylthio-4-quinolone (2). In this example, a 3.0 L round bottomed flask (with three necks) was equipped with a magnetic stirrer, a thermometer and an inlet of nitrogen. Into this flask was placed 2.0 L of anhydrous xylene [$C_6H_4(CH_3)_2$], 105 g (0.439 mole) of racemic flosequinan, 144 g (0.549 mole, 1.25 equivalent) of triphenylphosphine and 14.6 g (0.044 mole, 0.1 equivalent) of carbon tetrabromide ($CBr_4$). Nitrogen gas was then flowed over the reaction mixture at a rate sufficient to prevent the infiltration of air into the reaction mixture. The reaction mixture was stirred and heated to 100° C. for one hour. After this time the mixture was cooled to 10° C. and the product which precipitated was filtered off and washed with two 50 ml portions of xylene and subsequently dried under vacuum to yield 54.58 g of 98+% 7-fluoro-1-methyl-3-methylthio-4-quinolone (2).

The approximately 2.0 L of xylene filtrate was then concentrated (by evaporation) to the volume of 1.0 L, thereby, yielding additional 7-fluoro-1-methyl-3-methylthio-4-quinolone (2) crystals. These crystals were recrystallized from 150 g of ethanol to produce an additional 10.57 g of 98+% 7-fluoro-1-methyl-3-methylthio-4-quinolone, thereby, increasing the combined yield to a total of 65.15 g of 7-fluoro-1-methyl-3-methylthio-4-quinolone (2) which corresponded to a 66.4% yield.

1H NMR, CDCl3, δ: 8.52 dd, 1H J=6.6&9.0 Hz, H-5; 7.89 s, 1H H-2; 7.15 ddd, 1H, J=2.4 & 8.1 & 9.0 Hz, H-6; 7.08 dd, 1H, J=2.1 & 10.2 Hz, H-8; 3.81 s, 3H, NCH₃; 2.43 s, 3H, SCH₃.

Example 8

In this example racemic flosequinan is prepared according to the following protocol:

A. Preparation of Racemic Flosequinan i. Step I

In a clean and dry 12 L glass reactor equipped with a back suction trap plus a NaOH (25%) trap at the outlet and a back suction trap in the inlet, 3.840 L of toluene were charged and cooled to −45° C. using a dry ice-acetone bath. Using appropriate safety precautions, 832 g of phosgene were then passed through the cold toluene while stirring to prepare a 20% (wt/wt) solution. The addition of the phosgene took approximately 3.5 hours.

Separately, into a clean and dry 22 L glass reactor equipped with the above-described types of back suction traps, 399 g of starting material (formula I):

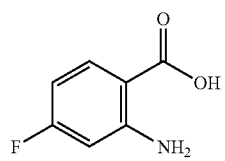

I was added with stirring to 4.37 L of deionized water. A separate 6.8% solution of sodium carbonate in water was also prepared by adding 297 g of sodium carbonate to 4.37 L of deionized water. Using a clean addition funnel, the sodium carbonate solution was then slowly added with stirring to the suspension of the starting material, to create a brown-colored solution.

In preparation for the reaction step, the phosgene solution was warmed from −45° C. to −15° C. and the mixture of the starting material and the sodium carbonate was cooled to 10° C. The phosgene solution was then added over approximately 1.5 hours with stirring to the brown solution. The reaction mixture was stirred overnight allowing the desired intermediate-A (formula II):

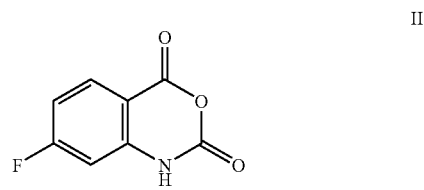

II to precipitate out. A sample was removed for NMR assessment and the precipitate was filtered on a 4 L sintered glass funnel. The filtrate was washed with 2×500 ml aliquots of cold deionized water and dried under a vacuum at approximately 50° C. for 16 hours.

A 93.4% lot yield of 435 g of intermediate-A (formula ") was obtained. This procedure was repeated three more times, starting with approximately 400 g of starting material each time. Lot yields of 448 g (94.5%), 449 g (95.9%), and 459 g (96.8%) were obtained.

ii. Step II

In a 22 L oven dried glass reactor equipped with a reflux condenser, addition funnel and temperature recorder, 11.40 L of anhydrous tetrahydrofuran (THF) were added under nitrogen. To this reactor were also added 409 g of 60% sodium hydride in oil. Eight approximately equal portions of intermediate-A (formula II were then added to the reactor, totaling 883 g altogether. As this reaction is exothermic, care was taken to avoid excessive heat and bubbling. Final temperature was 40° C., with a maximum observed temperature of 41° C. The reaction mixture was stirred until hydrogen gas evolution ceased.

To the reaction mixture was then slowly added 575 ml (766.4 g) of dimethyl sulfate, keeping the temperature below 50° C. Upon completion, the reaction mixture was stirred at 50° C. for 3 hours with the reflux condenser on. A sample was removed for NMR assessment, and the heat was turned off before stirring overnight.

In the morning, the stirring was stopped and the clear liquid on top was siphoned off. This liquid was filtered using a 2–3 inch thick Celite pad in a 2 L sintered glass funnel. The residue cake was kept covered to minimize contact with atmospheric moisture. The residue was collected and washed with 4 aliquots of anhydrous THF. The filtrate and the washings were evaporated to dryness using a rotary evaporator and the residue obtained was dried under vacuum at approximately 36–38° C. overnight. A sample was removed for NMR assessment of the amount of unreacted dimethyl sulfate present. The dried residue was then added to 1600 ml of a 1:3 toluene:hexane mixture and vigorously stirred. This mixture was then filtered and washed with 2×700 ml washings of 1:3 toluene:hexane mixture. A reference sample was removed for NMR assessment and the residue was dried at 51–50° C. under vacuum for 36 hours.

This batch yielded 871 g of intermediate-B (formula III):

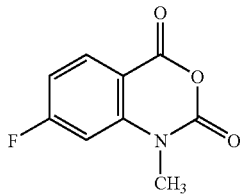

for a lot yield of 91.6%. Another 907.1 g of intermediate-A was subjected to the procedure of step II, in which the amounts of reactants and solvents was proportionately adjusted with a yield of 850 g (87%).

iii. Step III

In an oven dried 12 L glass reactor equipped with a stirrer, temperature recorder and addition funnel, 2550 ml of anhydrous toluene was added under nitrogen. Then 236 g of 60% sodium hydride in oil was added, all at room temperature. The reaction mixture was heated with continuous stirring to 75° C. using a heating mantel. Then 1.59 L of anhydrous dimethyl sulfoxide (DMSO) were added slowly and carefully over 45 minutes taking care to avoid excessive bubbling. The reaction mixture was stirred for one hour at 70–72° C. until clear and hydrogen gas evolution ceased. The heating mantel was turned off and a water bath was used to cool the reaction mixture to 30° C.

To this mixture, 538.2 g of dry intermediate-B (formula III) was added slowly in portions, keeping the temperature no higher than 35° C. Then 1.9 L of anhydrous DMSO was added, again keeping the temperature no higher than 35° C. The reaction mixture was stirred under nitrogen for one hour, allowing the mixture to cool to 26° C. The reaction mixture was then quenched slowly and carefully with 320 ml of methanol. The resulting suspension was then added slowly and with vigorous stirring to a 22 L reaction vessel containing 12.760 L of diethyl ether.

After stirring was stopped, the upper ether layer was siphoned off and the brown oil lower layer was washed with 520 ml of fresh ether. The oily yellow residue was triturated with 2600 ml of deionized water until a yellow precipitate formed. This precipitate was filtered using a 2 L sintered glass funnel and the solid residue was washed with three aliquots of 130 ml cold deionized water. A reference sample was taken to assess the residue. The residue was dried under vacuum at 50–53° C. for 23 hours.

This procedure produced 243 g of intermediate C (formula IV):

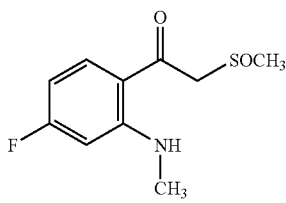

which represents a 38.4% yield. Two other batches of intermediate-B were treated according to this Step III procedure, with proportionate adjustments to the amounts of reactants and solvents. The first additional batch of 538.2 g intermediate-B produced a 192 g (30.4%) yield, and the second additional batch of 87.38 g of intermediate-B produced a yield of 42 g (40.9%).

iv. Step IV

In a 12 L oven dry glass reactor equipped with a stirrer, temperature recorder and addition funnel which has been dried by nitrogen flow for 30 minutes the following chemicals were charged: 7.990 L of triethyl orthoformate; 696 g of intermediate C; 324 ml of piperdine; and 296 ml of acetic acid. The reaction mixture was heated under nitrogen to reflux at approximately 105° C. for 2 hours. A sample was removed to assess the progress of the reaction step by NMR.

Using a water bath, the reaction mixture was then cooled to room temperature and stirred for 30 minutes. The final product precipitated out and was collected by filtration on a 4 L sintered glass funnel. The residue was washed with 3×700 ml aliquots of diethyl ether, and a sample was removed for NMR assessment. The residue was dried under vacuum at 50–51° C. for 17 hours.

A sample of the dried flosequinan product (formula V):

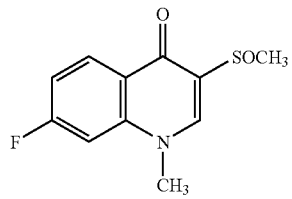

was removed for NMR assessment. 547 g (75.3%) yield of flosequinan was obtained (an additional 47 g of product was scraped from the bottom of the sintered glass filter but was not included in this total yield calculation).

Example 9

In this example, a racemic mixture of monochloroflosequinan and the sulfone derivative of monochloroflosequinan were independently subjected to biochemical enzyme assays to determine their respective percent inhibition of a variety of phosphodiesterases (PDE1–PDE6). The methods used have been adapted from those described in the scientific literature, see Hidaka and Asano "Human blood platelet 3':5' cyclic nucleotide phosphodiesterase. Isolation of low-Km and high Km phosphodiesterase." *Biochem. Biophys. Acta* 429:485 (1976); Nicholoson et al. "Differential modulation of tissue function and therapeutic potential of selective inhibitors of cyclic nucleotide phosphodiesterase isoenzymes" *Trends Pharmacol. Sci.* 12:19 (1991); Cortijo et al. "Investigation into the role of phosphodiesterase IV in bronchorelaxation, including studies with hyman bronchus." *Br. J. Pharmacol.* 108:562 (1993); Baehr et al. "Isolation and characterization of cGMP phosphodiesterase from bovine rod outer segments." *J. Biol. Chem.* 254:11669 (1979) and Gillespie and Beavo "Inhibition and stimulation of photoreceptor phosphodiesterase by dipyridamole and M&B 22,948" *Molecular Pharm.* 36:773 (1989). A brief summary of the conditions for each enzyme assay is provided below:

PDE1: PDE1 partially purified from bovine heart was used. The compounds were independently incubated with 13 μg PDE1 enzyme, 1.01 μM [$^3$H]cAMP+cAMP and CaCl$_2$/calmodulin in Tris buffer pH 7.5 for 20 minutes at either 25° C. or 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE2: PDE2 partially purified from human platelets was used. The compounds were independently incubated with 23 μg PDE2 enzyme, 25.1 μM [$^3$H]cAMP+cAMP in Tris buffer pH 7.5 for 20 minutes at either 25° C. or 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE3: PDE3 partially purified from human platelets was used. The compounds were independently incubated with 13 ug PDE3 enzyme and 1.01 μM [$^3$H]cAMP+cAMP in Tris buffer pH 7.5 for 20 minutes at either 25° C. or 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE4: PDE4 partially purified from human U-937 pronocytic cells was used. The compounds were independently incubated with 20 μg PDE4 enzyme and 1.01 μM [$^3$H] cAMP+cAMP in Tris buffer pH 7.5 for 20 minutes at either 25° C. or 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE5: PDE5 partially purified from human platelets was used. The compounds were independently incubated with 120 μg PDE5 enzyme and 1.01 μM [$^3$H]cGMP+cGMP in Tris buffer pH 7.5 for 20 minutes at either 25° C. or 30° C. The reaction was terminated by boiling for 2 minutes, and the resulting GMP was converted to guanosine by addition of 10 mg/ml snake venom nucleotidase and further incubation at 30° C. for 10 minutes. Unhydrolyzed cGMP was bound to AGI-X2 resin, and the remaining [$^3$H]guanosine in the aqueous phase was quantitated by scintillation counting.

PDE6: PDE6 partially purified from bovine retinal rod outer segments and activated by trypsin was used. The compounds were independently incubated with 0.2 μg/ml active PDE6 and 100 μM [$^3$H]cGMP+cGMP in Tris buffer pH 7.5 for 20 minutes at either 25° C. or 30° C. Each reaction was terminated by boiling for 2 minutes. The resulting GMP was converted to guanosine by addition of 10 mg/ml snake venom nucleotidase, and further incubated at 30° C. for 10 minutes. Unhydrolyzed cGMP was bound to AGI-X2 resin, and [$^3$H]guanosine remaining in the aqueous phase was quantitated by scintillation counting.

Figure 15:
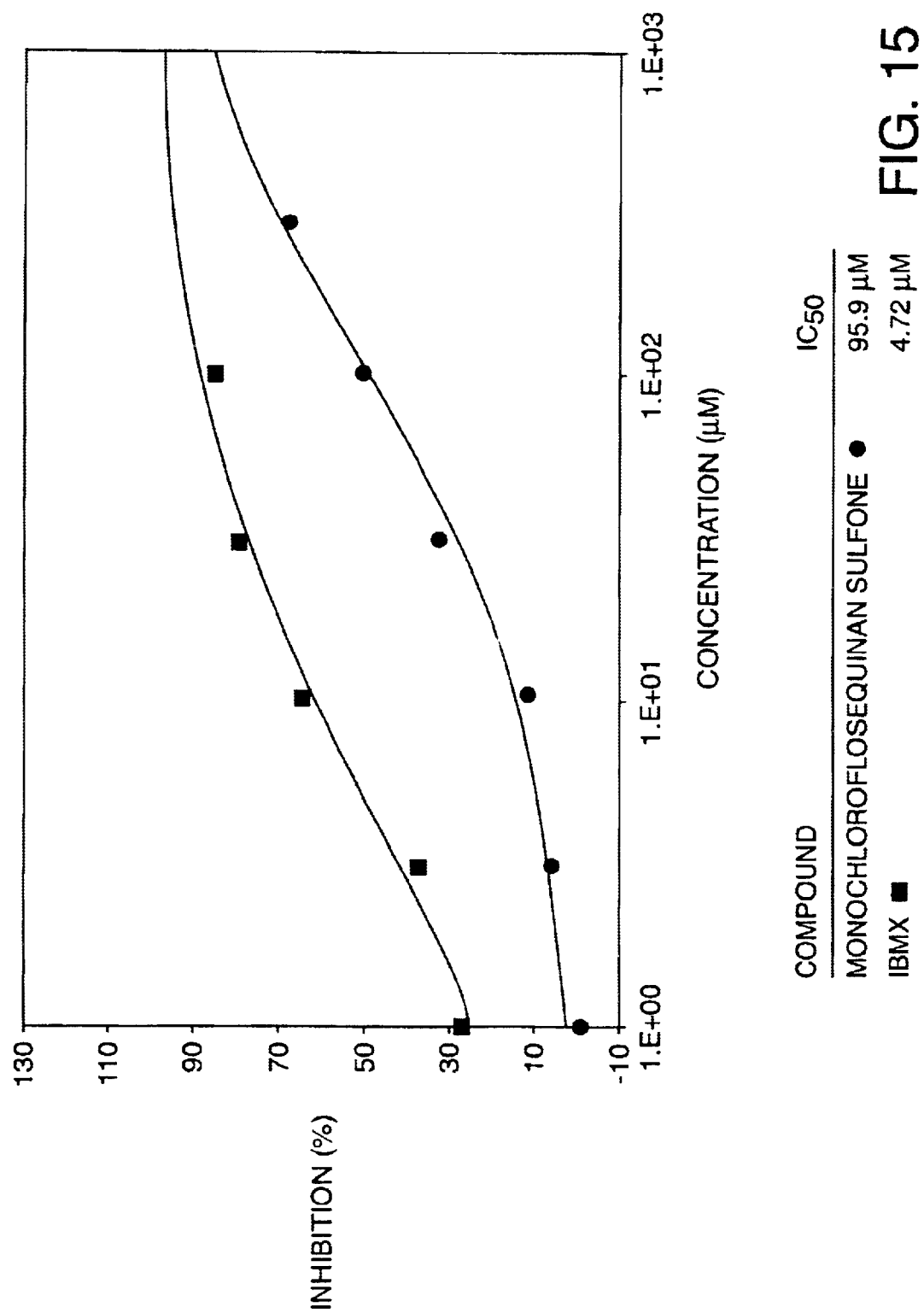
FIG. 15 shows the PDE3 inhibition curves for monochloroflosequinan sulfone (circles) and the reference compound, IBMX (squares).

FIG. 14 shows the results of assays carried out as described above with monochloroflosequinan sulfone. Each PDE was assayed at 25° C. with 100 uM monochloroflosequinan sulfone (in 1% DMSO as the vehicle). Significant inhibition (e.g. greater than 50% inhibition) of PDE3 was observed. PDE3 was also assayed with varying concentrations of monochloroflosequinan sulfone (300 μM, 100 μM, 30 μM, 10 μM, 3 μM and 1 μM) and the IC$_{50}$ was determined to be 95.9 μM (see FIGS. 14 and 15). FIG. 15 shows the inhibition curves for PDE3 for monochloroflosequinan sulfone (circles) and the reference compound, IBMX (squares).

Figure 17:
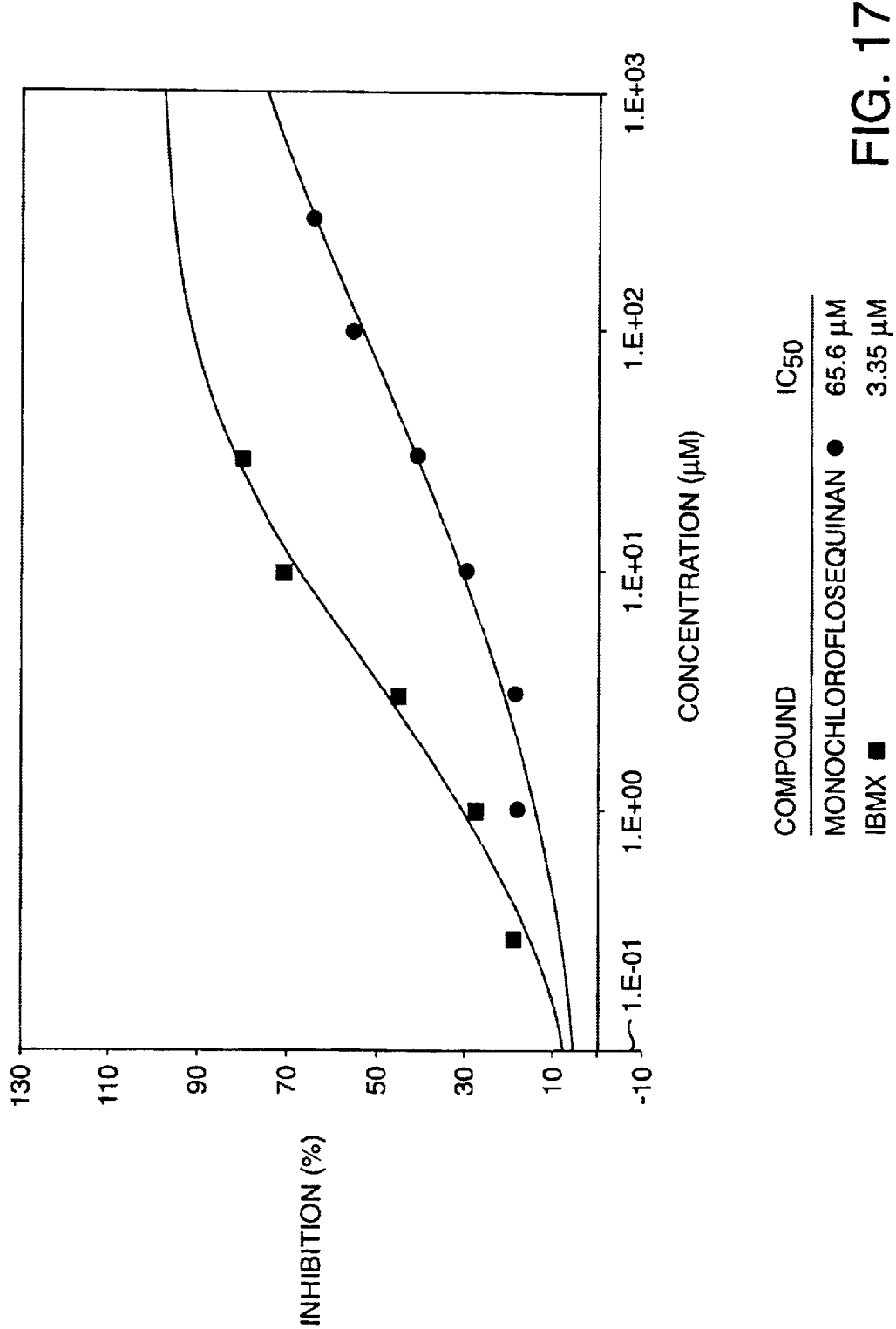
FIG. 17 shows the PDE1 inhibition curves for monochloroflosequinan (circles) and the reference compound, IBMX (squares).
Figure 18:
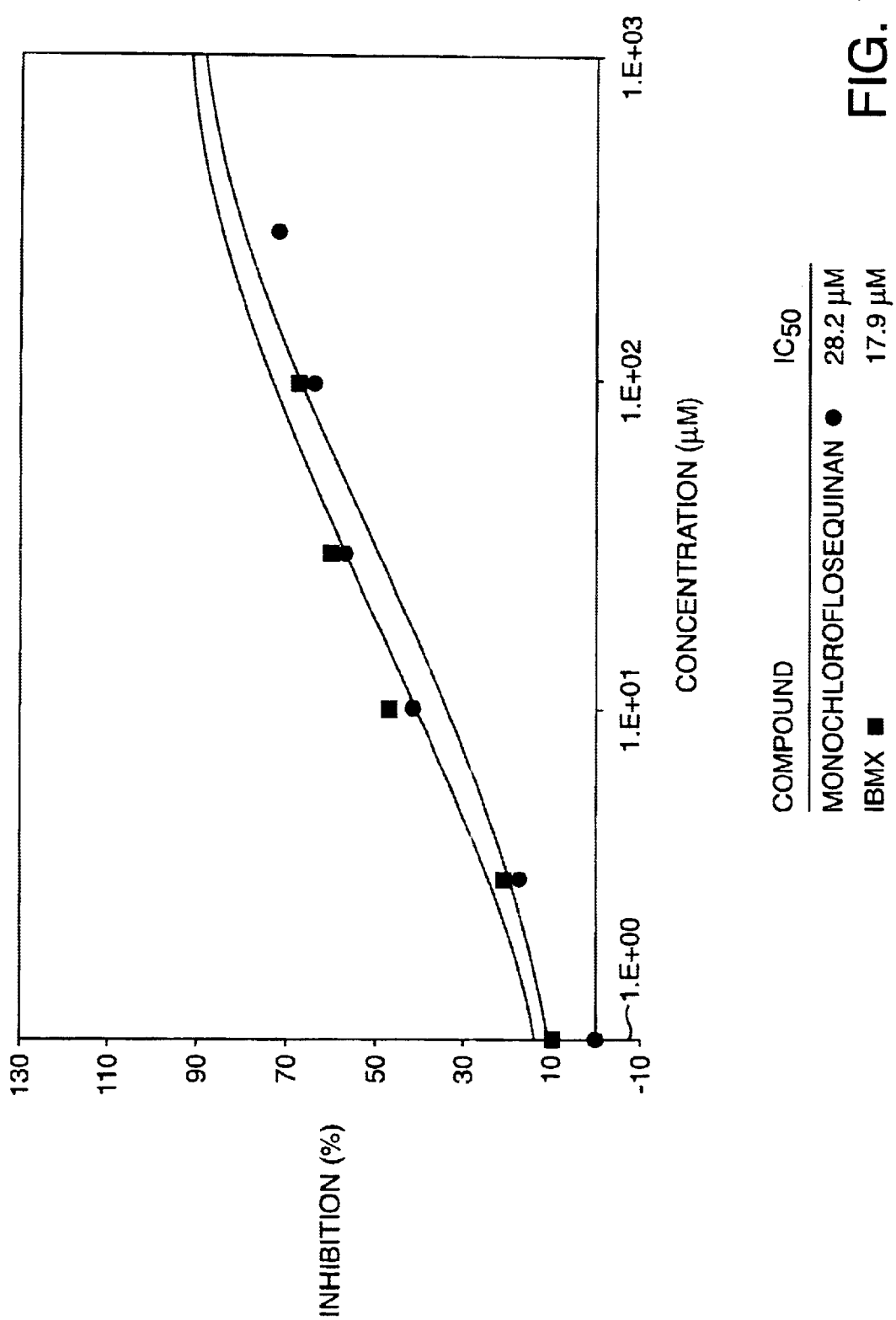
FIG. 18 shows the PDE3 inhibition curves for monochloroflosequinan (circles) and the reference compound, IBMX (squares).

FIG. 16A and FIG. 16B show the results of assays carried out as described above with monochloroflosequinan. Each PDE was assayed at 30° C. with 100 uM monochloroflosequinan (in 1% DMSO as the vehicle). Significant inhibition of PDE1, PDE2 and PDE3 was observed in this assay. PDE1, PDE2 and PDE3 were also assayed with varying concentrations of monochloroflosequinan (300 μM, 100 μM, 30 μM, 10 μM, 3 μM and 1 μM) to determine the respective IC$_{50}$s. The IC$_{50}$ was determined to be 65.6 μM for PDE1, >300 μM for PDE2 and 28.2 μM for PDE3 (See FIGS. 16A, 16B, 17 and 18). FIG. 17 shows the inhibition curves for PDE1 for monochloroflosequinan (circles) and the reference compound, IBMX (squares). FIG. 18 shows the inhibition curves for PDE3 for monochloroflosequinan (circles) and the reference compound, IBMX (squares).

Figure 19:
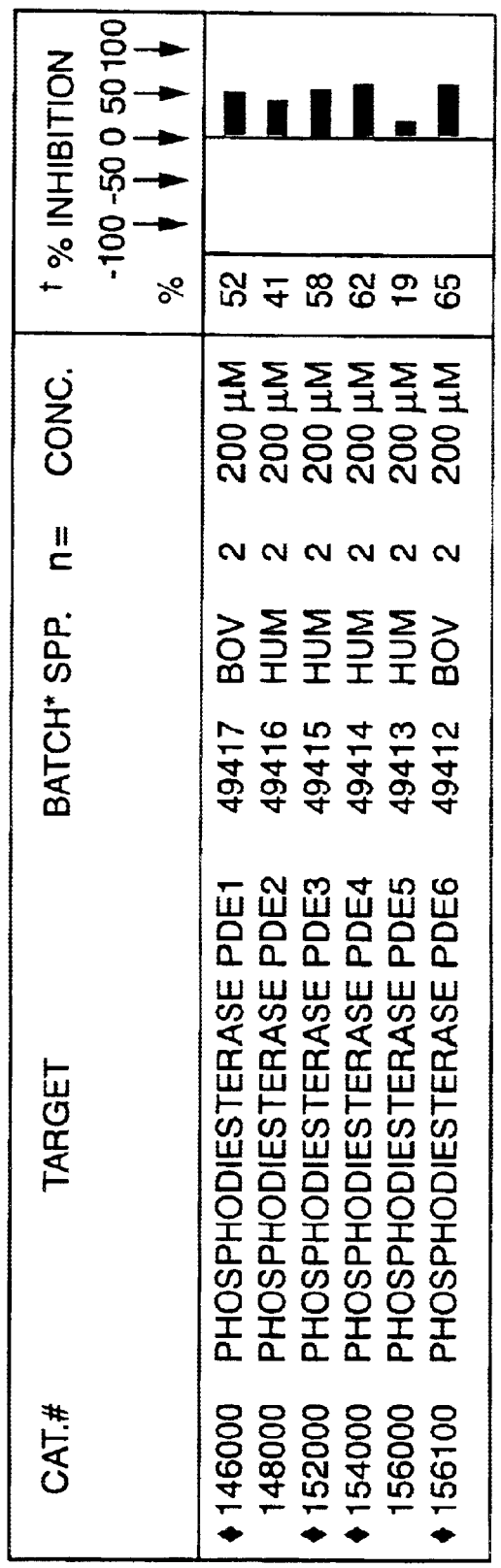
FIG. 19 depicts the results of in vitro phosphodiesterase inhibition assays using the (−)-enantiomer of monochloroflosequinan (i.e. (R)-(−)-3-chloromethylsulfinyl-7-fluoro-1-methyl-4-quinolone).

FIG. 19 shows the results of assays carried out as described above with the (−)-enantiomer of monochloroflosequinan (i.e. (R)-(−)-3-chloromethylsulfinyl-7-fluoro-1-methyl-4-quinolone). Each PDE was assayed at 25° C. with 200 μM of the (−)-enantiomer of monochloroflosequinan (i.e. (R)-(−)-3-chloromethylsulfinyl-7-fluoro-1-methyl-4-quinolone). (in 1% DMSO as the vehicle). Significant inhibition (e.g. greater than 50% inhibition) of PDE1, PDE3, PDE4, and PDE6 was observed in this assay.

Figure 20:
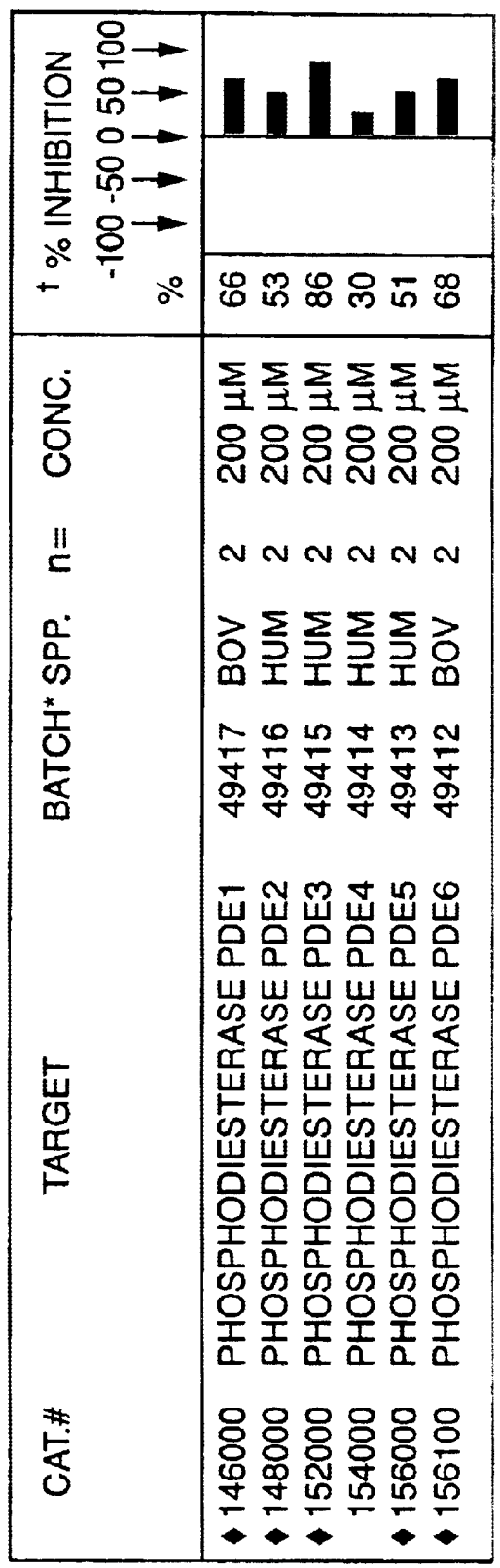
FIG. 20 depicts the results of in vitro phosphodiesterase inhibition assays using the (+)-enantiomer of monochloroflosequinan (i.e. (S)-(+)-3-chloromethylsulfinyl-7-fluoro-1-methyl-4-quinolone).

FIG. 20 shows the results of assays carried out as described above with the (+)-enantiomer of monochloroflosequinan (i.e. (S)-(+)-3-chloromethylsulfinyl-7-fluoro-1-methyl-4-quinolone). Each PDE was assayed at 25° C. with 200 μM of the (+)-enantiomer of monochloroflosequinan (i.e. (S)-(+)-3-chloromethylsulfinyl-7-fluoro-1-methyl-4-quinolone). (in 1% DMSO as the vehicle). Significant inhibition (e.g. greater than 50% inhibition) of PDE1, PDE2, PDE3, PDE5, and PDE6 was observed in this assay.

B. Synthesis of Dichloroflosequinan

Example 10

This example describes one method for the synthesis of dichloroflosequinan. Briefly, 3-dichloromethylthio-7-fluoro-1-methyl-4-quinolone (i.e. Compound 2 of FIG. 21) is first prepared, and used as a reagent to produce 3-Dichloromethylsulfinyl-7-fluoro-1-methyl-4-quinolone (i.e. Compound 3 of FIG. 21) according to the following reactions.

Figure 21:
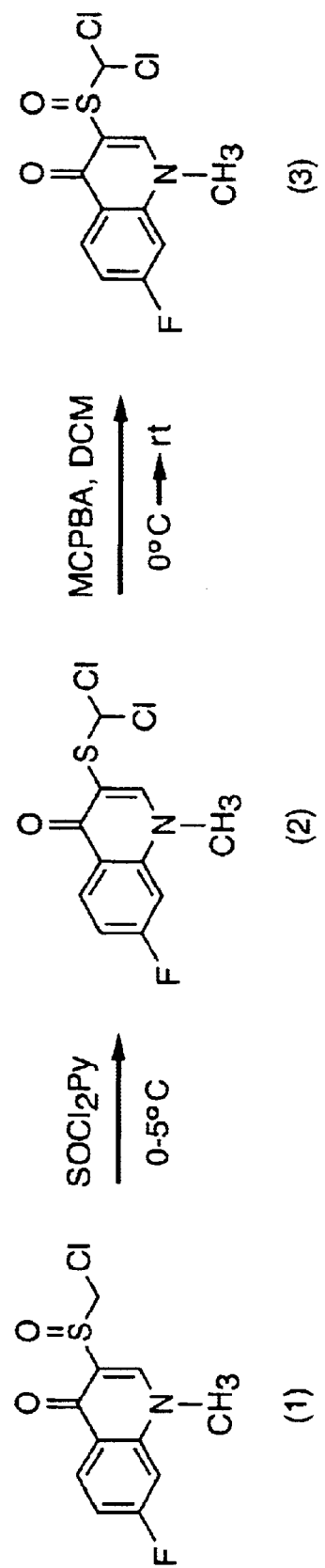
FIG. 21 shows a schematic protocol for the synthesis of dichloroflosequinan.

I. 3-Dichloromethylthio-7-fluoro-1-methyl-4-quinolone (Compound 2 of FIG. 21)

To an efficiently stirred and gently cooled 4.2 ml mixture of thionyl chloride ("SOCl$_2$") and 1.05 ml of pyridine ("Py") at −3° C. was added 1.015 g (3.708 mmol) of 3-chloromethylsulfinyl-7-fluoro-1-methyl-4-quinolone (monochloroflosequinan)(Compound 1 of FIG. 21). This addition was made in multiple alloquots over a period of approximately 1 min. During this addition, cooling was applied to keep the temperature in the range 0–5° C. This mixture was then stirred at 0° C. for 8 min and then cooled to −5° C. The mixture was then poured as a thin stream into, stirring, 120 ml of ice-water. After 10 minutes of stirring at 0° C., a solid was filtered off, washed with water, and dried over phosphorus pentoxide under high vacuum. [Yield: 669 mg (61.7%) of a crude product (i.e. Compound 2) that was approximately 94% pure by $^1$H NMR, CDCl$_3$; d=3.84 s, $^3$H, N—CH$_3$; 7.11 dd, $^1$H, J=10.0 & 2.2 Hz, H at C8, 7.19 ddd, $^1$H, J=8.9, 7.9 & 2.3 Hz, H at C6; 7.24 s, $^1$H, CHCl2; 8.03 s, $^1$H, H at C2; 8.47 dd, $^1$H, J=9.0 & 6.3 Hz, H at C5.]. This product was then, further, purified in Step B described below.

II. 3-Dichloromethylsulfinyl-7-fluoro-1-methyl-4-quinolone 665 mg (2.276 mmol) of the 3-dichloromethylthio-7-fluoro-1-methyl-4-quinolone (Compound 2, FIG. 21), as prepared in Step A, was dissolved in 20 ml of DCM at 0° C. to form a solution. To this solution was added 505.7 mg (2.345 mmol) of 80% MCPBA to form a mixture. This stirred mixture was then allowed to warm to room temperature and was stirred for 1 hour. An additional 25 mg of MCPBA was added and the mixture and stirred for 1 hour. The mixture was washed with 5% aqueous $Na_2CO_3$. The aqueous layer was extracted with DCM, and the combined DCM extracts were dried over anhydrous $Na_2SO_4$ and concentrated. The residue was chromatographed on silica gel with hexane-ethyl acetate (gradient 4:1,2:1,1:1) to give 352 mg (50%) of the product (Compound 3, FIG. 21) as a white solid, that was approximately 98% pure according to $^1H$ NMR, $CDCl_3$; d=3.96 s, $^3H$, N—$CH_3$; 7.09 s, $^1H$, $CHCl_2$; 7.22 dd, $^1H$, J=10.2 & 2.4 Hz, H at C8, 7.27 ddd, $^1H$, J=9.0, 7.6 & 2.2 Hz, H at C6; 8.03 s, $^1H$, H at C2; 8.43 dd, $^1H$, J=8.8 & 6.1 Hz, H at C5. This white solid product was further purified by recrystallization from methanol to give 252 mg of white crystals.

Example 11

In this example flosequinan is prepared according to the protocol in Example 8.

Example 12

In this example, dichloroflosequinan was subjected to biochemical enzyme assays to determine its respective percent inhibition of a variety of phosphodiesterases (PDE1–PDE6). The methods used have been adapted from those described in the scientific literature, see Hidaka and Asano "Human blood platelet 3':5' cyclic nucleotide phosphodiesterase. Isolation of low-Km and high Km phosphodiesterase." *Biochem. Biophys. Acta* 429:485 (1976); Nicholoson et al. "Differential modulation of tissue function and therapeutic potential of selective inhibitors of cyclic nucleotide phosphodiesterase isoenzymes" *Trends Pharmacol. Sci.* 12:19 (1991); Cortijo et al. "Investigation into the role of phosphodiesterase IV in bronchorelaxation, including studies with hyman bronchus." *Br. J. Pharmacol.* 108:562 (1993); Baehr et al. "Isolation and characterization of cGMP phosphodiesterase from bovine rod outer segments." *J. Biol. Chem.* 254:11669 (1979) and Gillespie and Beavo "Inhibition and stimulation of photoreceptor phosphodiesterase by dipyridamole and M&B 22,948" *Molecular Pharm.* 36:773 (1989). A brief summary of the conditions for each enzyme assay is provided in Example 9.

Figure 22A:
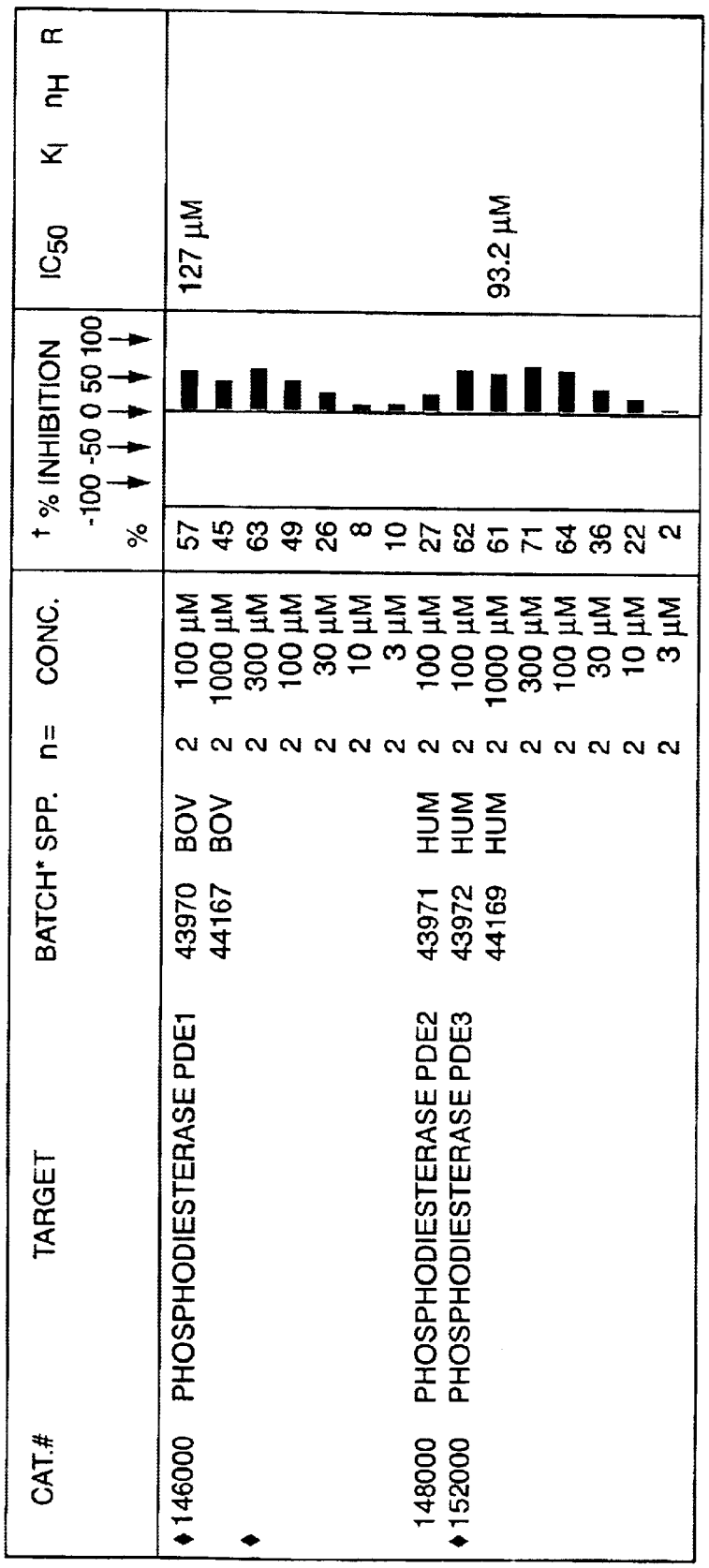
Figure 23:
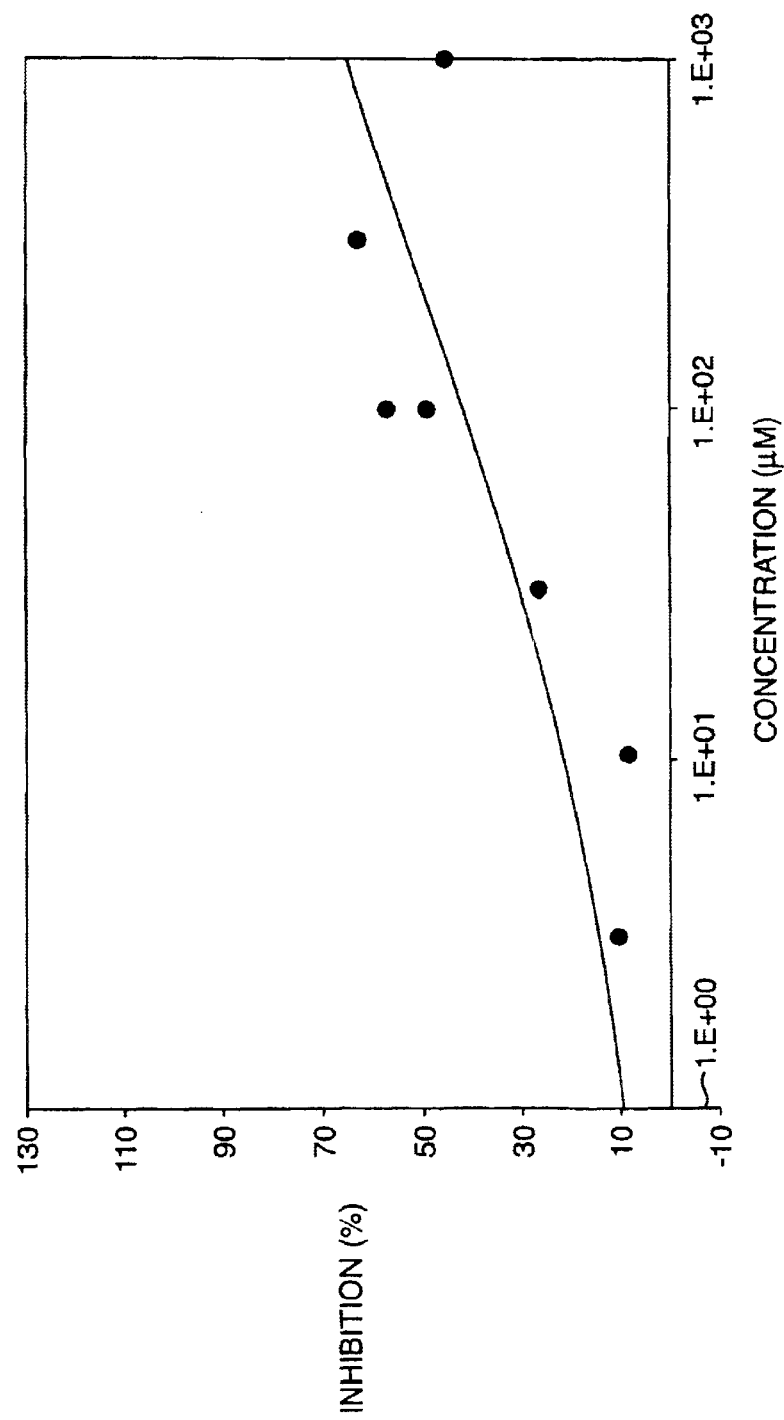
FIG. 23 shows the PDE1 inhibition curves for dichloroflosequinan (circles).
Figure 24:
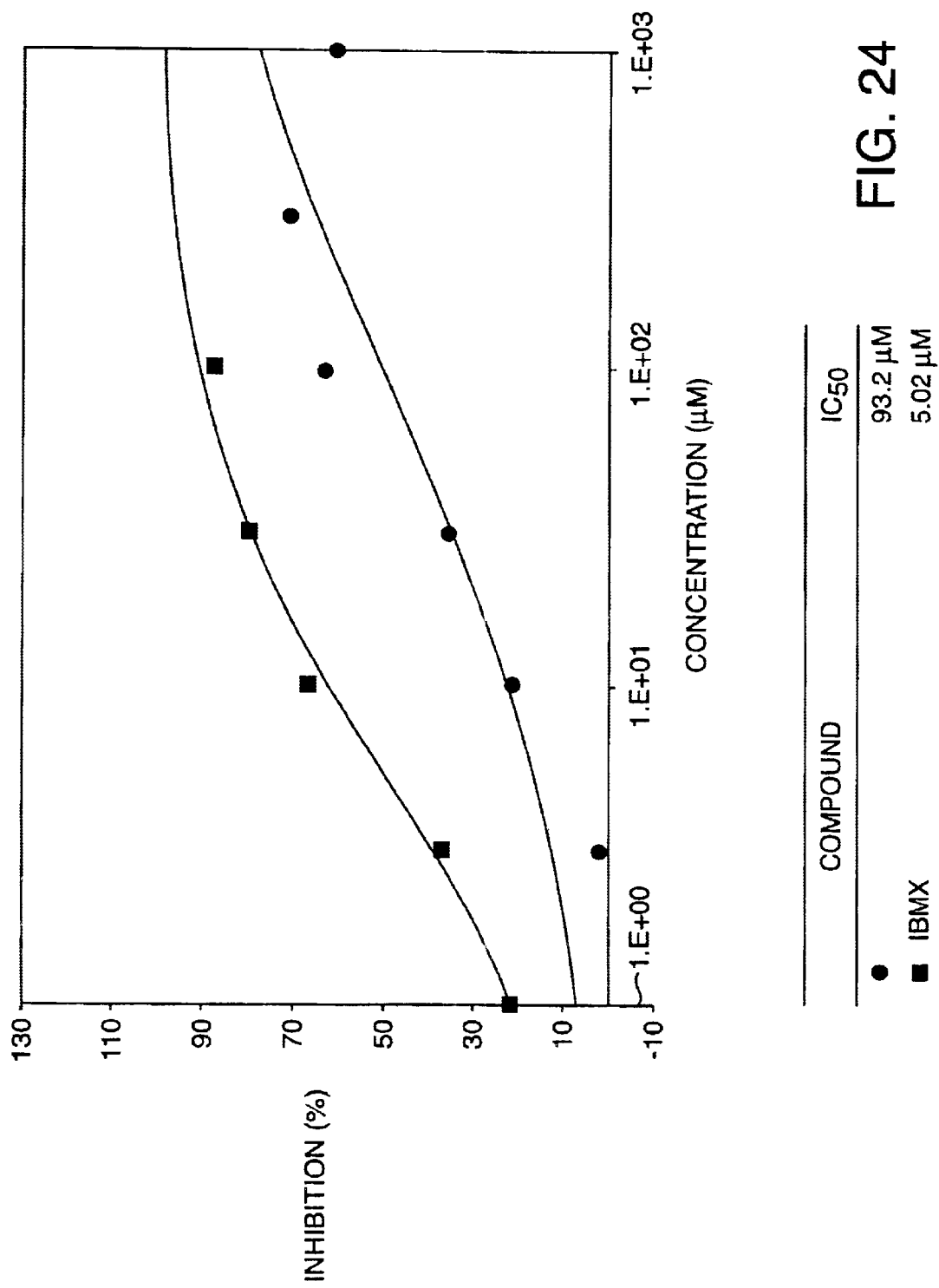
FIG. 24 shows the PDE3 inhibition curves for dichloroflosequinan (circles) and the reference compound, IBMX (squares).
Figure 25:
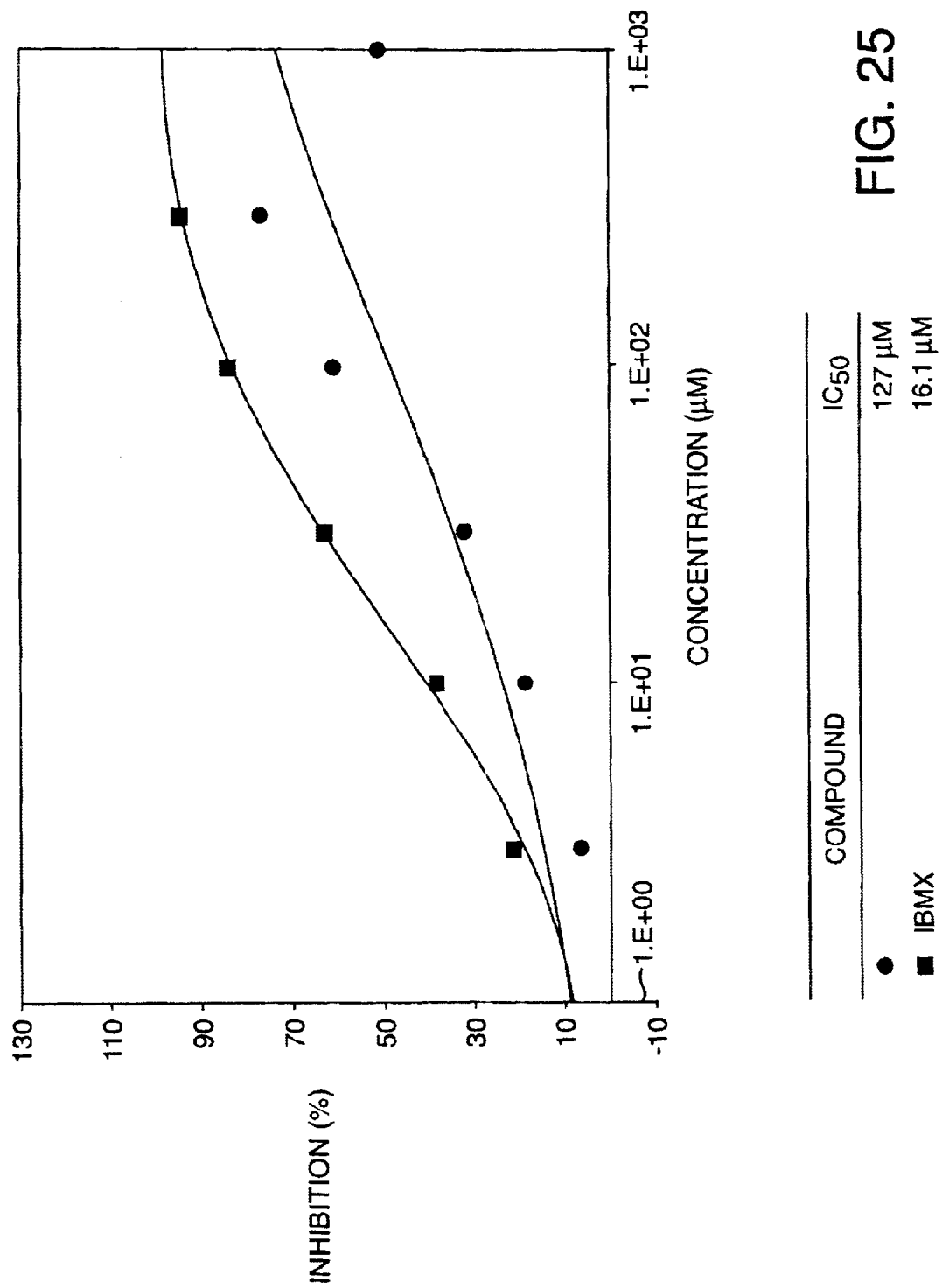
FIG. 25 shows the PDE5 inhibition curves for dichloroflosequinan (circles) and the reference compound, IBMX (squares).

For reference, FIG. 22A and FIG. 22B show the results of assays carried out as described above with dichloroflosequinan. Each PDE was assayed at 25° C. with varying concentrations of dichloroflosequinan (in 1% DMSO as the vehicle). Significant inhibition (e.g. greater than 50% inhibition) of PDE1, PDE3, and PDE5 was observed. FIG. 23 shows the inhibition curves for PDE1 for dichloroflosequinan (circles). FIG. 24 shows the inhibition curves for PDE3 for dichloroflosequinan (circles) and the reference compound, IBMX (squares). FIG. 25 shows the inhibition curves for PDE5 for dichloroflosequinan (circles) and the reference compound, IBMX (squares).

C. Synthesis of Carboxyflosequinan

Example 13

Synthesis of 3-Carboxymethylsulfinyl-7-fluoro-1-methyl-4-quinolone (5).

Figure 27:
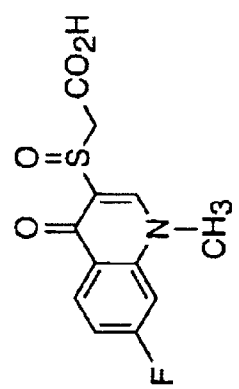
FIG. 27 shows the chemical structure of 3-carboxymethylsulfinyl-7-fluoro-1-methyl-4-quinolone.
Figure 28:
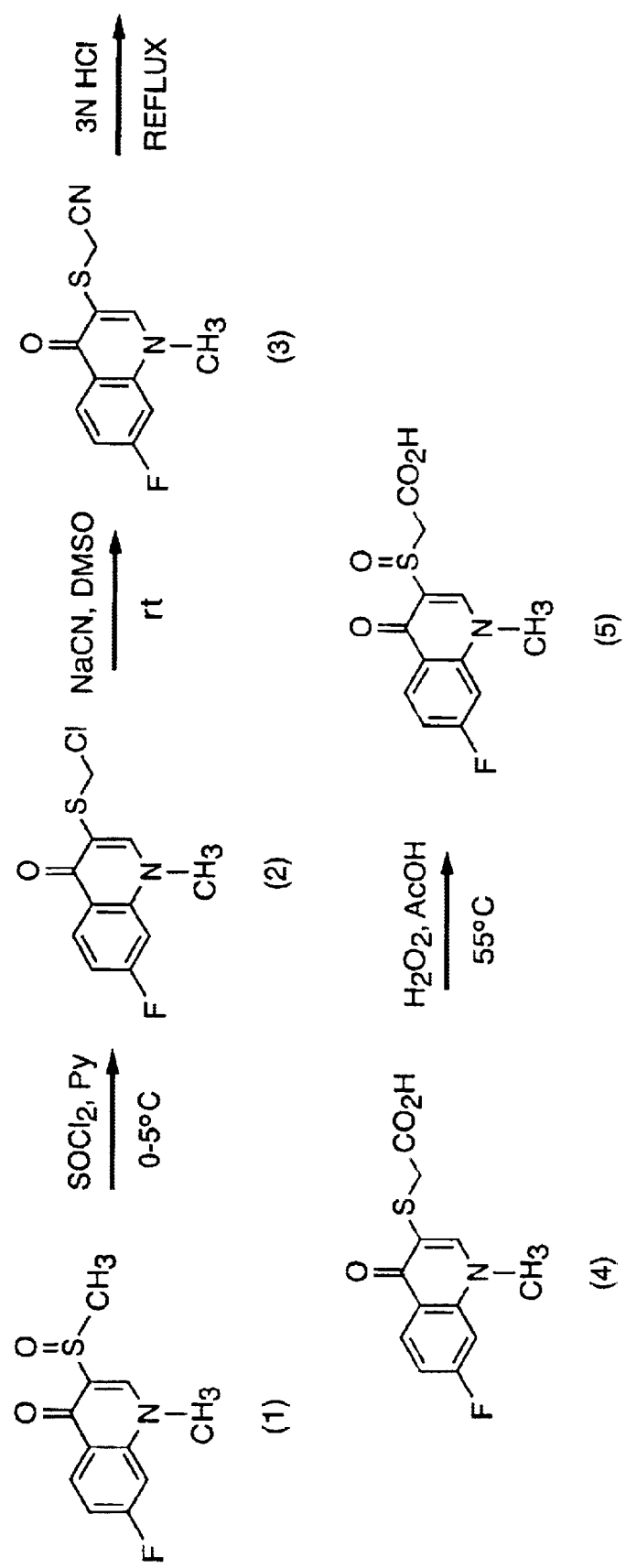
FIG. 28 displays a scheme for the synthesis of 3-carboxymethylsulfinyl-7-fluoro-1-methyl-4-quinolone.

For reference, see FIGS. 27 and 28. To an efficiently stirred and gently cooled with dry-ice acetone mixture of 12 ml of thionyl chloride ($SOCl_2$) and 3 ml of pyridine (Py) at −3° C. was added flosequinan (3.59 g, 15 mmol) (1) in a few portions over a period of approximately 1 min. During that time cooling was applied to keep the temperature in the range 0–6° C. The mixture was stirred at 0° C. for 5 min, cooled to −5° C. and poured as a thin stream into 350 ml of ice-water with efficient stirring. After 10 min stirring at 0° C. a solid was filtered off, washed with water, and dried over phosphorus pentoxide under high vacuum. Yield 2.82 g (74%) of a crude product that was ~95% pure by $^1H$ NMR. The crude product (3-Chloromethylthio-7-fluoro-1-methyl-4-quinolone) (2) was used in the next step without further purification.

To efficiently stirred suspension of sodium cyanide (490 mg, 10 mmol) in dry DMSO (15 ml) at room temperature under a $N_2$ atmosphere was added crude 3-chloromethylthio-7-fluoro-1-methyl-4-quinolone (1.031 g, 4 mmol) (2) in a few portions. The mixture was stirred for 1 h and poured into diluted $H_2SO_4$ with ice. The solid was filtered off. The filtrate was extracted twice with ethyl acetate, the combined extracts were dried over anhydrous $Na_2SO_4$ and concentrated. The residue was combined with the solid and was chromatographed on silica gel with hexane-ethyl acetate (gradient 2:1,1:1,1:2) to give 644 mg (65%) of the product as a brownish solid. The product (3-Cyanomethylthio-7-fluoro-1-methyl-4-quinolone; 575 mg) (3) was further purified by recrystallization from methanol to give 382 mg of brownish crystals.

A mixture of 3-cyanomethylthio-7-fluoro-1-methyl-4-quinolone (265 mg, 1.067 mmol) (3) and 3N hydrochloric acid (8 ml) was refluxed under a $N_2$ atmosphere for 2.5 h. The hot mixture was diluted with water (1 ml) and allowed to cool to room temperature. A solid that precipitated was filtered off and dried under high vacuum. The yield of 3-Carboxymethylthio-7-fluoro-1-methyl-4-quinolone (4) was 270 mg (94.7%).

50% hydrogen peroxide (57 ml, 33.6 mg, 0.988 mmol) was added to a solution of 3-carboxymethylthio-7-fluoro-1-methyl-4-quinolone (4) in acetic acid (3.6 ml) at 60° C. and the mixture was stirred at 55° C. for 4 h. The hot mixture was diluted with water (12 ml) and cooled to 0° C. A white solid that precipitated was filtered off and dried under high vacuum. The yield of 3-Carboxymethylsulfinyl-7-fluoro-1-methyl-4-quinolone was 185 mg (72.7%) (5).

Example 14

In this example flosequinan is prepared according to the protocol of Example 8.

Example 15

In this example, carboxyflosequinan was subjected to biochemical enzyme assays and radioligand binding assays to determine its percent inhibition of a variety of enzyme activities. Tamaoki and Nakano "Potent and specific inhibitors of protein kinase C of microbial origin" *Biotechnology* 8:732 (1990); Wilkinson et al. "Isoenzyme specificity of bisindolymaleimides, selective inhibitors of protein kinase C" *Biochem. J.* 294:335 (1993); Tamaki et al. "Staurosporine, a potent inhibitor of phospholipid/Ca++ dependent protein kinase" *Biochem. Biophys. Res. Comm*, 135:397 (1986). A brief summary of the conditions for each assay is provided below:

Protein Serine/Threonine Kinase PKCα: Human recombinant enzyme from Sf9 insect cells was used in the assay. The substrate was 200 μg/ml histone. The reaction was incubated 10 mins at 25° C. in 20 mM Hepes, 10 mM $MgCl_2$, 0.1 mM $CaCl_2$. [$^{32}P$]histone was quantitated.

Protein Serine/Threonine Kinase PKC, non-selective: The enzyme was obtained from rat brain and the substrate was 370 μg/ml histone. The reaction was pre-incubated 5 min at 25° C., followed by a 15 min incubation at 25° C. in a buffer of 20 mM Tris-HCl, 10 mM $MgCl_2.H_O$ and 0.1 mM $CaCl_2.2H_O$, pH 7.4. [$^{32}$P]histone was quantitated.

FIG. 29 projects data for carboxyflosequinan in the assays described above. In these protein kinase assays, carboxyflosequinan was used in varying concentrations (in 1% DMSO as the vehicle). For the protein serine/threonine kinase (PKC, non-selective), carboxyflosequinan was tested at a concentrations of 100 μM, 300 μM, and 1000 μM. Significant (e.g., greater than 50%) inhibition was observed at all three concentrations of carboxyflosequinan. (See, FIG. 29).

All publications and patents mentioned in the above specification are herein incorporated by reference. Various modifications and variations of the described invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

D. Synthesis of Fluoroflosequinan

Figure 30B:
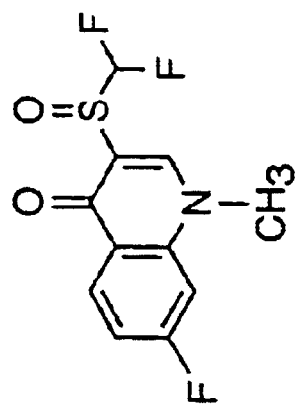
FIG. 30B depicts the chemical structure of 3-difluoromethylsulfinyl-7-fluoro-1-methyl-4-quinolone (difluoroflosequinan).
Figure 30A:
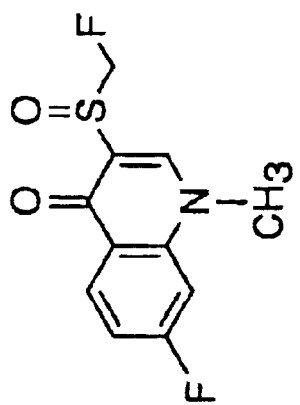
FIG. 30A depicts the chemical structure of 7-fluoro-3-fluoromethylsulfinyl-1-methyl-4-quinolone (monofluoroflosequinan).

In Examples 16–19, unless otherwise stated, the source for the chemical reagents was Aldrich, Milwaukee, Wis., USA (unless a reagent was synthesized de novo as described in the examples). In Examples 17–19, flosequinan was synthesized according to the protocol provided in Example 20, unless otherwise stated. For reference, FIG. 30A depicts the chemical structure of 7-fluoro-3-fluoromethylsulfinyl-1-methyl-4-quinolone (monofluoroflosequinan) and FIG. 30B depicts the chemical structure of 3-difluoromethylsulfinyl-7-fluoro-1-methyl-4-quinolone (difluoroflosequinan).

Example 16

Synthesis of racemic monofluoroflosequinan. This overall synthetic scheme is described in more detail according to the following reactions. For the purpose of this example, all bracketed numbers [e.g., "(1)"], after the chemical name of a compound, refer to the corresponding chemical structure as designated by the same bracketed number in FIG. 31. The synthesis of 7-fluoro-3-fluoromethylsulfinyl-1-methyl-4-quinolone (3) (monofluoroflosequinan) was carried out in two stages (see FIG. 31). In the first stage, into a solution of 1.017 g (4.25 mmol) of 7-fluoro-1-methyl-3-methylsulfinyl-4-quinolone (1) in 17 ml of dichloromethane (DCM), 0.758 ml (925 mg, 5.74 mmol) of (diethylamino)sulfur trifluoride (DAST) was added at 20° C. The mixture was stirred at 25° C. for 3 days and then diluted with 40 ml of ether. The precipitated 688 mg (67%) of 7-fluoro-3-fluoromethylthio-1-methyl-4-quinolone (2) was filtered off. An additional 177 mg (17%) of the product (2) was collected after diluting the filtrate with 60 ml of ether. 1H NMR, $CDCl_3$; δ=3.80 s, 3H, N—$CH_3$; 5.69 d, 2H, J=52.8 Hz, $CH_2$; 7.08 dd, 1H, J=10.2 & 2.4 Hz, H at C8, 7.18 ddd, 1H, J=8.8, 7.9 & 2.2 Hz, H at C6; 8.00 s, 1H, H at C2; 8.51 dd, 1H, J=9.0 & 6.3 Hz, H at C5.

The crude product (2) was used in the second stage. To a stirred solution of 673 mg (2.873 mmol) of compound (2) in 80 ml DCM, ~80%, m-chloroperbenzoic acid (MCPBA) (620 mg, 2.873 mmol) was added in a few portions over a period of 1 minute at 0° C. The stirred mixture was allowed to warm to room temperature, was stirred for one hour and then an additional 18 mg of MCPBA was added to complete the transformation. After 30 minutes stirring at room temperature the reaction solution was washed with 15 ml of 5% aqueous sodium carbonate. The aqueous layer was extracted two times with 60 ml of DCM each and the combined DCM solutions were dried over sodium sulfate and concentrated. The residue 660 mg was chromatographed on silica gel with hexane-ethyl acetate (gradient 1:1, 2:3, 1:2) to give 358 mg (50% yield) of racemic 7-fluoro-3-fluoromethylsulfinyl-1-methyl-4-quinolone (3) (monofluoroflosequinan) as a white solid. 1H NMR, $CDCl_3$; δ=3.93 s, 3H, N—$CH_3$; 5.75, 5.73, 5.59, 5.56, 5.46, 5.43, 5.30, 5.27 (8 lines, AB part of ABX), 2H, $CH_2$; 7.18–7.30 m, 2H, H at C8 & C6; 7.98 s, 1H, H at C2; 8.44 dd, 1H, J=9.0 & 6.3 Hz, H at C5.

Example 17

Synthesis of 7-fluoro-3-fluoromethylthio-1-methyl-4-quinolone (Stage One of the synthesis of monofluoroflosequinan) using a catalyst.

This overall synthetic scheme is described in more detail according to the following reactions. For the purpose of this example, all bracketed numbers [e.g., "(1)"], after the chemical name of a compound, refer to the corresponding chemical structure as designated by the same bracketed number in FIG. 32. This example presents the synthesis and results of a representative experiment.

Into a solution of 3.00 g (12.54 mmol) of 7-fluoro-1-methyl-3-methylsulfinyl-4-quinolone (1) and 28.6 mg (0.125 mmol) of antimony chloride ($SbCl_3$) in 40 ml of dichloromethane (DCM), 2.24 ml (2.73 g, 16.92 mmol) of(diethylamino)sulfur trifluoride (DAST) was added at 20° C. The mixture was stirred at 25° C. for 7 hours and then diluted with 70 ml of ether. The precipitated 0.783 g (26%) of 7-fluoro-3-fluoromethylthio-1-methyl-4-quinolone (2) was filtered off. An additional 1.679 g (55%) of the product (2) was collected after diluting the filtrate with 130 ml of ether and cooling to 5° C.

Example 18

This example demonstrates the synthesis of difluoroflosequinan (3-difluoromethylsulfinyl-7-fluoro-1-methyl-4-quinolone). The overall synthetic scheme is described in more detail according to the following reactions. For the purpose of this example, all bracketed numbers [e.g., "(1)"] after the chemical name of a compound refer to the corresponding chemical structure as designated by the same bracketed number in FIG. 33.

Step One: Fluorination of 7-fluoro-3-fluoromethylthio-1-methyl-4-quinolone (2) to synthesize 3-difluoromethylthio-7-fluoro-1-methyl-4-quinolone (4).

To a stirred solution (a part remained undissolved) of crude 7-fluoro-3-fluoromethylthio-1-methyl-4-quinolone (2) (4.15 g, 17.2 mmol) in dry acetonitrile (138 ml) under a nitrogen atmosphere SELECTFLUOR [Product No. 25140; 1-chloromethyl-4-fluoro-1,4-diazoniabicyclo[2.2.2]octane bis(tetrafluoroborate)] (7.617 g, 21.5 mmol) was added in a few portions over a period of approximately 2 min. During the addition a slight cooling was applied to keep the temperature below 23° C. After 15 min of stirring at 23° C., triethylamine (3.0 ml, 2.18 g, 21.5 mmol)-was added with cooling over a period of approximately 2 min. and stirring was continued at 23° C. for 10 min. The reaction mixture was poured into ice-water mixture (750 ml), and extracted with four 300 ml portions of DCM. The combined extracts were dried over a mixture of anhydrous sodium sulfate and sodium carbonate, and concentrated to give 3.43 g of a crude product, which contained less than 30% of 3-difluoromethylthio-7-fluoro-1-methyl-4-quinolone (4). The presence of the compound (4) was confirmed by a characteristic triplet observed in $^1$H NMR spectrum ($\delta$=7.10 ppm, J=58.9 Hz). The crude product was used in the second step without purification.

Step Two: Oxidation of 3-difluoromethylthio-7-fluoro-1-methyl-4-quinolone (4) to synthesize 3-difluoromethylsulfinyl-7-fluoro-1-methyl-4-quinolone (5).

To a stirred solution (a part remained undissolved) of crude 3-difluoromethylthio-7-fluoro-1-methyl-4-quinolone (4) (3.43 g, 13.23 mmol) in DCM (200 ml) at 0° C. was added ~80% MCPBA (2.50 g, 11.59 mmol) in a few portions over a period of approximately 1 min. The stirred mixture was allowed to warm to room temperature and was stirred for 30 min. An additional amount of MCPBA (640 mg) was added in 5 portions in approximately 1 h intervals, and the progress of the oxidation was monitored by $^1$H NMR 30 min after each addition. The mixture was washed with 5% aqueous $Na_2CO_3$ (70 ml), the aqueous layer was extracted with DCM (2×200 ml), the combined extracts were dried over anhydrous sodium sulfate and concentrated. The residue was chromatographed on silica gel with DCM and then with hexane-ethyl acetate (gradient 2:1,1:1,1:2) to give 980 mg (20.7%; two steps) of the product. The product was further purified by recrystallization from absolute ethanol to give 620 mg (13.1%) of 3-difluoromethylsulfinyl-7-fluoro-1-methyl-4-quinolone (5) as off-white crystals. $^1$H NMR, $CDCl_3$; $\delta$=3.94 s, 3H, N—$CH_3$; 7.050, 6.870, 6.866, 6.686 (4 lines, X part of ABX), 1H, $CHF_2$; 7.21 dd, 1H, J=10.2 & 2.4 Hz, H at C8, 7.27 ddd, 1H, J=8.9, 7.9 & 2.2 Hz, H at C6; 7.99 s, 1H, H at C2; 8.44 dd, 1H, J=9.0 & 6.3 Hz, H at C5.

Example 19

In this example racemic flosequinan is prepared according to the method of Example 8.

Example 20

In this example, monofluoroflosequinan was subjected to biochemical enzyme assays and radioligand binding assays to determine its percent inhibition of a variety of enzyme activities and its percent inhibition of specific binding. The methods used have been adapted from those described in the scientific literature, see Hidaka and Asano "Human blood platelet 3':5' cyclic nucleotide phosphodiesterase. Isolation of low-Km and high Km phosphodiesterase." *Biochem. Biophys. Acta* 429:485 (1976); Nicholoson et al. "Differential modulation of tissue function and therapeutic potential of selective inhibitors of cyclic nucleotide phosphodiesterase isoenzymes" *Trends Pharmacol. Sci.* 12:19 (1991); Cortijo et al. "Investigation into the role of phosphodiesterase IV in bronchorelaxation, including studies with hyman bronchus." *Br. J. Pharmacol.* 108:562 (1993); Baehr et al. "Isolation and characterization of cGMP phosphodiesterase from bovine rod outer segments." *J. Biol. Chem.* 254:11669 (1979), Gillespie and Beavo "Inhibition and stimulation of photoreceptor phosphodiesterase by dipyridamole and M&B 22,948" *Molecular Pharm.* 36:773 (1989); Tamaoki and Nakano "Potent and specific inhibitors of protein kinase C of microbial origin" *Biotechnology* 8:732 (1990); Wilkinson et al. "Isoenzyme specificity of bisindolymaleimides, selective inhibitors of protein kinase C" *Biochem. J.* 294:335 (1993); Tamaki et al. "Staurosporine, a potent inhibitor of phospholipid/Ca++ dependent protein kinase" *Biochem. Biophys. Res. Comm*, 135:397 (1986); Schoemaker and Langer "[3H]Diltiazem binding to calcium channel antagonist recognition sites in rate cerebral cortex" *Eur. J. Pharmacol.* 111:273 (1985); Ehlert et al. "The binding of [3H]nitrendipine to receptors for calcium channel antagonists in the heart, cerebral cortex and ileum of rats." *Life Sci*. 30:2191 (1982); Gould et al. "[3H]nitrendipine-labeled calcium channels discriminate inorganic calcium agonists and antagonists" *Proc. Natl. Acad. Sci. USA* 79:3656 (1982); Reynolds et al. "(-)-[3H] Desmethoxyverapamil labels multiple calcium channel modulator receptors in brain and skeletal muscle membranes: Differentiation by temperature and dihydropyridines" *J. Pharmacol. Exp. Ther.* 237:731 (1986) and Worley et al. "Characterization of inositol triphosphate receptor binding in brain. Regulation by pH and calcium" *J. Biol. Chem.* 262:12132 (1987). A brief summary of the conditions for each PDE assay is provided in Example 9.

Protein Serine/Threonine Kinase PKCα: Human recombinant enzyme from Sf9 insect cells was used in the assay. The substrate was 200 µg/ml histone. The reaction was incubated 10 mins at 25° C. in 20 mM Hepes, 10 mM $MgCl_2$, 0.1 mM $CaCl_2$. [$^{32}$P]histone was quantitated.

Protein Serine/Threonine Kinase PKC, non-selective: The enzyme was obtained from rat brain and the substrate was 370 µg/ml histone. The reaction was pre-incubated 5 min at 25° C., followed by a 15 min incubation at 25° C. in a buffer of 20 mM Tris-HCl, 10 mM $MgCl_2.H_O$ and 0.1 mM $CaCl_2.2H_O$, pH 7.4. [$^{32}$P]histone was quantitated.

The radioligand binding assays are briefly summarized below:

Calcium Channel Type L, Benzothiazepine: The source was Wistar rat brain and the ligand was 2 nM $^3$H Diltiazem. The incubation was for 3 hr at 4° C. in 50 mM Tris-HCl, 0.1% BSA, pH 7.4 (buffer at 25° C.). The non-specific ligand was 10 µM Diltiazem. The following are historical values: $K_d$: 0.016 M, $B_{max}$: 0.21 pmol/mg protein, specific binding: 73%. Radioligand binding was quantitated.

Calcium Channel Type L, dihydropyridine: The source was Wistar rat cerebral cortex and the ligand was 0.1 nM $^3$H Nitrendipine. The incubation was for 90 min at 25° C. in 50 mM Tris-HCl, pH 7.7. The nonspecific ligand was 1 µM Nifedipine. The following are historical values: $K_d$: 0.18 nM, $B_{max}$: 0.23 pmol/mg protein, specific binding: 91%. Radioligand binding was quantitated.

Calcium Channel Type L, phenylalkylamine: The source was Wistar rat brain and the ligand was 0.4 nM $^3$H (–)-D-888. The incubation was 60 min at 25° C. in 50 mM Hepes, pH 7.4. The nonspecific ligand was 10 µM (–)-D-600. The following are historical values: $K_d$: 0.014 µM, $B_{max}$: 1.6 pmol/mg protein, specific binding: 80%. Radioligand binding was quantitated.

Inositol Triphosphate, $IP_3$: The source was Wistar rat cerebellum and the ligand was 2.5 nM $^3$H 1,4,5-$IP_3$. The incubation was 10 min at 25° C. in 50 mM Tris-HCl, 1 mM EDTA, 0.1% BSA, pH 8.3. The nonspecific ligand was 1 µM 1,4,5-$IP_3$. The following are historical values: $K_d$: 0.066 µM, $B_{max}$: 3.5 pmol/mg protein, specific binding 85%. Radioligand binding was quantitated.

FIG. 34A and FIG. 34B depict the results for the assays described above. For the PDE inhibition assays, monofluoroflosequinan was used at a concentration of 100 µM (in 1% DMSO as the vehicle). For the protein kinase assays, monofluoroflosequinan was used at a concentration of 1000 µM (in 1% DMSO as the vehicle). For the protein serine/ threonine kinase (PKC, non-selective), monofluoroflosequinan was also tested at 300 µM and 100 µM. For the radioligand binding assays, monofluoroflosequinan was used at a concentration of 1000 µM (in 0.4% DMSO as the vehicle). Significant inhibition of protein serine/threonine kinase, PKC, non-selective was observed at 1000 µM, 300 µM and 100 µM monofluoroflosequinan.

FIG. 35 shows the synthesis of a sulfone derivative of difluroflosequinan.

Figure 36:
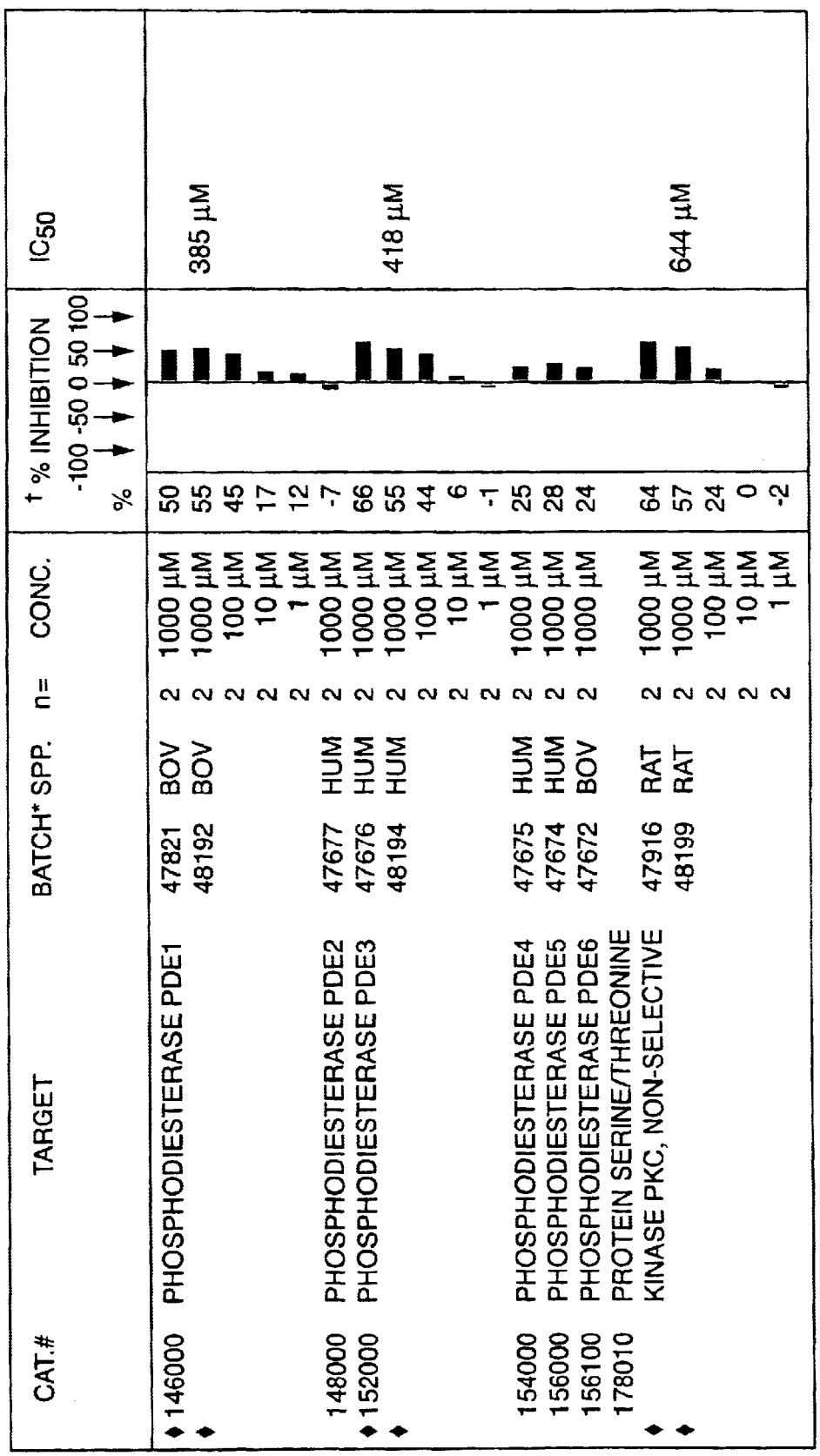
FIG. 36 depicts the results of enzyme inhibition and radioligand binding assays with the sulfone derivative of difluoroflosequinan (e.g., 3-difluoromethylsulfonyl-7-fluoro-1-methyl-4-quinolone).

FIG. 36 projects data for the sulfone derivative of difluoroflosequinan (e.g., 3-difluoromethylsulfonyl-7-fluoro-1-methyl-4-quinolone) in the assays described above. For the PDE inhibition assays, 3-difluoromethylsulfonyl-7-fluoro-1-methyl-4-quinolone was used in varying concentrations (in 1% DMSO as the vehicle). For the protein kinase assays, monofluoroflosequinan was used at a concentration of 1000 µM (in 1% DMSO as the vehicle). For the protein serine/threonine kinase (PKC, non-selective), 3-difluoromethylsulfonyl-7-fluoro-1-methyl-4-quinolone was tested at a concentration of 1000 µM. Significant (e.g., greater than 50%) inhibition of PDE1, PDE3, and PDE4 was observed at a 3-difluoromethylsulfonyl-7-fluoro-1-methyl-4-quinolone of 1000 µM.

Example 21

Synthesis of the sulfone derivative of difluoroflosequinan. This overall synthetic scheme is described in more detail according to the following reactions. For the purpose of this example, all bracketed numbers [e.g., "(1)"], after the chemical name of a compound, refer to the corresponding chemical structure as designated by the same bracketed number in FIG. 36.

To a solution of 3-difluoromethylsulfinyl-7-fluoro-1-methyl-4-quinolone (5) (79 mg, 0.287 mmol) in DCM (8 mL) was added ~80% MCPBA (55.7 mg, 0.258 mmol). The mixture was stirred at a room temperature overnight. An additional amount of MCPBA (15 mg) was added and stirring was continued for 3 days. The mixture was diluted with DCM (10 mL), washed with 5% aqueous $Na_2CO_3$ (3×5 mL), the aqueous layers were extracted with DCM (2×10 mL), the combined organic extracts were dried over anhydrous sodium sulfate and concentrated. The residue, e.g., the crude product, was recrystallized from ethyl acetate to give 27 mg (32%) of white crystals [3-difluoromethylsulfonyl-7-fluoro-1-methyl-4-quinolone (6)]. The filtrate was chromatographed on silica gel with ethyl acetate-hexane (gradient 1:2, 1:1) to give second crop of the product [3-difluoromethylsulfonyl-7-fluoro-1-methyl-4-quinolone (6)] (32 mg, 38%) for a total yield 70%. This 3-difluoromethylsulfonyl-7-fluoro-1-methyl-4-quinolone gave the following NMR profile:

$^1$H NMR, $CDCl_3$; δ=3.94 s, 3H, N—$CH_3$; 6.85 t, 1H, J=54.3 Hz, $CHF_2$; 7.21 dd, 1H, J=9.7 & 2.2 Hz, H at C8, 7.35–7.26 m, 1H, H at C6; 8.41 s, 1H, H at C2; 8.49 dd, 1H, J=8.8 & 6.1 Hz, H at C5.

E. Inducment of Penile Erection with the Administration of Monochloroflosequinan Example 22

In this example, various halogenated derivatives of flosequinan were evaluated for their ability to induce penile erections. A single intracavernosal dose (of a given halogenated derivative of flosequinan) was administered to male Cynomolgus monkeys (*Macaca fascicularis*). The Cynomolgus monkey was selected because it is an appropriate established non-rodent species to be used as an erectile dysfunction model.

The animals were dosed as detailed below (Table 4) and receive a tasty reward (piece of fruit/pellet/bread/peanut/primate muesli) immediately after dosing for conditioning purposes.

Before the application of the test substances the possible erectile effect of dimethylsulfoxide 25% (DMSO) at a dose volume of 0.15 ml was assessed. (Concentrations of test compounds of less than 10 mg/ml were administered in 25% DMSO. Concentrations of 10 mg/ml or greater were administered in 100% DMSO). An initial dose level of 0.625 mg/kg of the test substance and the derivatives were used. If an erectile effect of the initial dose level was observed 1.25 mg/kg and finally 2.5 mg/kg of each test substance was used. Between each dose level and change of test substance there was a wash out phase of three days [except on Days 1 to 4 (Monochloroflosequinan Racemate) and days 40 to 43 (Monofluoroflosequinan) of the study where there was a wash out phase of only two days between treatments]. Dose volume: A dose volume of 0.15 ml per animal was used.

The test substances were prepared according to the following scheme. For each test substance 10 mg was diluted in 1 ml of DMSO. After the test substance was completely dissolved the solution was diluted stepwise 1:2 with double distilled water to the required dose level. The test substance was formulated on the day of the dosing and stored at room temperature. No stability test was required when the test substances were formulated on the day of dosing. Remaining test substances were stored at approximately −80° C.

Sufficient purpose-bred naive Cynomolgus monkeys (*Macaca fascicularis*) were obtained from a recognized supplier in order to provide 4 healthy male animals. At the start of study the animals were in the weight range of 4 to 7 kg and approximately 4 to 6 years old. The animals were housed in a climate controlled room to provide a minimum of 10 air changes per hour. Routinely the temperature and relative humidity ranges were between 19–25° C. and 30–70% respectively. Artificial lighting was controlled automatically to give a cycle of 12 hours light and 12 hours dark. The animals were housed singly in stainless steel cages (dimensions: 600 mm×600 mm×800 mm; E. Becker & Co. GmbH, 44579 Castrop-Rauxel, Germany). Each animal was offered twice daily between 50 to 70 g of a commercial pellet diet for primates (Ssniff P10, Ssniff Spezialdiäten GmbH, Ferdinand-Gabriel-Weg 16, 59494 Soest, Germany). Every three months diet was analyzed for specific contaminants. Tap water was provided ad libtum via an automatic watering system or bottles, except during urine collection. The water was periodically analyzed for specific contaminants found to be present in the diet or water at levels that might interfere with achieving the objective of the study.

In order to monitor the welfare of an individual or a group of animals, additional observations to those already detailed may be instigated at the discretion of the Study Director. In certain instances this may include treatment as advised by a veterinary surgeon.

On arrival, all animals were given a clinical inspection for ill health. Additionally, they were tested for tuberculosis three times, which will be repeated in approximately 6 month intervals. Antihelminthic examinations were performed on arrival and repeated after about 2 weeks. Any prophylactic treatments administered were documented. Animals were quarantined/acclimatized for a period of at least 6 weeks before commencement of the experiment. In addition, each animal was examined during quarantine/acclimatization by laraoscopy and only animals without critical positive findings were accepted for the study. A veterinary inspection was performed before the start of dosing to ensure their suitability for study.

The animals were individually identified by alpha-numeric tattoo. Cages were appropriately identified with study information including study number and animal number/s and sex.

Clinical Observations: In addition to the initial pharmacological effect (penile erection) monitoring, all animals were observed twice daily for signs of ill health or overt toxicity. An individual record was maintained of the clinical condition of each animal. Post-dosing observations were performed at the discretion of the Study Director. All animals were examined at the beginning and the end of the working hours. Any animal which showed marked signs of ill health was isolated. Body weights were recorded once before dosing. Food consumption was not recorded. For proof of erection capability the animals were checked once pre-dose with electrostimulation using a rectal probe under sedation with ketavet.

Animals were observed for penile erections continuously for 2 hours after every drug administration. Thereafter animals were observed for penile erections at 0.5 hour intervals until 4 hours after dosing. The onset post drug administration and duration of erection were recorded.

This study was conducted with reference to the OECD principles of Good Laboratory Practice (revised 1997, issued January 1998) ENV/MC/CHEM (98) 17, the Good Laboratory Practice Regulations as outlined in the German Chemical Law, annex 1 and 2 to §19a Chemikaliengesetz, May 2001.

Table 4 (below) shows the erection monitoring results, in Cynomolgus monkeys, after the intracavernosal administration of selected halogenated flosequinan derivatives described by the present invention. In addition, DMSO was administered (at 25% and 100%) as a control.

Table 5 (below) provides an "Erection Score" and "Erection Index" for the same selected halogenated flosequinan derivatives presented in Table 5. These indices were scored according to the following criteria:

Duration (D)

0=no response

1=erection but transient—less than 1 minute

2=erection lasting at least 1 minute but less than 5 minutes

3=erection lasting at least 5 minutes but less than 7 minutes

4=erection lasting longer than 7 minutes,

Onset (O)

0=no response

1=erection onset longer than 10 minutes

2=erection onset between 5 and 9 minutes

3=erection onset between 2 and 4 minutes

4=erection onset 1 minute or less (immediate)

Erection Score=2D+O

Erection Index=Erection Score/n, where n=number of animals

These data (as set out in Tables 4 & 5) demonstrate that the S(+) enantiomer of monochloroflosequinan and dichloroflosequinan were especially effective in inducing penile erections in Cynomolgus monkeys.

All publications and patents mentioned in the above specification are herein incorporated by reference. Various modifications and variations of the described invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

TABLE 4

Erection Monitoring Results

25% DMSO Day 1 of Study

| Dose (mg/ml) | Monkey ID | Onset of Erection* (min) | Duration Erection (min) |
|---|---|---|---|
| Period 1 | 11539M | — | — |
| Period 1 | 11543M | — | — |
| Period 1 | 11584M | — | — |
| Period 1 | 11590M | — | — |

MONOCHLOROFLOSEQUINAN RACEMIC Day 4 and 8 of Study

| Dose (mg/ml) | Monkey ID | Onset of Erection (min) | Duration Erection (min) |
|---|---|---|---|
| Period 1 0.625 mg/ml | 11539M | — | — |
| Period 1 0.625 mg/ml | 11543M | 70$^{a*}$ ejaculation- | <1 min- |
| Period 1 0.625 mg/ml | 11584M | — | — |
| Period 1 0.625 mg/ml | 11590M | — | — |

| Dose (mg/ml) | Monkey ID | Onset of Erection (min) | Duration Erection (min) |
|---|---|---|---|
| Period 2 2.5 mg/ml | 11539M | — | — |
| Period 2 2.5 mg/ml | 11543M | — | — |
| Period 2 2.5 mg/ml | 11584M | — | — |
| Period 2 2.5 mg/ml | 11590M | — | — |

MONOCHLOROFLOSEQUINAN S(+) Day 12 of Study

| Dose (mg/ml) | Monkey ID | Onset of Erection* (min) | Duration Erection (min) |
|---|---|---|---|
| Period 1 2.5 mg/ml | 11539M | 107* | <1 min |
| Period 1 2.5 mg/ml | 11543M | 34* | <1 min |
| Period 1 2.5 mg/ml | 11543M | 38* | <1 min |
| Period 1 2.5 mg/ml | 11543M | 39$^{a*}$ ejaculation | <1 min |
| Period 1 2.5 mg/ml | 11584M | — | — |
| Period 1 2.5 mg/ml | 11590M | immediate <1 min | 5 min |
| Period 1 2.5 mg/ml | 11590M | 7 min | <1 min |

100% DMSO Day 19 of Study

| | | | |
|---|---|---|---|
| Period 1 | 11539M | — | — |
| Period 1 | 11543M | — | — |
| Period 1 | 11584M | — | — |
| Period 1 | 11590M | 1* | 1 min |

MONOCHLOROFLOSEQUINAN S(+) Day 26 of Study

| Dose (mg/ml) | Monkey ID | Onset of Erection (min) | Duration Erection (min) |
|---|---|---|---|
| Period 2 10 mg/ml | 11539M | $^a$ejaculation | — |
| Period 2 10 mg/ml | 11543M | — | — |
| Period 2 10 mg/ml | 11584M | 4* 9* ejaculation | <1 min |
| Period 2 10 mg/ml | 11590M | immediate <1 min | 8 min |

DICHLOROFLOSEQUINAN Day 32 of Study

| Dose (mg/ml) | Monkey ID | Onset of Erection (min) | Duration Erection (min) |
|---|---|---|---|
| Period 1 10 mg/ml | 11539M | — | — |
| Period 1 10 mg/ml | 11543M | immediate <1 min 7* | 1 min 1 min |

TABLE 4-continued

Erection Monitoring Results

| | | | |
|---|---|---|---|
| Period 1 10 mg/ml | 11584M | immediate <1 min | 1 min |
| Period 1 10 mg/ml | 11590M | immediate <1 min | 7 min |

MONOCHLOROFLOSEQUINAN R(−) Day 40 of Study

| Dose (mg/ml) | Monkey ID | Onset of Erection (min) | Duration Erection (min) |
|---|---|---|---|
| Period 1 10 mg/ml | 11539M | — | — |
| Period 1 10 mg/ml | 11543M | — | — |
| Period 1 10 mg/ml | 11584M | — | — |
| Period 1 10 mg/ml | 11590M | immediate <1 min | 7 min |

MONOFLUOROFLOSEQUINAN Day 43 of Study

| Dose (mg/ml) | Monkey ID | Onset of Erection (min) | Duration Erection (min) |
|---|---|---|---|
| Period 1 10 mg/ml | 11539M | — | — |
| Period 1 10 mg/ml | 11543M | — | — |
| Period 1 10 mg/ml | 11584M | — | — |
| Period 1 10 mg/ml | 11590M | 1* | 1 min |
| | | 12* | 2 min |

DIFLUOROFLOSEQUINAN Day 48 of Study

| Dose (mg/ml) | Monkey ID | Onset of Erection (min) | Duration Erection (min) |
|---|---|---|---|
| Period 1 10 mg/ml | 11539M | — | — |
| Period 1 10 mg/ml | 11543M | — | — |
| Period 1 10 mg/ml | 11584M | — | — |
| Period 1 10 mg/ml | 11590M | immediate <1 min | 6 min |

CARBOXYFLOSEQUINAN Day 53 of Study

| Dose (mg/ml) | Monkey ID | Onset of Erection (min) | Duration Erection (min) |
|---|---|---|---|
| Period 1 10 mg/ml | 11539M | — | — |
| Period 1 10 mg/ml | 11543M | — | — |
| Period 1 10 mg/ml | 11584M | — | — |
| Period 1 10 mg/ml | 11590M | immediate <1 min | 2 min |

MONOCHLOROFLOSEQUINAN RACEMIC Day 57 of Study

| Dose (mg/ml) | Monkey ID | Onset of Erection* (min) | Duration Erection (min) |
|---|---|---|---|
| Period 1 10 mg/ml | 11539M | — | — |
| Period 1 10 mg/ml | 11543M | — | — |
| Period 1 10 mg/ml | 11584M | — | — |
| Period 1 10 mg/ml | 11590M | — | — |

*Minutes post intracavernosal administration
a Got erection and started to masturbate and ejaculated immediately

TABLE 5

Listing of Erecetion Score and Erection Index

| Monkey D | Onset Score | Duration Score | Erection Score | Erection Index | Onset Score | Duration Score | Erection Score | Erection Index |
|---|---|---|---|---|---|---|---|---|
| | 25% DMSO Day 1 of Study | | | | 100% DM50 Day 19 of Study | | | |
| 11539M | 0 | 0 | 0 | | 0 | 0 | 0 | |
| 11543M | 0 | 0 | 0 | | 0 | 0 | 0 | |
| 11584M | 0 | 0 | 0 | | 0 | 0 | 0 | |
| 11590M | 0 | 0 | 0 | 0 | 4 | 2 | 8 | 2.0 |
| | Monochloroflosequinan Racemic (0.625 mg/ml) Day 4 of Study | | | | Monochloroflosequinan Racemic (2.5 mg/ml) Day 8 of Study | | | |
| 11539M | 0 | 0 | 0 | | 0 | 0 | 0 | |
| 11543M | 0 | 0 | 0 | | 0 | 0 | 0 | |
| 11584M | 0 | 0 | 0 | | 0 | 0 | 0 | |
| 11590M | 0 | 0 | 0 | 0 | 0 | 0 | 0 | 0 |
| | Monochloroflosequinan S(+) (2.5 mg/ml) Day 12 of Study | | | | Monochloroflosequinan S(+) (10 mg/ml) Day 26 of Study | | | |
| 11539M | 1 | 1 | 3 | | 4* | 0 | 4 | |
| 11543M | 1* | 1 | 3 | | 0 | 0 | 0 | |
| 11584M | 1 | 1 | 3 | | 3* | 1 | 5 | |
| 11590M | 4 | 3 | 10 | 4.8 | 4 | 4 | 12 | 5.3 |
| | Dichloroflosequinan (10 mg/ml) Day 32 of Study | | | | Monochloroflosequinan R(−) (10 mg/ml) Day 40 of Study | | | |
| 11539M | 0 | 0 | 0 | | 0 | 0 | 0 | |
| 11543M | 4 | 2 | 8 | | 0 | 0 | 0 | |

TABLE 5-continued

Listing of Erecetion Score and Erection Index

| Monkey D | Onset Score | Duration Score | Erection Score | Erection Index | Onset Score | Duration Score | Erection Score | Erection Index |
|---|---|---|---|---|---|---|---|---|
| 11584M | 4 | 2 | 8 | | 0 | 0 | 0 | |
| 11590M | 4 | 4 | 12 | | 4 | 3 | 10 | |
| | | | | 7.0 | | | | 2.5 |
| | Monofluoroflosequinan (10 mg/ml) Day 43 of Study | | | | Difluoroflosequinan (10 mg/ml) Day 48 of Study | | | |
| 11539M | 0 | 0 | 0 | | 0 | 0 | 0 | |
| 11543M | 0 | 0 | 0 | | 0 | 0 | 0 | |
| 11584M | 0 | 0 | 0 | | 0 | 0 | 0 | |
| 11590M | 4 | 4 | 12 | | 4 | 3 | 10 | |
| | | | | 3.0 | | | | 2.5 |
| | Carboxyflosequinan (10 mg/ml) Day 53 of Study | | | | Monochloroflosequinan Racemic (10 mg/ml) Day 57 of Study | | | |
| 11539M | 0 | 0 | 0 | | 0 | 0 | 0 | |
| 11543M | 0 | 0 | 0 | | 0 | 0 | 0 | |
| 11584M | 0 | 0 | 0 | | 0 | 0 | 0 | |
| 11590M | 4 | 4 | 8 | | 0 | 0 | 0 | |
| | | | | 2 | | | | 0 |

*Ejaculation Occurred

What is claimed is:

1. A method, comprising:
   a) providing:
      i) a patient suffering from at least one symptom of sexual dysfunction and,
      ii) a pharmaceutical composition comprising a substantially purified (+) enantiomer of monochloroflosequinan; and
   b) administering said pharmaceutical composition to said patient such that at least one symptom of sexual dysfunction is reduced.

2. The method of claim 1, wherein said composition is substantially free of the (−) enantiomer of monochloroflosequinan.

3. The method of claim 1, wherein said patient is a male.

4. The method of claim 1, wherein said patient is a female.

5. The method of claim 1, wherein said patient is substantially free from cardiac disease.

6. The method of claim 1, wherein said administering step is selected from the group consisting of intranasal administration and respiratory inhalation.

7. A method, comprising:
   a) providing:
      i) a patient suffering from at least one symptom of sexual dysfunction who is not being treated with a drug that causes hypotensive effects and;
      ii) a pharmaceutical composition comprising a purified (+) enantiomer of monochloroflosequinan, or a pharmaceutically acceptable salt thereof; and
   b) administering said pharmaceutical composition to said patient under conditions such that at least one symptom of sexual dysfuction is reduced.

8. The method of claim 7, wherein said administering step is selected from the group consisting of intranasal administration and respiratory inhalation.

9. The method of claim 7 wherein, said patient has not been treated in the past with a drug that causes hypotensive effects.

10. The method of claim 7, wherein said composition is substantially free of the (−) enantiomer of monochloroflosequinan.

11. The method of claim 7, wherein said patient is a male.

12. The method of claim 7, wherein said patient is a female.

* * * * *